United States Patent
Chou et al.

(10) Patent No.: US 11,065,019 B1
(45) Date of Patent: Jul. 20, 2021

(54) ASPIRATION CATHETER SYSTEMS AND METHODS OF USE

(71) Applicant: Route 92 Medical, Inc., San Mateo, CA (US)

(72) Inventors: Tony M. Chou, San Mateo, CA (US); Scott D. Wilson, San Mateo, CA (US)

(73) Assignee: Route 92 Medical, Inc., San Mateo, CA (US)

( * ) Notice: Subject to any disclaimer, the term of this patent is extended or adjusted under 35 U.S.C. 154(b) by 0 days.

(21) Appl. No.: 17/174,194

(22) Filed: Feb. 11, 2021

Related U.S. Application Data

(63) Continuation-in-part of application No. 15/866,012, filed on Jan. 9, 2018, and a continuation-in-part of
(Continued)

(51) Int. Cl.
*A61B 17/22* (2006.01)
*A61M 25/01* (2006.01)
(Continued)

(52) U.S. Cl.
CPC ............ *A61B 17/22* (2013.01); *A61B 17/221* (2013.01); *A61M 25/01* (2013.01); *A61M 25/04* (2013.01);
(Continued)

(58) Field of Classification Search
CPC ........ A61B 17/12109; A61B 17/12136; A61B 17/22; A61B 2017/00243;
(Continued)

(56) References Cited

U.S. PATENT DOCUMENTS

| | | | |
|---|---|---|---|
| 2,623,520 A | 12/1952 | Bamford, Jr. et al. | |
| 2,730,101 A | 1/1956 | Hoffman | |

(Continued)

FOREIGN PATENT DOCUMENTS

| | | |
|---|---|---|
| CN | 101588835 A | 11/2009 |
| CN | 103260689 A | 8/2013 |

(Continued)

OTHER PUBLICATIONS

U.S. Appl. No. 15/699,401, filed Sep. 8, 2017, US 2017-0368309.
(Continued)

*Primary Examiner* — Brandy S Lee
(74) *Attorney, Agent, or Firm* — Mintz Levin Cohn Ferris Glovsky and Popeo, P.C.

(57) ABSTRACT

Described are methods, systems, devices for facilitation of intraluminal medical procedures within the neurovasculature. A catheter advancement device includes a flexible elongate body having a proximal end, a distal end, and a single lumen extending therebetween. The flexible elongate body has a proximal segment, an intermediate segment, and a tip segment. The proximal segment includes a hypotube coated with a polymer. The intermediate segment includes an unreinforced polymer having a durometer of no more than 72 D. The tip segment is formed of a polymer different from the intermediate segment and has a durometer of no more than about 35 D and a length of at least 5 cm. The tip segment has a tapered portion that tapers distally from a first outer diameter to a second outer diameter over a length of between 1 and 3 cm.

30 Claims, 16 Drawing Sheets

Related U.S. Application Data application No. 15/727,373, filed on Oct. 6, 2017, which is a continuation of application No. 15/217,810, filed on Jul. 22, 2016, now Pat. No. 10,426,497, application No. 17/174,194, which is a continuation-in-part of application No. 16/584,351, filed on Sep. 26, 2019, which is a continuation of application No. 15/875,214, filed on Jan. 19, 2018, now Pat. No. 10,799,669, application No. 17/174,194, which is a continuation-in-part of application No. 16/543,215, filed on Aug. 16, 2019, which is a continuation of application No. 15/856,979, filed on Dec. 28, 2017, now Pat. No. 10,456,555, which is a continuation of application No. 15/805,673, filed on Nov. 7, 2017, now Pat. No. 10,485,952, which is a continuation of application No. 15/015,799, filed on Feb. 4, 2016, now Pat. No. 9,820,761.

(60) Provisional application No. 62/444,584, filed on Jan. 10, 2017, provisional application No. 62/607,510, filed on Dec. 19, 2017, provisional application No. 62/196,613, filed on Jul. 24, 2015, provisional application No. 62/275,939, filed on Jan. 7, 2016, provisional application No. 62/301,857, filed on Mar. 1, 2016, provisional application No. 62/448,678, filed on Jan. 20, 2017, provisional application No. 62/517,005, filed on Jun. 8, 2017, provisional application No. 62/111,841, filed on Feb. 4, 2015, provisional application No. 62/142,637, filed on Apr. 3, 2015.

(51) Int. Cl.
*A61M 25/04* (2006.01)
*A61M 25/06* (2006.01)
*A61B 17/221* (2006.01)
*A61M 25/09* (2006.01)
*A61B 17/00* (2006.01)

(52) U.S. Cl.
CPC .............. *A61M 25/0662* (2013.01); *A61B 2017/00986* (2013.01); *A61B 2017/22047* (2013.01); *A61B 2017/22049* (2013.01); *A61B 2017/22069* (2013.01); *A61M 2025/0681* (2013.01); *A61M 2025/09125* (2013.01)

(58) Field of Classification Search
CPC ... A61B 2017/22079; A61B 2217/005; A61M 2025/0008; A61M 2205/584; A61M 2210/0693; A61M 2210/12; A61M 25/0045; A61M 25/0052; A61M 25/01; A61M 25/10
See application file for complete search history.

(56) References Cited

U.S. PATENT DOCUMENTS

| | | |
|---|---|---|
| 3,612,050 A | 10/1971 | Sheridan |
| 3,631,848 A | 1/1972 | Muller |
| 3,949,757 A | 4/1976 | Sabel |
| 3,996,938 A | 12/1976 | Clark, III |
| 4,013,080 A | 3/1977 | Froning |
| 4,020,829 A | 5/1977 | Willson et al. |
| 4,033,331 A | 7/1977 | Guss et al. |
| 4,174,715 A | 11/1979 | Hasson |
| 4,319,580 A | 3/1982 | Colley et al. |
| 4,323,071 A | 4/1982 | Simpson et al. |
| 4,406,656 A | 9/1983 | Nattier et al. |
| 4,610,662 A | 9/1986 | Weikl et al. |
| 4,619,263 A | 10/1986 | Frisbie et al. |
| 4,676,249 A | 6/1987 | Arenas et al. |
| 4,723,549 A | 2/1988 | Wholey et al. |
| 4,728,319 A | 3/1988 | Masch |
| 4,739,768 A | 4/1988 | Engelson |
| 4,784,636 A | 11/1988 | Rydell |
| 4,790,812 A | 12/1988 | Hawkins, Jr. et al. |
| 4,794,928 A | 1/1989 | Kletschka |
| 4,795,434 A | 1/1989 | Kujawski |
| 4,799,496 A | 1/1989 | Hargreaves et al. |
| 4,834,709 A | 5/1989 | Banning et al. |
| 4,863,431 A | 9/1989 | Vaillancourt |
| 4,873,978 A | 10/1989 | Ginsburg |
| 4,873,979 A | 10/1989 | Hanna |
| 4,883,460 A | 11/1989 | Zanetti |
| 4,887,613 A | 12/1989 | Farr et al. |
| 4,898,575 A | 2/1990 | Fischell et al. |
| 4,900,303 A | 2/1990 | Lemelson |
| 4,921,484 A | 5/1990 | Hillstead |
| 4,923,462 A | 5/1990 | Stevens |
| 4,946,443 A | 8/1990 | Hauser et al. |
| 4,994,067 A | 2/1991 | Summers |
| 4,998,919 A | 3/1991 | Schnepp-Pesch et al. |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Ya |
| 5,102,415 A | 4/1992 | Guenther et al. |
| 5,103,827 A | 4/1992 | Smith |
| 5,108,419 A | 4/1992 | Reger et al. |
| 5,152,277 A | 10/1992 | Honda et al. |
| 5,161,534 A | 11/1992 | Berthiaume |
| 5,163,906 A | 11/1992 | Ahmadi |
| 5,185,004 A | 2/1993 | Lashinski |
| 5,188,621 A | 2/1993 | Samson |
| 5,200,248 A | 4/1993 | Thompson et al. |
| 5,207,648 A | 5/1993 | Gross |
| 5,211,651 A | 5/1993 | Reger et al. |
| 5,217,705 A | 6/1993 | Reno et al. |
| 5,219,332 A | 6/1993 | Nelson et al. |
| 5,243,997 A | 9/1993 | Uflacker et al. |
| 5,267,960 A | 12/1993 | Hayman et al. |
| 5,269,297 A | 12/1993 | Weng et al. |
| 5,308,318 A | 5/1994 | Plassche, Jr. |
| 5,312,338 A | 5/1994 | Nelson et al. |
| 5,325,868 A | 7/1994 | Kimmelstiel |
| 5,338,300 A | 8/1994 | Cox |
| 5,352,197 A | 10/1994 | Hammersmark et al. |
| 5,364,358 A | 11/1994 | Hewitt et al. |
| 5,370,623 A | 12/1994 | Kreamer |
| 5,385,562 A | 1/1995 | Adams et al. |
| 5,392,778 A | 2/1995 | Horzewski |
| 5,395,383 A | 3/1995 | Adams et al. |
| 5,413,575 A | 5/1995 | Haenggi |
| 5,423,331 A | 6/1995 | Wysham |
| 5,438,993 A | 8/1995 | Lynch et al. |
| 5,441,051 A | 8/1995 | Hileman et al. |
| 5,454,795 A | 10/1995 | Samson |
| 5,465,716 A | 11/1995 | Avitall |
| 5,466,222 A | 11/1995 | Ressemann et al. |
| 5,484,407 A | 1/1996 | Osypka |
| 5,485,667 A | 1/1996 | Kleshinski |
| 5,490,859 A | 2/1996 | Mische et al. |
| 5,501,694 A | 3/1996 | Ressemann et al. |
| 5,527,292 A | 6/1996 | Adams et al. |
| 5,533,967 A | 7/1996 | Imran |
| 5,538,512 A | 7/1996 | Zenzon et al. |
| 5,542,936 A | 8/1996 | Razi |
| 5,546,958 A | 8/1996 | Thorud et al. |
| 5,549,119 A | 8/1996 | Solar |
| 5,549,626 A | 8/1996 | Miller et al. |
| 5,571,122 A | 11/1996 | Kelly et al. |
| 5,578,009 A | 11/1996 | Kraus et al. |
| 5,591,194 A | 1/1997 | Berthiaume |
| 5,599,307 A | 2/1997 | Bacher et al. |
| 5,643,254 A | 7/1997 | Scheldrup et al. |
| 5,658,263 A | 8/1997 | Dang et al. |
| 5,658,309 A | 8/1997 | Berthiaume et al. |
| 5,662,622 A | 9/1997 | Gore et al. |
| 5,695,483 A | 12/1997 | Samson |

(56) References Cited

U.S. PATENT DOCUMENTS

| | | |
|---|---|---|
| 5,702,373 A | 12/1997 | Samson |
| 5,702,439 A | 12/1997 | Keith et al. |
| 5,720,764 A | 2/1998 | Naderlinger |
| 5,766,191 A | 6/1998 | Trerotola |
| 5,776,141 A | 7/1998 | Klein et al. |
| 5,776,142 A | 7/1998 | Gunderson |
| 5,810,874 A | 9/1998 | Lefebvre |
| 5,814,064 A | 9/1998 | Daniel et al. |
| 5,817,101 A | 10/1998 | Fiedler |
| 5,827,242 A | 10/1998 | Follmer et al. |
| 5,836,868 A | 11/1998 | Ressemann et al. |
| 5,843,002 A | 12/1998 | Pecor et al. |
| 5,843,051 A | 12/1998 | Adams et al. |
| 5,843,103 A | 12/1998 | Wulfman |
| 5,851,189 A | 12/1998 | Forber |
| 5,876,375 A | 3/1999 | Penny |
| 5,882,329 A | 3/1999 | Patterson et al. |
| 5,885,209 A | 3/1999 | Green |
| 5,891,114 A | 4/1999 | Chien et al. |
| 5,897,567 A | 4/1999 | Ressemann et al. |
| 5,899,890 A | 5/1999 | Chiang et al. |
| 5,899,892 A | 5/1999 | Mortier et al. |
| 5,910,154 A | 6/1999 | Tsugita et al. |
| 5,911,725 A | 6/1999 | Boury |
| 5,911,734 A | 6/1999 | Tsugita et al. |
| 5,916,192 A | 6/1999 | Nita et al. |
| 5,928,260 A | 7/1999 | Chin et al. |
| 5,935,139 A | 8/1999 | Bates |
| 5,938,645 A | 8/1999 | Gordon |
| 5,941,869 A | 8/1999 | Patterson et al. |
| 5,972,019 A | 10/1999 | Engelson et al. |
| 5,997,523 A | 12/1999 | Jang |
| 5,997,557 A | 12/1999 | Barbut et al. |
| 6,007,530 A | 12/1999 | Domhofer et al. |
| 6,010,522 A | 1/2000 | Barbut et al. |
| 6,022,336 A | 2/2000 | Zadno-Azizi et al. |
| 6,030,349 A | 2/2000 | Wilson et al. |
| 6,030,369 A | 2/2000 | Engelson et al. |
| 6,066,149 A | 5/2000 | Samson et al. |
| 6,090,118 A | 7/2000 | McGuckin, Jr. |
| 6,106,530 A | 8/2000 | Harada |
| 6,117,141 A | 9/2000 | Ouchi |
| 6,120,480 A | 9/2000 | Zhang et al. |
| 6,135,991 A | 10/2000 | Muni et al. |
| 6,142,987 A | 11/2000 | Tsugita |
| 6,146,396 A | 11/2000 | Konya et al. |
| 6,156,005 A | 12/2000 | Theron |
| 6,159,195 A | 12/2000 | Ha et al. |
| 6,159,230 A | 12/2000 | Samuels |
| 6,165,163 A | 12/2000 | Chien et al. |
| 6,165,167 A | 12/2000 | Delaloye |
| 6,165,199 A | 12/2000 | Barbut |
| 6,168,579 B1 | 1/2001 | Tsugita |
| 6,171,295 B1 | 1/2001 | Garabedian et al. |
| 6,203,561 B1 | 3/2001 | Ramee et al. |
| 6,206,868 B1 | 3/2001 | Parodi |
| 6,221,038 B1 | 4/2001 | Brisken |
| 6,221,049 B1 | 4/2001 | Selmon et al. |
| 6,228,046 B1 | 5/2001 | Brisken |
| 6,238,402 B1 | 5/2001 | Sullivan, III et al. |
| 6,238,412 B1 | 5/2001 | Dubrul et al. |
| 6,238,430 B1 | 5/2001 | Klumb et al. |
| 6,240,231 B1 | 5/2001 | Ferrera et al. |
| 6,258,052 B1 | 7/2001 | Milo |
| 6,258,115 B1 | 7/2001 | Dubrul |
| 6,270,477 B1 | 8/2001 | Bagaoisan et al. |
| 6,277,115 B1 | 8/2001 | Saadat |
| 6,277,139 B1 | 8/2001 | Levinson et al. |
| 6,295,989 B1 | 10/2001 | Connors, III |
| 6,306,163 B1 | 10/2001 | Fitz |
| 6,346,116 B1 | 2/2002 | Brooks et al. |
| 6,361,545 B1 | 3/2002 | Macoviak et al. |
| 6,364,894 B1 | 4/2002 | Healy et al. |
| 6,368,338 B1 | 4/2002 | Konya et al. |
| 6,391,044 B1 | 5/2002 | Yadav et al. |
| 6,394,976 B1 | 5/2002 | Winston et al. |
| 6,451,005 B1 | 9/2002 | Saitou et al. |
| 6,454,741 B1 | 9/2002 | Muni et al. |
| 6,454,775 B1 | 9/2002 | Demarais et al. |
| 6,468,219 B1 | 10/2002 | Njemanze |
| 6,475,195 B1 | 11/2002 | Voda |
| 6,485,466 B2 | 11/2002 | Hamilton |
| 6,485,500 B1 | 11/2002 | Kokish et al. |
| 6,485,501 B1 | 11/2002 | Green |
| 6,511,470 B1 | 1/2003 | Hamilton |
| 6,511,471 B2 | 1/2003 | Rosenman et al. |
| 6,514,261 B1 | 2/2003 | Randall et al. |
| 6,514,273 B1 | 2/2003 | Voss et al. |
| 6,524,303 B1 | 2/2003 | Garibaldi |
| 6,537,241 B1 | 3/2003 | Odland |
| 6,537,295 B2 | 3/2003 | Petersen |
| 6,540,768 B1 | 4/2003 | Diaz et al. |
| 6,551,302 B1 | 4/2003 | Rosinko et al. |
| 6,554,820 B1 | 4/2003 | Wendlandt et al. |
| 6,554,827 B2 | 4/2003 | Chandrasekaran et al. |
| 6,558,377 B2 | 5/2003 | Lee et al. |
| 6,558,405 B1 | 5/2003 | McInnes |
| 6,569,148 B2 | 5/2003 | Bagaoisan et al. |
| 6,579,246 B2 | 6/2003 | Jacobsen et al. |
| 6,579,484 B1 | 6/2003 | Tieman et al. |
| 6,582,440 B1 | 6/2003 | Brumbach |
| 6,589,262 B1 | 7/2003 | Honebrink et al. |
| 6,596,011 B2 | 7/2003 | Johnson et al. |
| 6,610,077 B1 | 8/2003 | Hancock et al. |
| 6,616,681 B2 | 9/2003 | Hanson et al. |
| 6,620,148 B1 | 9/2003 | Tsugita |
| 6,676,637 B1 | 1/2004 | Bonnette et al. |
| 6,689,144 B2 | 2/2004 | Gerberding |
| 6,692,473 B2 | 2/2004 | St. Cyr et al. |
| 6,695,858 B1 | 2/2004 | Dubrul et al. |
| 6,695,865 B2 | 2/2004 | Boyle et al. |
| 6,702,834 B1 | 3/2004 | Boylan et al. |
| 6,740,104 B1 | 5/2004 | Solar et al. |
| 6,755,803 B1 | 6/2004 | Le et al. |
| 6,755,812 B2 | 6/2004 | Peterson et al. |
| 6,773,448 B2 | 8/2004 | Kusleika et al. |
| 6,805,684 B2 | 10/2004 | Bonnette et al. |
| 6,805,692 B2 | 10/2004 | Muni et al. |
| 6,824,550 B1 | 11/2004 | Noriega et al. |
| 6,824,553 B1 | 11/2004 | Samson et al. |
| 6,866,669 B2 | 3/2005 | Buzzard et al. |
| 6,878,151 B2 | 4/2005 | Carrison et al. |
| 6,879,854 B2 | 4/2005 | Windheuser et al. |
| 6,911,036 B2 | 6/2005 | Douk et al. |
| 6,926,658 B2 | 8/2005 | Faman |
| 6,945,956 B2 | 9/2005 | Waldhauser et al. |
| 6,949,104 B2 | 9/2005 | Griffis et al. |
| 6,951,570 B2 | 10/2005 | Linder et al. |
| 6,958,059 B2 | 10/2005 | Zadno-Azizi |
| 6,969,395 B2 | 11/2005 | Eskuri |
| 6,977,068 B1 | 12/2005 | Nair et al. |
| 6,991,642 B2 | 1/2006 | Petersen |
| 7,033,325 B1 | 4/2006 | Sullivan |
| 7,037,267 B1 | 5/2006 | Lipson et al. |
| 7,052,500 B2 | 5/2006 | Bashiri et al. |
| 7,056,328 B2 | 6/2006 | Arnott |
| 7,104,979 B2 | 9/2006 | Jansen et al. |
| 7,115,134 B2 | 10/2006 | Chambers |
| 7,115,138 B2 | 10/2006 | Renati et al. |
| 7,166,120 B2 | 1/2007 | Kusleika |
| 7,220,271 B2 | 5/2007 | Clubb et al. |
| 7,229,431 B2 | 6/2007 | Houser et al. |
| 7,229,463 B2 | 6/2007 | Sutton et al. |
| 7,229,464 B2 | 6/2007 | Hanson et al. |
| 7,232,452 B2 | 6/2007 | Adams et al. |
| 7,235,061 B2 | 6/2007 | Tsugita |
| 7,285,126 B2 | 10/2007 | Sepetka et al. |
| 7,309,334 B2 | 12/2007 | von Hoffmann |
| 7,316,678 B2 | 1/2008 | Nash et al. |
| 7,329,278 B2 | 2/2008 | Seguin et al. |
| 7,374,560 B2 | 5/2008 | Ressemann et al. |
| 7,374,564 B2 | 5/2008 | Brown |
| 7,449,010 B1 | 11/2008 | Hayase et al. |
| 7,476,232 B2 | 1/2009 | Deal |

(56) References Cited

U.S. PATENT DOCUMENTS

| | | |
|---|---|---|
| 7,507,229 B2 | 3/2009 | Hewitt et al. |
| 7,537,568 B2 | 5/2009 | Moehring |
| 7,549,974 B2 | 6/2009 | Nayak |
| 7,558,622 B2 | 7/2009 | Tran |
| 7,604,612 B2 | 10/2009 | Ressemann et al. |
| 7,625,207 B2 | 12/2009 | Hershey et al. |
| 7,691,121 B2 | 4/2010 | Rosenbluth et al. |
| 7,717,934 B2 | 5/2010 | Kusleika |
| 7,736,355 B2 | 6/2010 | Itou et al. |
| 7,771,358 B2 | 8/2010 | Moehring et al. |
| 7,785,286 B2 | 8/2010 | Magnin et al. |
| 7,803,136 B2 | 9/2010 | Schatz |
| 7,837,692 B2 | 11/2010 | Mulholland et al. |
| 7,842,055 B2 | 11/2010 | Pintor et al. |
| 7,850,654 B2 | 12/2010 | Belhe et al. |
| 7,854,746 B2 | 12/2010 | Dom et al. |
| 7,879,062 B2 | 2/2011 | Galdonik et al. |
| 7,905,891 B2 | 3/2011 | Self |
| 7,931,659 B2 | 4/2011 | Bose et al. |
| 7,938,820 B2 | 5/2011 | Webster et al. |
| 7,967,789 B2 | 6/2011 | Solar et al. |
| 7,972,294 B2 | 7/2011 | Nash et al. |
| 7,988,646 B2 | 8/2011 | Taber |
| 8,021,351 B2 | 9/2011 | Boldenow et al. |
| 8,048,032 B2 | 11/2011 | Root et al. |
| 8,070,694 B2 | 12/2011 | Galdonik et al. |
| 8,084,246 B2 | 12/2011 | Hoon et al. |
| 8,092,483 B2 | 1/2012 | Galdonik et al. |
| 8,114,032 B2 | 2/2012 | Ferry et al. |
| 8,142,413 B2 | 3/2012 | Root et al. |
| RE43,300 E | 4/2012 | Saadat et al. |
| 8,157,760 B2 | 4/2012 | Criado et al. |
| 8,172,831 B2 | 5/2012 | Webler, Jr. |
| 8,211,023 B2 | 7/2012 | Swan et al. |
| 8,231,600 B2 | 7/2012 | von Hoffmann |
| 8,235,968 B2 | 8/2012 | Tremaglio |
| 8,251,978 B2 | 8/2012 | Nash et al. |
| 8,292,850 B2 | 10/2012 | Root et al. |
| 8,308,712 B2 | 11/2012 | Provost et al. |
| 8,361,105 B2 | 1/2013 | Adams et al. |
| 8,366,735 B2 | 2/2013 | Bose et al. |
| 8,419,786 B2 | 4/2013 | Cottone, Jr. et al. |
| 8,425,549 B2 | 4/2013 | Lenker et al. |
| 8,460,312 B2 | 6/2013 | Bose et al. |
| 8,465,456 B2 | 6/2013 | Stivland |
| 8,523,801 B2 | 9/2013 | Nash et al. |
| 8,535,272 B2 | 9/2013 | Wang et al. |
| 8,540,759 B2 | 9/2013 | Porter |
| 8,609,426 B2 | 12/2013 | Silver |
| 8,636,714 B2 | 1/2014 | McFerran |
| 8,663,259 B2 | 3/2014 | Levine et al. |
| 8,682,411 B2 | 3/2014 | Kassab et al. |
| 8,690,907 B1 | 4/2014 | Janardhan et al. |
| 8,702,680 B2 | 4/2014 | Jimenez et al. |
| 8,708,954 B2 | 4/2014 | Webler |
| 8,725,249 B2 | 5/2014 | Bar-Yoseph et al. |
| 8,734,374 B2 | 5/2014 | Aklog et al. |
| 8,758,325 B2 | 6/2014 | Webster et al. |
| 8,764,779 B2 | 7/2014 | Levine et al. |
| 8,764,813 B2 | 7/2014 | Jantzen et al. |
| 8,795,305 B2 | 8/2014 | Martin et al. |
| 8,801,749 B2 | 8/2014 | Adams et al. |
| 8,814,892 B2 | 8/2014 | Galdonik et al. |
| 8,876,776 B2 | 11/2014 | Kassab et al. |
| 8,932,286 B2 | 1/2015 | Terry et al. |
| 8,932,320 B1 | 1/2015 | Janardhan et al. |
| RE45,380 E | 2/2015 | Root et al. |
| 8,974,411 B2 | 3/2015 | McKinnon |
| 8,996,095 B2 | 3/2015 | Anderson et al. |
| 9,014,786 B2 | 4/2015 | Carmeli et al. |
| 9,023,070 B2 | 5/2015 | Levine et al. |
| 9,034,007 B2 | 5/2015 | Janardhan |
| 9,107,691 B2 | 8/2015 | Fojtik |
| 9,119,656 B2 | 9/2015 | Bose et al. |
| 9,144,383 B2 | 9/2015 | Zharov |
| 9,144,662 B2 | 9/2015 | Di Capri et al. |
| RE45,760 E | 10/2015 | Root et al. |
| RE45,776 E | 10/2015 | Root et al. |
| 9,199,057 B2 | 12/2015 | Nielsen |
| 9,220,562 B2 | 12/2015 | Brannan et al. |
| 9,233,230 B2 | 1/2016 | Puhasmagi et al. |
| 9,241,699 B1 | 1/2016 | Kume et al. |
| 9,259,215 B2 | 2/2016 | Chou et al. |
| 9,259,228 B2 | 2/2016 | Cruise et al. |
| 9,265,512 B2 | 2/2016 | Garrison et al. |
| 9,278,201 B2 | 3/2016 | Rapaport et al. |
| 9,282,992 B2 | 3/2016 | Levine et al. |
| 9,295,817 B2 | 3/2016 | Chang |
| 9,314,268 B2 | 4/2016 | Cahill |
| 9,351,993 B2 | 5/2016 | Cruise et al. |
| 9,352,123 B2 | 5/2016 | Zhou et al. |
| 9,370,639 B2 | 6/2016 | Plassman et al. |
| 9,375,223 B2 | 6/2016 | Wallace |
| 9,381,278 B2 | 7/2016 | Constant et al. |
| 9,399,118 B2 | 7/2016 | Kume et al. |
| RE46,116 E | 8/2016 | Root et al. |
| 9,408,916 B2 | 8/2016 | Cruise et al. |
| 9,414,819 B2 | 8/2016 | Fitz et al. |
| 9,433,427 B2 | 9/2016 | Look et al. |
| 9,439,791 B2 | 9/2016 | Vong et al. |
| 9,451,884 B2 | 9/2016 | Zharov et al. |
| 9,451,963 B2 | 9/2016 | Cruise et al. |
| 9,486,221 B2 | 11/2016 | Cruise et al. |
| 9,486,611 B2 | 11/2016 | Petersen et al. |
| 9,492,637 B2 | 11/2016 | Garrison et al. |
| 9,504,476 B2 | 11/2016 | Gulachenski |
| 9,510,855 B2 | 12/2016 | Rapaport et al. |
| 9,526,504 B2 | 12/2016 | Chang |
| 9,526,505 B2 | 12/2016 | Marks et al. |
| 9,532,792 B2 | 1/2017 | Galdonik et al. |
| 9,533,344 B2 | 1/2017 | Monetti et al. |
| 9,539,022 B2 | 1/2017 | Bowman |
| 9,539,122 B2 | 1/2017 | Burke et al. |
| 9,546,236 B2 | 1/2017 | Cruise et al. |
| 9,561,121 B2 | 2/2017 | Sudin et al. |
| 9,561,125 B2 | 2/2017 | Bowman et al. |
| 9,561,345 B2 | 2/2017 | Garrison et al. |
| 9,597,101 B2 | 3/2017 | Galdonik et al. |
| 9,615,832 B2 | 4/2017 | Bose et al. |
| 9,622,753 B2 | 4/2017 | Cox |
| 9,623,228 B2 | 4/2017 | Ryan et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |
| 9,688,788 B2 | 6/2017 | Plotkin et al. |
| 9,693,789 B2 | 7/2017 | Garrison et al. |
| 9,693,852 B2 | 7/2017 | Lam et al. |
| 9,717,500 B2 | 8/2017 | Tieu et al. |
| 9,724,103 B2 | 8/2017 | Cruise et al. |
| 9,764,111 B2 | 9/2017 | Gulachenski |
| 9,764,118 B2 | 9/2017 | Anderson et al. |
| 9,770,251 B2 | 9/2017 | Bowman et al. |
| 9,789,242 B2 | 10/2017 | Criado et al. |
| 9,803,043 B2 | 10/2017 | Cruise et al. |
| 9,820,761 B2 | 11/2017 | Garrison et al. |
| 9,827,047 B2 | 11/2017 | Fudaba et al. |
| 9,861,783 B2 | 1/2018 | Garrison et al. |
| 9,877,731 B2 | 1/2018 | Cruise et al. |
| 9,883,885 B2 | 2/2018 | Hendrick et al. |
| 9,907,880 B2 | 3/2018 | Cruise et al. |
| 10,058,339 B2 | 8/2018 | Galdonik et al. |
| 10,124,146 B2 | 11/2018 | Di Caprio et al. |
| 10,183,146 B2 | 1/2019 | Yang et al. |
| 10,192,230 B2 | 1/2019 | Look et al. |
| 10,213,582 B2 | 2/2019 | Garrison et al. |
| 10,441,301 B2 | 10/2019 | Vale et al. |
| 10,485,956 B2 | 11/2019 | O'Donovan |
| 2001/0014790 A1 | 8/2001 | Heller et al. |

(56) References Cited

U.S. PATENT DOCUMENTS

| | | |
|---|---|---|
| 2001/0031980 A1 | 10/2001 | Wensel et al. |
| 2001/0044600 A1 | 11/2001 | Elkins |
| 2001/0044632 A1 | 11/2001 | Daniel et al. |
| 2001/0051811 A1 | 12/2001 | Bonnette et al. |
| 2002/0016565 A1 | 2/2002 | Zadno-Azizi et al. |
| 2002/0026145 A1 | 2/2002 | Bagaoisan et al. |
| 2002/0035347 A1 | 3/2002 | Bagaoisan et al. |
| 2002/0055747 A1 | 5/2002 | Cano et al. |
| 2002/0062133 A1 | 5/2002 | Gilson et al. |
| 2002/0091407 A1 | 7/2002 | Zadno-Azizi et al. |
| 2002/0095174 A1 | 7/2002 | Tsugita et al. |
| 2002/0111648 A1 | 8/2002 | Kusleika et al. |
| 2002/0123765 A1 | 9/2002 | Sepetka et al. |
| 2002/0133111 A1 | 9/2002 | Shadduck |
| 2002/0138094 A1 | 9/2002 | Borillo et al. |
| 2002/0143362 A1 | 10/2002 | Macoviak et al. |
| 2002/0151927 A1 | 10/2002 | Douk et al. |
| 2002/0165571 A1 | 11/2002 | Hebert et al. |
| 2002/0165574 A1 | 11/2002 | Ressemann et al. |
| 2002/0169472 A1 | 11/2002 | Douk et al. |
| 2002/0173785 A1 | 11/2002 | Spear et al. |
| 2002/0177899 A1 | 11/2002 | Eum et al. |
| 2002/0183782 A1 | 12/2002 | Tsugita et al. |
| 2003/0023263 A1 | 1/2003 | Krolik et al. |
| 2003/0050600 A1 | 3/2003 | Ressemann et al. |
| 2003/0065353 A1 | 4/2003 | Horzevvski et al. |
| 2003/0120208 A1 | 6/2003 | Houser et al. |
| 2003/0135193 A1 | 7/2003 | Hilgers et al. |
| 2003/0135198 A1 | 7/2003 | Berhovv et al. |
| 2003/0135232 A1 | 7/2003 | Douk et al. |
| 2003/0191492 A1 | 10/2003 | Gellman et al. |
| 2003/0233038 A1 | 12/2003 | Hassett |
| 2004/0006344 A1 | 1/2004 | Nguyen et al. |
| 2004/0006365 A1 | 1/2004 | Brady et al. |
| 2004/0015151 A1 | 1/2004 | Chambers |
| 2004/0019322 A1 | 1/2004 | Hoffmann |
| 2004/0122360 A1 | 6/2004 | Waldhauser et al. |
| 2004/0153049 A1 | 8/2004 | Hewitt et al. |
| 2004/0153118 A1 | 8/2004 | Clubb et al. |
| 2004/0193177 A1 | 9/2004 | Houghton et al. |
| 2004/0220611 A1 | 11/2004 | Ogle |
| 2004/0236215 A1 | 11/2004 | Mihara et al. |
| 2004/0243102 A1 | 12/2004 | Berg et al. |
| 2004/0254602 A1 | 12/2004 | Lehe et al. |
| 2005/0004553 A1 | 1/2005 | Douk |
| 2005/0021075 A1 | 1/2005 | Bonnette et al. |
| 2005/0021152 A1 | 1/2005 | Ogle et al. |
| 2005/0027236 A1 | 2/2005 | Douk |
| 2005/0059957 A1 | 3/2005 | Campbell et al. |
| 2005/0085847 A1 | 4/2005 | Galdonik et al. |
| 2005/0103332 A1 | 5/2005 | Gingles et al. |
| 2005/0182386 A1 | 8/2005 | Aggerholm |
| 2005/0209631 A1 | 9/2005 | Galdonik et al. |
| 2005/0209674 A1 | 9/2005 | Kutscher et al. |
| 2005/0228479 A1 | 10/2005 | Pavcnik et al. |
| 2005/0277976 A1 | 12/2005 | Galdonik et al. |
| 2006/0020165 A1 | 1/2006 | Adams |
| 2006/0030835 A1 | 2/2006 | Sherman et al. |
| 2006/0030876 A1 | 2/2006 | Peacock et al. |
| 2006/0047301 A1 | 3/2006 | Ogle |
| 2006/0064036 A1 | 3/2006 | Osborne et al. |
| 2006/0069381 A1 | 3/2006 | Itou et al. |
| 2006/0079787 A1 | 4/2006 | Whiting et al. |
| 2006/0095062 A1 | 5/2006 | Stephens |
| 2006/0100530 A1 | 5/2006 | Kliot et al. |
| 2006/0129091 A1 | 6/2006 | Bonnette et al. |
| 2006/0195137 A1 | 8/2006 | Sepetka et al. |
| 2006/0200047 A1 | 9/2006 | Galdonik et al. |
| 2006/0200191 A1 | 9/2006 | Zadno-Azizi |
| 2006/0247755 A1 | 11/2006 | Pal et al. |
| 2006/0258987 A1 | 11/2006 | Lentz et al. |
| 2006/0259063 A1 | 11/2006 | Bates et al. |
| 2006/0264759 A1 | 11/2006 | Moehring et al. |
| 2007/0016132 A1 | 1/2007 | Oepen et al. |
| 2007/0043333 A1 | 2/2007 | Kampa et al. |
| 2007/0060888 A1 | 3/2007 | Goff et al. |
| 2007/0060908 A1 | 3/2007 | Webster et al. |
| 2007/0060911 A1 | 3/2007 | Webster et al. |
| 2007/0060944 A1 | 3/2007 | Boldenow et al. |
| 2007/0106211 A1 | 5/2007 | Provost-Tine et al. |
| 2007/0135733 A1 | 6/2007 | Soukup et al. |
| 2007/0185501 A1 | 8/2007 | Martin et al. |
| 2007/0185521 A1 | 8/2007 | Bui et al. |
| 2007/0185522 A1 | 8/2007 | Davies et al. |
| 2007/0208302 A1 | 9/2007 | Webster et al. |
| 2007/0227543 A1 | 10/2007 | Peichel |
| 2007/0250040 A1 | 10/2007 | Provost et al. |
| 2007/0250096 A1 | 10/2007 | Yamane et al. |
| 2007/0260115 A1 | 11/2007 | Brock et al. |
| 2007/0260219 A1 | 11/2007 | Root et al. |
| 2008/0033525 A1 | 2/2008 | Shaked et al. |
| 2008/0086110 A1 | 4/2008 | Galdonik et al. |
| 2008/0097251 A1 | 4/2008 | Babaev |
| 2008/0109088 A1 | 5/2008 | Galdonik et al. |
| 2008/0119890 A1 | 5/2008 | Adams et al. |
| 2008/0172066 A9 | 7/2008 | Galdonik et al. |
| 2008/0183128 A1 | 7/2008 | Morriss et al. |
| 2008/0188888 A1 | 8/2008 | Adams et al. |
| 2008/0195140 A1 | 8/2008 | Myla et al. |
| 2008/0234723 A1 | 9/2008 | Buiser et al. |
| 2008/0243222 A1 | 10/2008 | Schafersman et al. |
| 2008/0262350 A1 | 10/2008 | Unger |
| 2008/0294111 A1 | 11/2008 | Tal et al. |
| 2008/0312639 A1 | 12/2008 | Weber |
| 2009/0018525 A1 | 1/2009 | Waite et al. |
| 2009/0030400 A1* | 1/2009 | Bose .............. A61M 25/0054 604/510 |
| 2009/0082800 A1 | 3/2009 | Janardhan |
| 2009/0209857 A1 | 8/2009 | Secretain et al. |
| 2009/0227992 A1 | 9/2009 | Nir et al. |
| 2009/0234321 A1 | 9/2009 | Shapland et al. |
| 2009/0254166 A1 | 10/2009 | Chou et al. |
| 2009/0264865 A1 | 10/2009 | Kawai |
| 2009/0312699 A1 | 12/2009 | Pudelko et al. |
| 2010/0004607 A1 | 1/2010 | Wilson et al. |
| 2010/0022948 A1 | 1/2010 | Wilson et al. |
| 2010/0030141 A1 | 2/2010 | Chermoni |
| 2010/0030166 A1 | 2/2010 | Stivland |
| 2010/0049168 A1 | 2/2010 | Parker et al. |
| 2010/0057051 A1 | 3/2010 | Howat et al. |
| 2010/0114017 A1 | 5/2010 | Lenker et al. |
| 2010/0204672 A1 | 8/2010 | Lockhart et al. |
| 2010/0204684 A1 | 8/2010 | Garrison et al. |
| 2010/0211050 A1 | 8/2010 | Luther |
| 2010/0217235 A1 | 8/2010 | Thorstenson et al. |
| 2010/0217276 A1 | 8/2010 | Garrison et al. |
| 2010/0268029 A1 | 10/2010 | Phan et al. |
| 2010/0312141 A1 | 12/2010 | Keast et al. |
| 2011/0015482 A1 | 1/2011 | Carrillo, Jr. |
| 2011/0034986 A1 | 2/2011 | Chou et al. |
| 2011/0082373 A1 | 4/2011 | Gurley et al. |
| 2011/0106200 A1 | 5/2011 | Ziegler |
| 2011/0172678 A1 | 7/2011 | Behl et al. |
| 2011/0172700 A1 | 7/2011 | Bose et al. |
| 2011/0230859 A1 | 9/2011 | Galdonik et al. |
| 2011/0264133 A1 | 10/2011 | Hanlon et al. |
| 2012/0040858 A1 | 2/2012 | Ford et al. |
| 2012/0065479 A1 | 3/2012 | Lahiji et al. |
| 2012/0065490 A1 | 3/2012 | Zharov et al. |
| 2012/0071638 A1 | 3/2012 | Fojtik |
| 2012/0078140 A1 | 3/2012 | Nita |
| 2012/0095485 A1 | 4/2012 | Cully et al. |
| 2012/0101561 A1 | 4/2012 | Porter |
| 2012/0116350 A1 | 5/2012 | Strauss et al. |
| 2012/0123466 A1 | 5/2012 | Porter et al. |
| 2012/0150147 A1 | 6/2012 | Leynov et al. |
| 2012/0253313 A1 | 10/2012 | Galdonik et al. |
| 2012/0271281 A1 | 10/2012 | Schertiger |
| 2012/0310212 A1 | 12/2012 | Fischell et al. |
| 2012/0330196 A1 | 12/2012 | Nita |
| 2013/0006225 A1 | 1/2013 | Cucin |
| 2013/0018318 A1 | 1/2013 | Ravichandran et al. |
| 2013/0035628 A1 | 2/2013 | Garrison et al. |
| 2013/0046285 A1 | 2/2013 | Griffin et al. |

(56) References Cited

U.S. PATENT DOCUMENTS

| | | |
|---|---|---|
| 2013/0053792 A1 | 2/2013 | Fischell et al. |
| 2013/0116701 A1 | 5/2013 | Wang et al. |
| 2013/0158578 A1 | 6/2013 | Ghodke et al. |
| 2013/0281788 A1 | 10/2013 | Garrison |
| 2014/0018773 A1 | 1/2014 | Wang et al. |
| 2014/0025043 A1 | 1/2014 | Wang et al. |
| 2014/0039461 A1 | 2/2014 | Anderson et al. |
| 2014/0088510 A1 | 3/2014 | Nimkar et al. |
| 2014/0114287 A1 | 4/2014 | Beasley et al. |
| 2014/0155932 A1 | 6/2014 | Weishaupt et al. |
| 2014/0207043 A1 | 7/2014 | Anand et al. |
| 2014/0228808 A1 | 8/2014 | Webster et al. |
| 2014/0249508 A1 | 9/2014 | Wang et al. |
| 2014/0273920 A1 | 9/2014 | Smith |
| 2014/0276618 A1 | 9/2014 | Di Caprio et al. |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296868 A1 | 10/2014 | Garrison et al. |
| 2014/0296889 A1 | 10/2014 | Avneri et al. |
| 2014/0343537 A1 | 11/2014 | Eversull et al. |
| 2014/0358123 A1 | 12/2014 | Ueda et al. |
| 2014/0371709 A1 | 12/2014 | Allen et al. |
| 2015/0025562 A1 | 1/2015 | Dinh et al. |
| 2015/0080939 A1 | 3/2015 | Adams et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0151090 A1 | 6/2015 | Sutton et al. |
| 2015/0165160 A1 | 6/2015 | Thungana et al. |
| 2015/0173782 A1 | 6/2015 | Garrison et al. |
| 2015/0174368 A1 | 6/2015 | Garrison et al. |
| 2015/0265802 A1 | 9/2015 | Fukuoka et al. |
| 2015/0282821 A1 | 10/2015 | Look et al. |
| 2015/0327919 A1 | 11/2015 | Clopp et al. |
| 2015/0335857 A1 | 11/2015 | Ishikawa |
| 2015/0352330 A1 | 12/2015 | Wasdyke et al. |
| 2016/0008572 A1 | 1/2016 | Di Caprio et al. |
| 2016/0015935 A1 | 1/2016 | Chan et al. |
| 2016/0022964 A1 | 1/2016 | Goyal |
| 2016/0058459 A1 | 3/2016 | Bowman |
| 2016/0066931 A1 | 3/2016 | Kugler et al. |
| 2016/0081825 A1 | 3/2016 | Sudin et al. |
| 2016/0100819 A1 | 4/2016 | Tieu |
| 2016/0121081 A1 | 5/2016 | Iwano et al. |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0144157 A1 | 5/2016 | Gulachenski et al. |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney et al. |
| 2016/0206322 A1 | 7/2016 | Fitz et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346502 A1 | 12/2016 | Fuller et al. |
| 2016/0346508 A1 | 12/2016 | Williams et al. |
| 2016/0346509 A1 | 12/2016 | Anderson et al. |
| 2016/0361180 A1 | 12/2016 | Vong et al. |
| 2016/0361459 A1 | 12/2016 | Baldwin |
| 2016/0367272 A1 | 12/2016 | Garrison et al. |
| 2016/0367274 A1 | 12/2016 | Wallace |
| 2016/0367275 A1 | 12/2016 | Wallace |
| 2017/0007264 A1 | 1/2017 | Cruise et al. |
| 2017/0007277 A1 | 1/2017 | Drapeau et al. |
| 2017/0020540 A1 | 1/2017 | Chou et al. |
| 2017/0027604 A1 | 2/2017 | Wallace |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0056061 A1 | 3/2017 | Ogle et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0231647 A1 | 8/2017 | Saunders et al. |
| 2017/0239440 A1 | 8/2017 | Yang et al. |
| 2017/0246014 A1 | 8/2017 | Rapaport et al. |
| 2017/0252043 A1 | 9/2017 | Fuller et al. |
| 2017/0252536 A1 | 9/2017 | Yang et al. |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0333060 A1 | 11/2017 | Panian |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou et al. |
| 2017/0367713 A1 | 12/2017 | Greene, Jr. et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Panian |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0055516 A1 | 3/2018 | Baldwin et al. |
| 2018/0064453 A1 | 3/2018 | Garrison et al. |
| 2018/0116684 A1 | 5/2018 | Garrison et al. |
| 2018/0133436 A1 | 5/2018 | Garrison et al. |
| 2018/0193042 A1 | 7/2018 | Wilson et al. |
| 2018/0207399 A1 | 7/2018 | Chou et al. |
| 2018/0242978 A1 | 8/2018 | Chou et al. |
| 2018/0339130 A1 | 11/2018 | Ogle |
| 2018/0361114 A1 | 12/2018 | Chou et al. |
| 2019/0008534 A1 | 1/2019 | Garrison et al. |
| 2019/0046218 A1 | 2/2019 | Garrison et al. |
| 2019/0351182 A1 | 11/2019 | Chou et al. |
| 2019/0366042 A1 | 12/2019 | Garrison et al. |
| 2019/0366043 A1 | 12/2019 | Garrison et al. |
| 2020/0016369 A1 | 1/2020 | Garrison et al. |
| 2020/0023160 A1 | 1/2020 | Chou et al. |
| 2020/0038628 A1 | 2/2020 | Chou et al. |
| 2020/0046939 A1 | 2/2020 | Garrison et al. |
| 2020/0046940 A1 | 2/2020 | Garrison et al. |
| 2020/0060722 A1 | 2/2020 | O'Connell et al. |

(56) References Cited

U.S. PATENT DOCUMENTS

| | | | |
|---|---|---|---|
| 2020/0164178 A1 | 5/2020 | Garrison et al. |
| 2020/0187965 A1 | 6/2020 | Garrison et al. |
| 2020/0215306 A1 | 7/2020 | Garrison et al. |
| 2020/0289136 A1 | 9/2020 | Chou |
| 2020/0337716 A1 | 10/2020 | Garrison et al. |
| 2020/0345981 A1 | 11/2020 | Garrison et al. |

FOREIGN PATENT DOCUMENTS

| | | | |
|---|---|---|---|
| CN | 104739486 A | 7/2015 |
| CN | 105920720 A | 9/2016 |
| EP | 117940 A2 | 9/1984 |
| EP | 1226795 A2 | 7/2002 |
| EP | 1639951 A1 | 3/2006 |
| EP | 2 069 528 B1 | 3/2013 |
| GB | 2020557 A | 11/1979 |
| JP | H11-146883 A | 6/1999 |
| JP | 2014-138756 A | 7/2014 |
| WO | WO-93/17750 A1 | 9/1993 |
| WO | WO-94/02194 A1 | 2/1994 |
| WO | WO-95/05209 A1 | 2/1995 |
| WO | WO-98/38930 A1 | 9/1998 |
| WO | WO-00/16705 A1 | 3/2000 |
| WO | WO-02/055146 A1 | 7/2002 |
| WO | WO-02/085092 A2 | 10/2002 |
| WO | WO-2006/111944 A1 | 10/2006 |
| WO | WO-2006/127929 A2 | 11/2006 |
| WO | WO-2008/006111 A2 | 1/2008 |
| WO | WO-2014/203336 A1 | 12/2014 |
| WO | WO-2015/100178 A1 | 7/2015 |
| WO | WO-2015/157330 A1 | 10/2015 |

OTHER PUBLICATIONS

U.S. Appl. No. 15/727,373, filed Oct. 6, 2017, US 2018-0028205.
U.S. Appl. No. 15/747,089, filed Jan. 23, 2018, US 2018-0242978.
U.S. Appl. No. 15/866,012, filed Jan. 9, 2018, US 2018-0193042.
U.S. Appl. No. 16/414,532, filed May 16, 2019, US 2019-0351182.
U.S. Appl. No. 16/530,845, filed Aug. 2, 2019, US 2020-0023160.
U.S. Appl. No. 16/543,215, filed Aug. 16, 2019, US 2019-0366042.
U.S. Appl. No. 16/543,226, filed Aug. 16, 2019, US 2019-0366043.
U.S. Appl. No. 16/584,220, filed Sep. 26, 2019, US 2020-0016369.
U.S. Appl. No. 16/584,351, filed Sep. 26, 2019, US 2020-0038628.
U.S. Appl. No. 16/596,531, filed Oct. 8, 2019, US 2020-0046939.
U.S. Appl. No. 16/596,535, filed Oct. 8, 2019, US 2020-0046940.
U.S. Appl. No. 16/775,105, filed Jan. 28, 2020, US 2020-0164178.
U.S. Appl. No. 16/821,804, filed Mar. 17, 2020, US 2020-0215306.
U.S. Appl. No. 16/890,962, filed Jun. 2, 2020, US 2020-0289136.
U.S. Appl. No. 16/925,708, filed Jul. 10, 2020, US 2020-0337716.
U.S. Appl. No. 17/011,448, filed Sep. 3, 2020, US 2021-0052296.
U.S. Appl. No. 17/089,495, filed Nov. 4, 2020, US 2021-0045758.
U.S. Appl. No. 17/093,401, filed Nov. 9, 2020, US 2021-0069467.
"2007 International Stroke Conference: Abstracts." Stroke, vol. 38, No. 2, 2007, pp. 454-607. Web. Downloaded Jun. 13, 2017.
"2012 Buyer's Guide: Microcatheters." Endovascular Today, 2012, pp. 48-51.
"2017 Buyer's Guide: Microcatheters." Endovascular Today http://evtoday.com/buyers-guide/chart.asp?id=25. Accessed on Oct. 10, 2017. 11 pages.
"Asahi Fubuki Catheter Dilator Kit." Asahi-Intecc USA Medical. 2017. Web. Accessed Oct. 2, 2017. 3 pages. www.asahi-inteccusa-medical.com/medical-product/fubuki-dilator-kit/. Accessed Oct. 2, 2017.
"Trevo ProVue Retriever." Stryker Trevo® ProVue™. Retrieval System (by Concentric Medical®). (2016) Web. Apr. 13, 2018. 2 pages.
Farooq, Vasim et al. "Forward and Back Aspiration during ST-Elevation Myocardial Infarction: a Feasibility Study." EuroIntervention, vol. 11, No. 14, 2016, pp. 1639-48.
Farooq, Vasim et al. "The Use of A Guide Catheter Extension System as an Aid During Transradial Percutaneous Coronary Intervention of Coronary Artery Bypass Grafts." *Catheterization and Cardiovascular Interventions*, vol. 78, No. 6, 2011, pp. 847-63.
Feldman (1987) "Transcatheter Aspiration of a Thrombus in an Aortocoronary Saphenous Vein Graft," *American Journal of Cardiology*, 60(4):379-380.
Guidezilla Guide Extension Catheter, Boston Scientific 510k Submission, Feb. 19, 2013, 5 pages. Web. Accessed Oct. 23, 2017.
Heart and Stroke Foundation of Canada. "Vacuum cleaner sucks up strokes." *ScienceDaily*, Jun. 8, 2010, 4 pages, www.sciencedaily.com/releases/2010/06/100608162240.htm.
Kopeck, Rachel. "Penumbra, Inc. Launches 5MAX™ ACE—The Newest Clot Extraction Device to Treat Acute Ischemic Stroke Patients." *Penumbra Inc.*, Jul. 8, 2013, 3 pages, http://www.penumbrainc.com/news/penumbra-inc-launches-5max-ace-the-newest-clot-extraction-device-to-treat-acute-ischemic-stroke-patients/.
Merit Medical Systems Acquired Distal Access's SPINR Platform, Jul. 15, 2015, Digital Access, LLC; Merit Medical Systems, 5 pages. Web. Accessed Oct. 23, 2017.
Paullus WS, Pait TG, Rhoton AI Jr. Microsurgical exposure of the petrous portion of the carotid artery. J Neurosurg. 1977;47(5):713-726. (Year: 1977).
Pena, Carlos. "Letter to Sequent Medical Inc Re: K150894, Trade/Device Name: VIA™ 21 Microcatheter." Department of Health & Human Services, Aug. 28, 2015, 14 pages.
Penumbra, Inc., "Penumbra, Inc. Completes Pivotal Stroke Trial of Intracranial Revascularization," Press Release, (2007). Web. Accessed Jun. 14, 2017. 2 pages.
Penumbra, Inc., "The Penumbra Pivotal Stroke Trial: Safety and Effectiveness of a New Generation of Mechanical Devices for Clot Removal in Intracranial Large Vessel Occlusive Disease," *Stroke 2009*, 40:2761-2768. Web. Downloaded Jun. 15, 2017.
Reeder et al., "Aspiration Thrombectomy for Removal of Coronary Thrombus," *American Journal of Cardiology*. (Jul. 1, 1992) 70:107-110 (Abstract only).
Request for Ex Parte Reexamination Transmittal Form and Request for Ex Parte Reexamination pursuant to 37 CFR 1.150 of U.S. Pat. No. 9,820,761 dated Nov. 21, 2017. Request filed May 11, 2018 and assigned U.S. Appl. No. 90/014,136. 35 pages.
Seidel, A. et al. (2005). "Relationship between the diameter of great saphenous vein and body mass index," J Vasc Bras, vol. 4, No. 3, p. 265-269.
Simon et al., Hydrodynamic comparison of the Penumbra system and commonly available syringes in forced—suction thrombectomy, J. Neuro Intervent Surg 2014, 6, pp. 205-211. Web. Downloaded Oct. 18, 2017.
Simon, S. et al. (2014, e-published Nov. 14, 2013) "Exploring the efficacy of cyclic vs static aspiration in a cerebral thrombectomy model: an initial proof of concept study." *J. NeuroIntervent Surg* 6: 677-683. Web. Date accessed Oct. 18, 2017.
Spinnaker® Elite™Flow Directed Catheters Go with the Flow. Indications for Use. 2 page. Web. Aug. 27, 2019.
Spinnaker® Elite™ Flow Directed Catheters Go with the Flow. Promotional Brochure. 1 page. Web. Aug. 27, 2019.
Spiotta et al., Evolution of thrombectomy approaches and devices for acute stroke: a technical review, J. Neuro Intervent Surg 2015, 7, pp. 2-7. Web. Downloaded Oct. 18, 2017.
Stys, Adam T. et al. "A Novel Application of GuideLiner Catheter for Thrombectomy in Acute Myocardial Infarction: A Case Series." *Journal of Invasive Cardiology*, vol. 25, No. 11, 2013, pp. E254-59. 6 pages. (http://www.invasivecardiology.com/issue/4284).
Vijaywargiya et al "Anatomical study of petrous and cavernous parts of internal carotid artery". Anatomy and Cell Biology 2017;50: 163-170. (Year: 2017).
Webb et al, "Retrieval and Analysis of Particulate Debris After Saphenous Vein Graft Intervention," *Journal of the American College of Cardiology*, 34(2);468-475 (1999).
Yoo et al., "The Penumbra Stroke System: a technical review." *Journal of Neurointerventional Surgery*. 4:199-205 (2012). Web. Downloaded Jun. 15, 2017.

(56) References Cited

OTHER PUBLICATIONS

Zuckerman, Bram. "Letter to Cathera Inc: Re K151638, Trade/Device Name: Phenom™ Catheters." Department of Health & Human Services, Nov. 13, 2015, 6 pages.

* cited by examiner

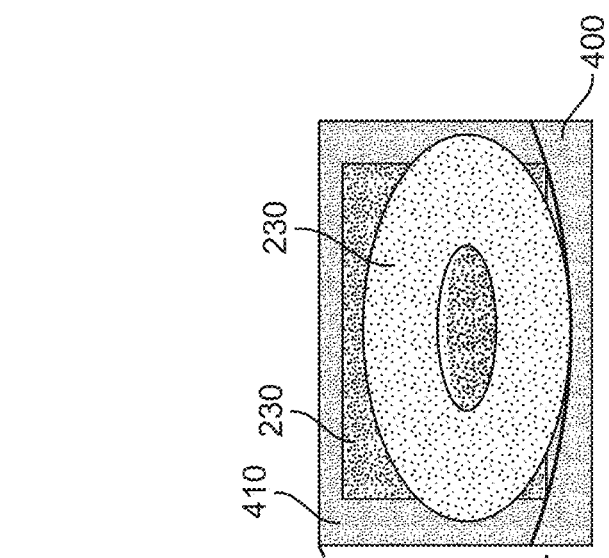
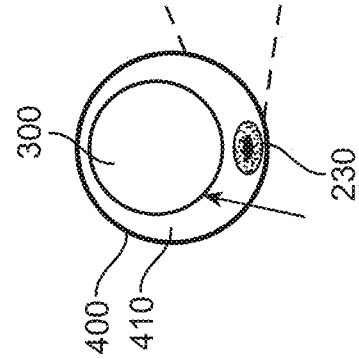
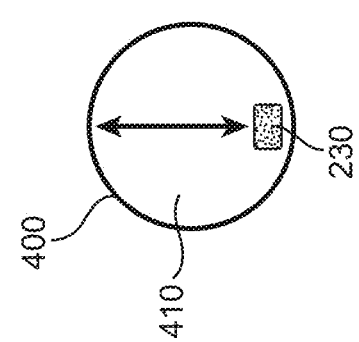
FIG. 4A
FIG. 4B
FIG. 4C
FIG. 4D
FIG. 4E

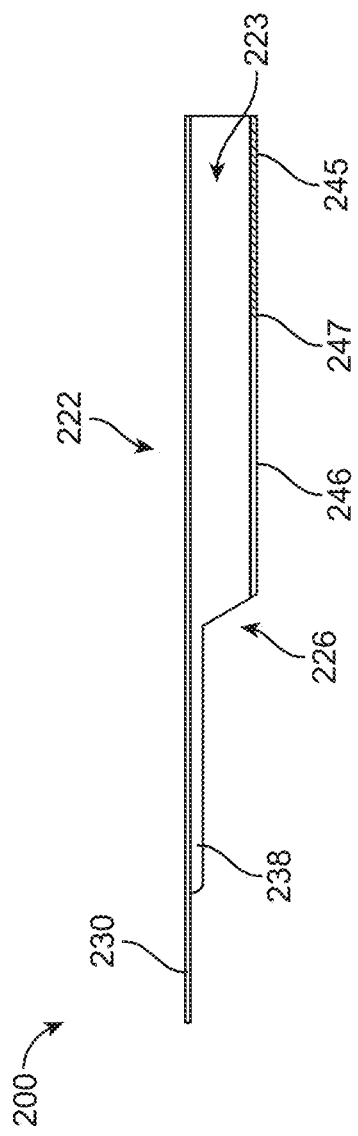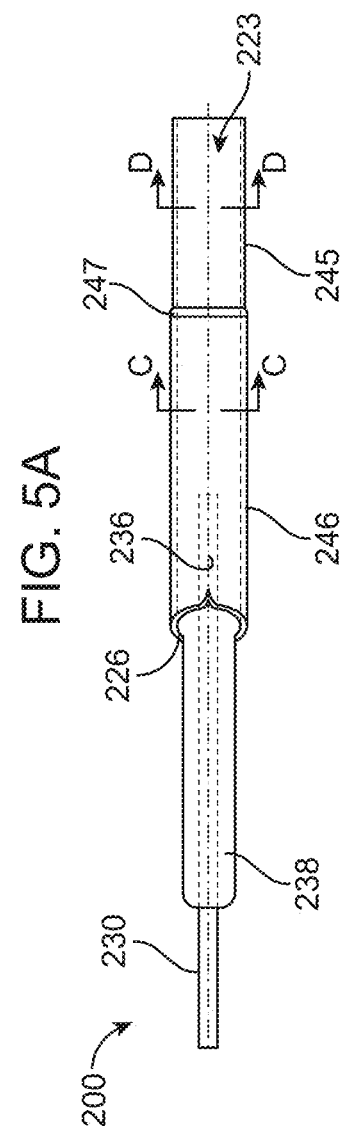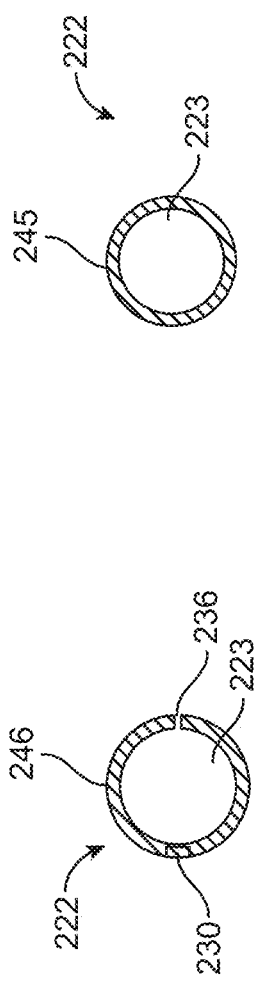

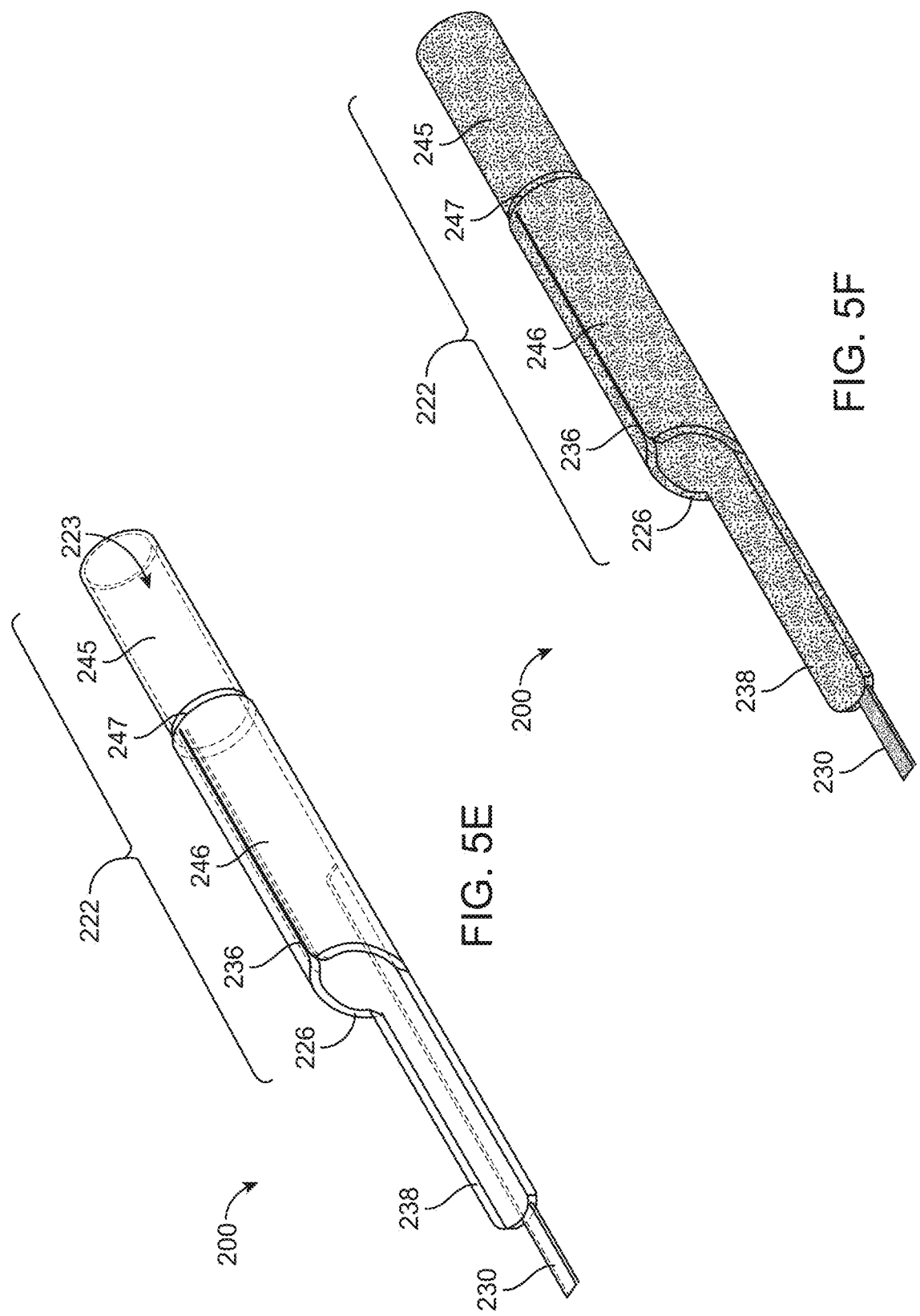

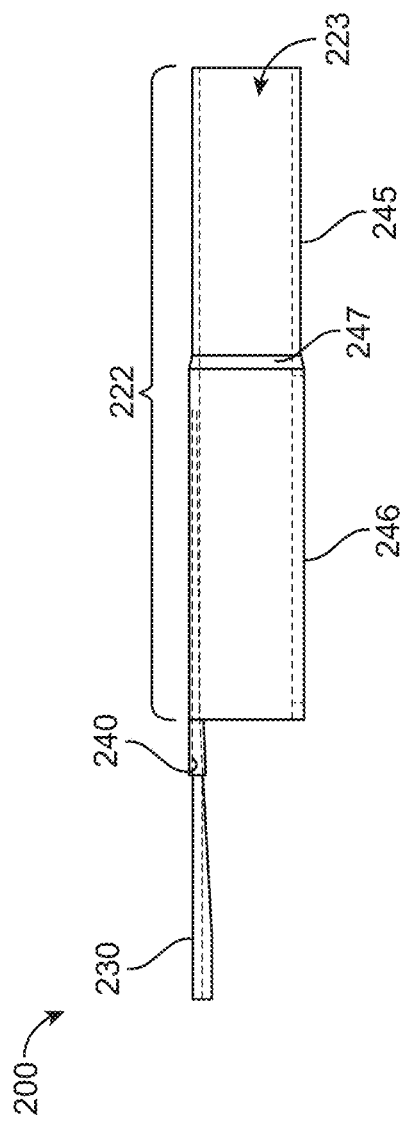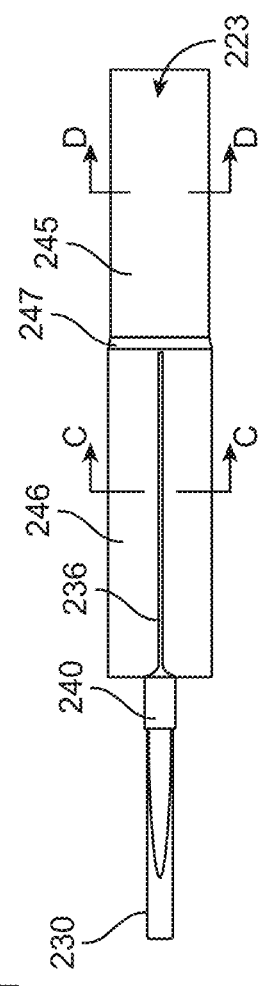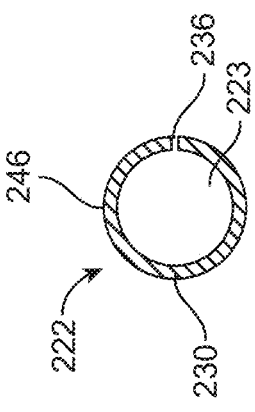

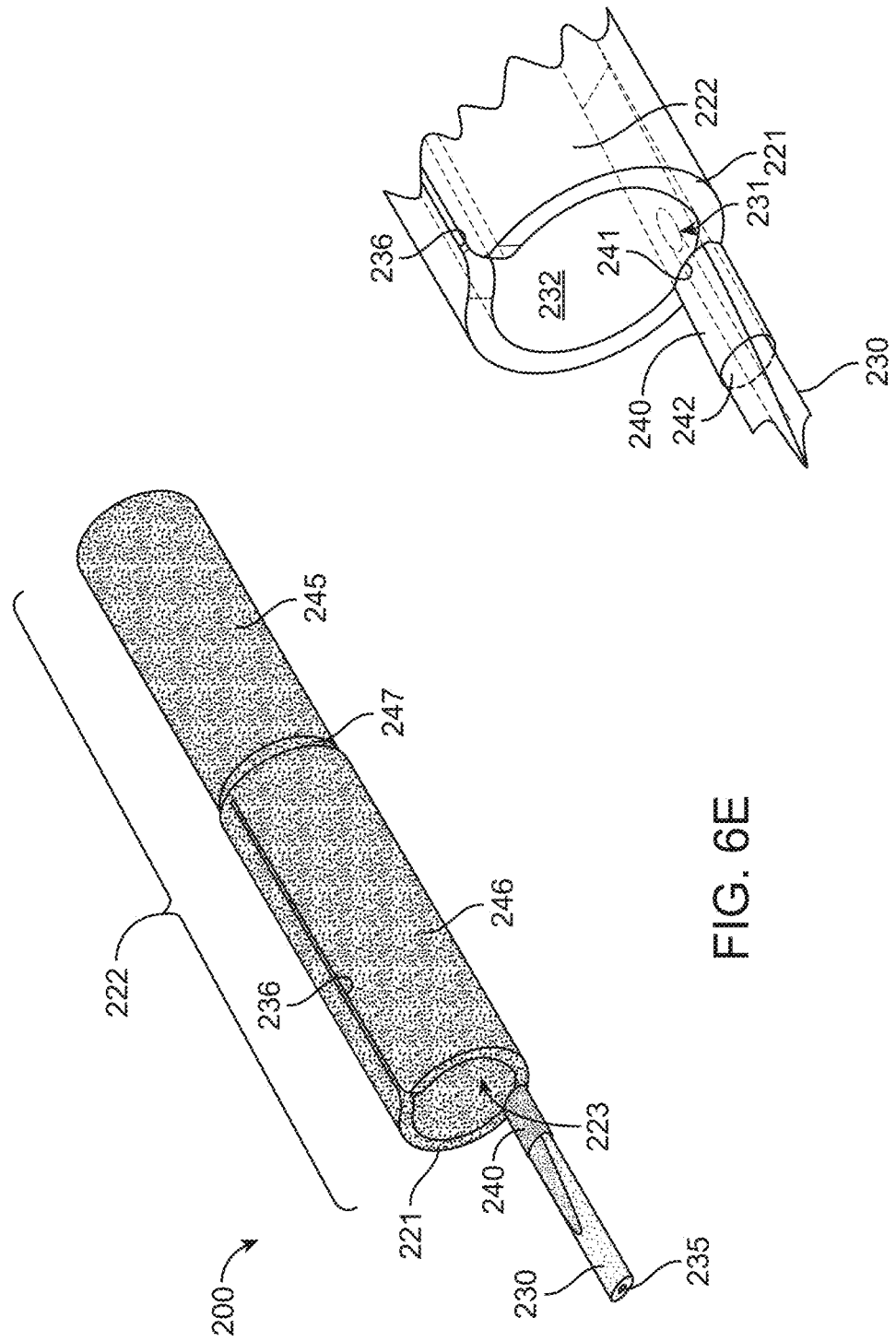

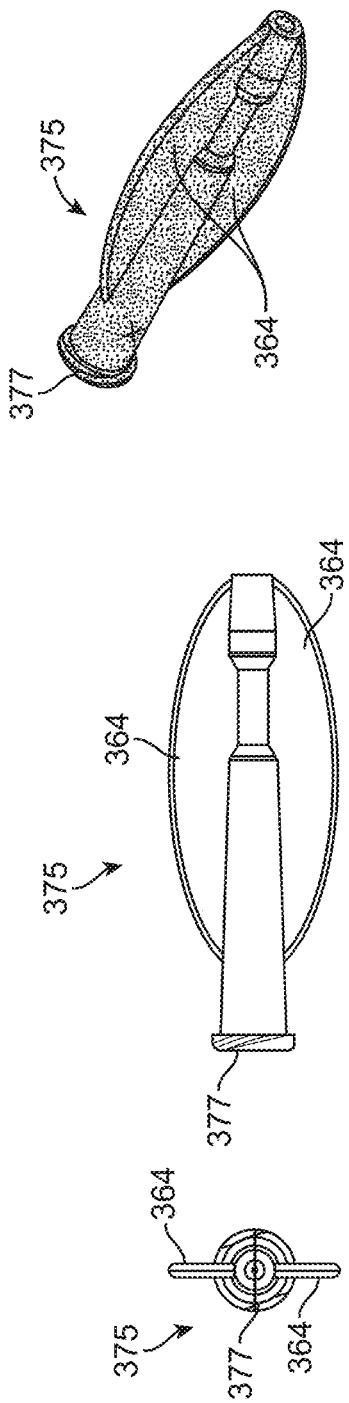
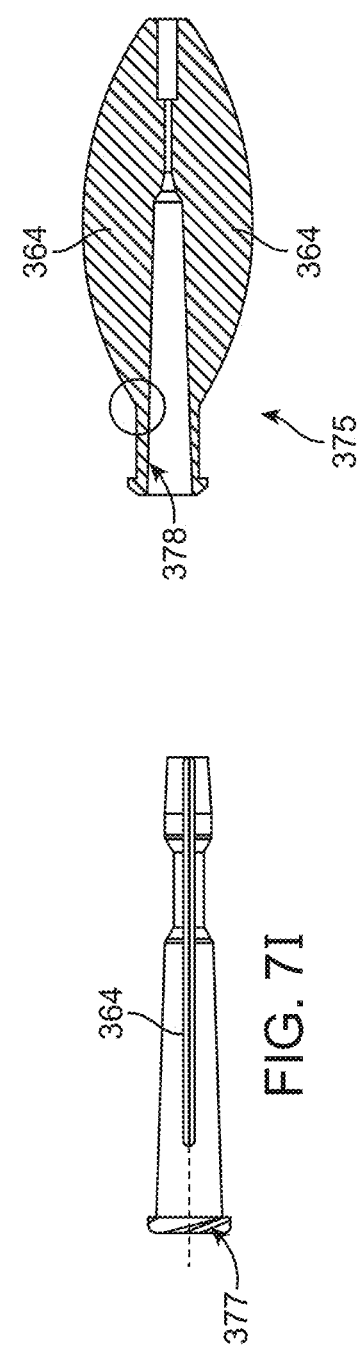

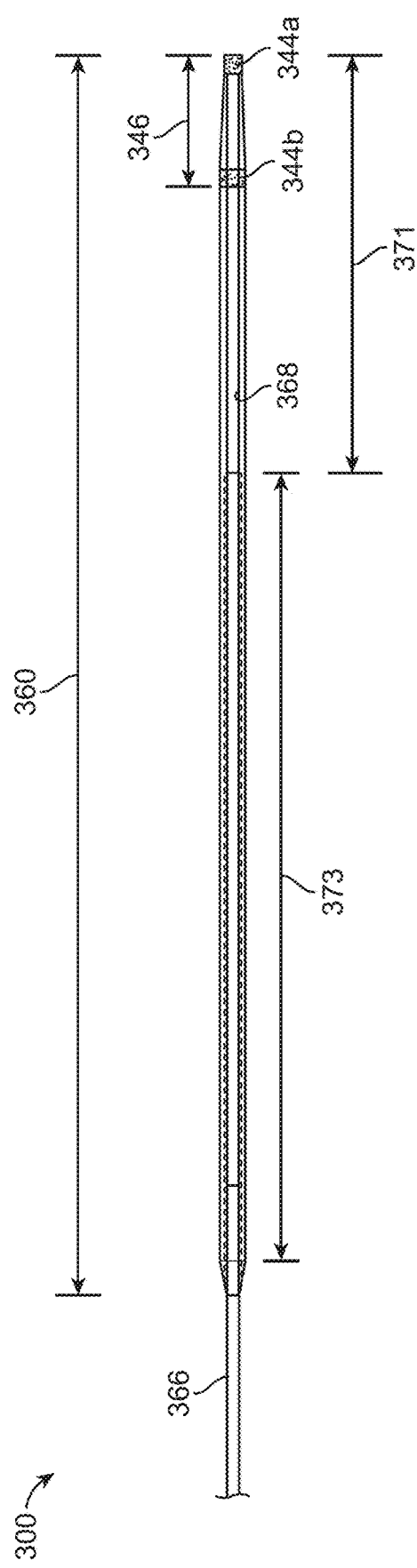
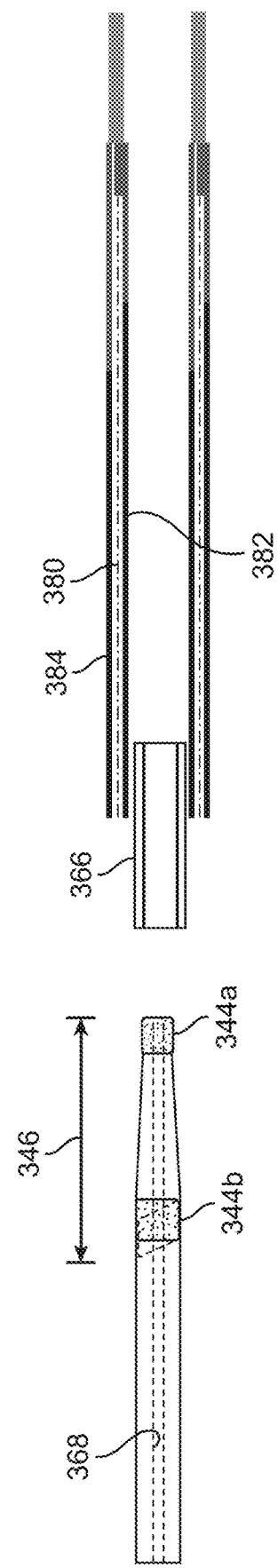
FIG. 10A
FIG. 10B
FIG. 10C

ASPIRATION CATHETER SYSTEMS AND METHODS OF USE

CROSS-REFERENCE TO RELATED APPLICATIONS

This application is continuation-in-part of co-pending U.S. patent application Ser. No. 15/866,012, filed on Jan. 9, 2018, which claims the benefit of priority under 35 U.S.C. § 119(e) to U.S. Provisional Patent Application Ser. No. 62/444,584, filed Jan. 10, 2017, and 62/607,510, filed Dec. 19, 2017.

This application is also a continuation-in-part of co-pending U.S. patent application Ser. No. 15/727,373 filed Oct. 6, 2017, which is a continuation of U.S. application Ser. No. 15/217,810, filed Jul. 22, 2016, now U.S. Pat. No. 10,426,497, issued Oct. 1, 2019, which claims the benefit of priority to U.S. Provisional Application Nos. 62/196,613, filed Jul. 24, 2015, and 62/275,939, filed Jan. 7, 2016, and 62/301,857, filed Mar. 1, 2016.

This application is also a continuation-in-part of co-pending U.S. patent application Ser. No. 16/584,351, filed Sep. 26, 2019, which is a continuation of U.S. patent application Ser. No. 15/875,214, filed Jan. 19, 2018, which claims the benefit of priority under 35 U.S.C. § 119(e) to U.S. Provisional Patent Application Ser. Nos. 62/448,678, filed Jan. 20, 2017, and 62/517,005, filed Jun. 8, 2017.

This application is also a continuation-in-part of co-pending U.S. patent application Ser. No. 16/543,215, filed Aug. 16, 2019, which is continuation of U.S. patent application Ser. No. 15/856,979, filed Dec. 28, 2017, now U.S. Pat. No. 10,456,555, issued Oct. 29, 2019, which is a continuation of U.S. application Ser. No. 15/805,673, filed Nov. 7, 2017, now U.S. Pat. No. 10,485,952, issued Nov. 26, 2019, which is a continuation of U.S. patent application Ser. No. 15/015,799, filed Feb. 4, 2016, now U.S. Pat. No. 9,820,761, issued Nov. 21, 2017, which claims priority to U.S. Provisional Application Ser. No. 62/111,481, filed Feb. 4, 2015, and U.S. Provisional Application Ser. No. 62/142,637, filed Apr. 3, 2015.

The disclosures are each incorporated by reference in their entireties.

FIELD

The present technology relates generally to medical devices and methods, and more particularly, to aspiration catheter systems and their methods of use.

BACKGROUND

Acute ischemic stroke (AIS) usually occurs when an artery to the brain is occluded, preventing delivery of fresh oxygenated blood from the heart and lungs to the brain. These occlusions are typically caused by a thrombus or an embolus lodging in the artery and blocking the artery that feeds a territory of brain tissue. If an artery is blocked, ischemia injury follows, and brain cells may stop working. Furthermore, if the artery remains blocked for more than a few minutes, the brain cells may die, leading to permanent neurological deficit or death. Therefore, immediate treatment is critical.

Two principal therapies are employed for treating ischemic stroke: thrombolytic therapy and endovascular treatment. The most common treatment used to reestablish flow or re-perfuse the stroke territory is the use of intravenous (IV) thrombolytic therapy. The timeframe to enact thrombolytic therapy is within 3 hours of symptom onset for IV infusion (4.5 hours in selected patients) or within 6 hours for site-directed intra-arterial infusion. Instituting therapy at later times has no proven benefit and may expose the patient to greater risk of bleeding due to the thrombolytic effect. Endovascular treatment most commonly uses a set of tools to mechanically remove the embolus, with our without the use of thrombolytic therapy.

The gamut of endovascular treatments include mechanical embolectomy, which utilizes a retrievable structure, e.g., a coil-tipped retrievable stent (also known as a "stent retriever" or a STENTRIEVER), a woven wire stent, or a laser cut stent with struts that can be opened within a clot in the cerebral anatomy to engage the clot with the stent struts, create a channel in the emboli to restore a certain amount of blood flow, and to subsequently retrieve the retrievable structure by pulling it out of the anatomy, along with aspiration techniques. Other endovascular techniques to mechanically remove AIS-associated embolus include Manual Aspiration Thrombectomy (MAT) (also known as the "ADAPT" technique). ADAPT/MAT is an endovascular procedure where large bore catheters are inserted through the transfemoral artery and maneuvered through complex anatomy to the level of the embolus, which may be in the extracranial carotids, vertebral arteries, or intracranial arteries. Aspiration techniques may be used to remove the embolus through the large bore catheters. Another endovascular procedure is Stentriever-Mediated Manual Aspiration Thrombectomy (SMAT) (similar to the Stentriever-assisted "Solumbra" technique). SMAT, like MAT, involves accessing the embolus through the transfemoral artery. After access is achieved, however, a retrievable structure is utilized to pull the embolus back into a large bore catheter.

To access the cerebral anatomy, guide catheters or guide sheaths are used to guide interventional devices to the target anatomy from an arterial access site, typically the femoral artery. The length of the guide is determined by the distance between the access site and the desired location of the guide distal tip. Interventional devices such as guidewires, microcatheters, and intermediate catheters used for sub-selective guides and aspiration, are inserted through the guide and advanced to the target site. Often, devices are used in a co-axial fashion, namely, a guidewire inside a microcatheter inside an intermediate catheter is advanced as an assembly to the target site in a stepwise fashion with the inner, most atraumatic elements, advancing distally first and providing support for advancement of the outer elements. The length of each element of the coaxial assemblage takes into account the length of the guide, the length of proximal connectors on the catheters, and the length needed to extend from the distal end.

Typical tri-axial systems such as for aspiration or delivery of stent retrievers and other interventional devices require overlapped series of catheters, each with their own rotating hemostatic valves (RHV) on the proximal end. For example, a guidewire can be inserted through a Penumbra Velocity microcatheter having a first proximal RHV, which can be inserted through a Penumbra ACE68 having a second proximal RHV, which can be inserted through a Penumbra NeuronMAX 088 access catheter having a third proximal RHV positioned in the high carotid via a femoral introducer. Maintaining the coaxial relationships between these catheters can be technically challenging. The three RHVs must be constantly adjusted with two hands or, more commonly, four hands (i.e. two operators). Further, the working area of typical tri-axial systems for aspiration and/or intracranial device delivery can require working area of 3-5 feet at the base of the operating table.

The time required to access the site of the occlusion and restore, even partially, flow to the vessel is crucial in determining a successful outcome of such procedures. Similarly, the occurrence of distal emboli during the procedure and the potentially negative neurologic effect and procedural complications such as perforation and intracerebral hemorrhage are limits to success of the procedure. There is a need for a system of devices and methods that allow for rapid access, optimized catheter aspiration, and treatment to fully restore flow to the blocked cerebral vessel.

SUMMARY

In an aspect, described is an intravascular catheter advancement device for advancing a catheter within the neurovasculature. The catheter advancement device includes a flexible elongate body having a proximal end, a distal end, and a single lumen extending therebetween. The flexible elongate body includes a proximal segment having a hypotube coated with a polymer; an intermediate segment having an unreinforced polymer having a durometer of no more than 72 D; and a tip segment. The tip segment is formed of a polymer different from the intermediate segment and has a durometer of no more than about 35 D and a length of at least 5 cm. The tip segment has a tapered portion which tapers distally from a first outer diameter to a second outer diameter over a length of between 1 and 3 cm. The catheter advancement device has a length configured to extend from outside the patient's body, through the femoral artery, and to the petrous portion of the internal carotid artery and an inner diameter less than 0.024 inches to accommodate a guidewire.

The flexible elongate body can be formed without a tubular inner liner. The unreinforced polymer of the flexible elongate body can incorporate a lubricious additive. A taper angle of the wall of the tapered portion relative to a center line of the tapered portion can be between 0.9 to 1.6 degrees (or 2-3 degrees). The second outer diameter can be about ½ of the first outer diameter. The second outer diameter can be about 40% of the first outer diameter. The second outer diameter can be about 65% of the first outer diameter. The intermediate segment can include a first segment having a material hardness of no more than 55 D and a second segment located proximal to the first segment having a material hardness of no more than 72 D.

The catheter advancement device can be part of a system including a catheter having a lumen and a distal end. An outer diameter of the flexible elongate body can be sized to be positioned coaxially within the catheter lumen such that the tapered portion of the tip segment extends distally beyond the distal end of the catheter to aid in delivery of the catheter to an intracranial vessel.

The flexible elongate body can have an insert length that is at least about 49 cm. A location of a material transition between the unreinforced polymer and the hypotube can be at least about 49 cm from the distal end of the flexible elongate body. The location can allow for positioning the material transition proximal to the brachiocephalic take-off in the aortic arch when the distal end is positioned within the petrous portion of the internal carotid artery. The hypotube can have an inner diameter of about 0.021" and an outer diameter of about 0.027". The first outer diameter can be about 0.062" up to about 0.080". The second outer diameter can be about 0.031". The tip segment can include a first radiopaque marker and a second radiopaque marker. The first radiopaque marker can be positioned on the first outer diameter and identify a border between the first outer diameter and the tapered portion. The second radiopaque marker can be positioned on the second outer diameter. The first and second radiopaque markers can have different widths. The first and second radiopaque markers can be extruded polymer loaded with a radiopaque material, the radiopaque material being platinum/iridium, tungsten, or tantalum.

The catheter advancement device can be configured for insertion over the guidewire such that the guidewire extends through the single lumen from the proximal end to the distal end. The proximal end can have a proximal opening and the distal end can have a distal opening, the proximal and distal openings sized to receive the guidewire. The catheter advancement device can further include a rapid exchange opening through a wall. The hypotube can be coated with a lubricious polymer. The lubricious polymer can be PTFE. The hypotube can be circular, oval, or trapezoidal D shape in cross-section. The hypotube can be a skived hypotube of stainless steel. The skived hypotube can be coupled to a proximal hub. The proximal hub can include a luer thread and a luer taper inside of the hub. The proximal hub can prevent insertion of the proximal hub through a proximal RHV.

In an aspect, described is an intravascular catheter advancement device for facilitation of intraluminal medical procedures within the neurovasculature. The catheter advancement device includes a flexible elongate body having a proximal end region, an outer diameter, a tapered distal tip portion, a distal opening, and a single lumen extending longitudinally through the flexible elongate body to the distal opening; and a proximal portion coupled to the proximal end region of the flexible elongate body. The proximal portion extends proximally to a proximal-most end of the catheter advancement element. A hardness of the flexible elongate body transitions proximally towards increasingly harder materials up to the proximal portion forming a first plurality of material transitions. At least a portion of the flexible elongate body is formed of a plurality of layers including a reinforcement layer. The outer diameter of the flexible elongate body is sized to be positioned coaxially within a lumen of a catheter such that the distal tip portion of the flexible elongate body extends distally beyond a distal end of the catheter to aid in delivery of the catheter to an intracranial vessel.

The reinforcement layer can be a braid. The braid can extend from the proximal end region of the flexible elongate body and terminate at a point proximal to the distal tip portion. The point can be located between 4 cm and 15 cm from a distal-most terminus of the flexible elongate body. The plurality of layers can further include a first polymer material layer and a second polymer material layer. The braid can be positioned between the first and second polymer material layers. The proximal portion can be a hypotube having a distal end coupled to the flexible elongate body. The braid can be positioned between the first and second polymer material layers and positioned over the distal end of the hypotube.

The distal tip portion can include a material having a material hardness that is no more than 35 D. The proximal end region of the elongate body can include a material having a material hardness that is between 55 D to 72 D. The elongate body can include a first segment including the distal tip portion having a hardness of no more than 35 D. The elongate body can include a second segment located proximal to the first segment having a hardness of no more than 55 D. The elongate body can include a third segment located proximal to the second segment having a hardness of no more than 72 D. The proximal portion can couple to the elongate body within the third segment. The first segment can be unreinforced and the third segment can be reinforced. The second segment can be at least partially reinforced. A reinforcement braid can extend through at least the third segment. The first, second, and third segments can combine to form an insert length of the elongate body. The first segment can have a length of about 4 cm to about 12.5 cm. The second segment can have a length of about 5 cm to about 8 cm. The third segment can have a length of about 25 cm to about 35 cm.

The system can further include the catheter having the lumen and the distal end. The catheter can include a flexible distal luminal portion having a proximal end, a proximal end region, and a proximal opening. The lumen can extend between the proximal end and the distal end. The catheter can further include a proximal extension extending proximally from a point of attachment adjacent the proximal opening. The proximal extension can be less flexible than the flexible distal luminal portion and can be configured to control movement of the catheter. The proximal extension can have an outer diameter at the point of attachment that is smaller than an outer diameter of the distal luminal portion at the point of attachment. A material hardness of the flexible distal luminal portion can transition proximally towards increasingly harder materials up to the proximal extension. The flexible distal luminal portion can include a second plurality of material transitions. The flexible elongate body can be coaxially positioned within the lumen of the catheter such that the distal tip portion of the flexible elongate body extends distally beyond the distal end of the catheter such that the first plurality of material transitions of the flexible elongate body are staggered relative to and do not overlap with the second plurality of material transitions of the flexible distal luminal portion.

The catheter can be packaged with the device coaxially positioned within the lumen of the catheter such that the proximal portion of the flexible elongate body is locked with the proximal extension of the catheter. At least a portion of the proximal extension of the catheter can be color-coded.

The single lumen of the flexible elongate body can be sized to accommodate a guidewire. The flexible elongate body can include a proximal opening sized to accommodate the guidewire. The proximal opening can be located within the proximal end region of the flexible elongate body. The proximal opening can be through a sidewall of the flexible elongate body and located a distance distal to the proximal portion coupled to the proximal end region. The distance can be about 10 cm from the distal tip portion up to about 20 cm from the distal tip portion. The proximal portion can have an outer diameter that is smaller than the outer diameter of the flexible elongate body. The proximal portion can be a hypotube. The device can be configured to be advanced together with the catheter after the distal end of the catheter is distal to the petrous portion of the internal carotid artery.

In an interrelated aspect, disclosed is a method of performing a medical procedure in a cerebral vessel of a patient including inserting an assembled coaxial catheter system into a blood vessel of a patient. The assembled coaxial catheter system includes a catheter and a catheter advancement element. The catheter includes a flexible distal luminal portion having a proximal end, a proximal end region, a proximal opening, a distal end, and a lumen extending between the proximal end and the distal end; and a proximal extension extending proximally from a point of attachment adjacent the proximal opening. The proximal extension is less flexible than the flexible distal luminal portion and is configured to control movement of the catheter. The proximal extension has an outer diameter at the point of attachment that is smaller than an outer diameter of the distal luminal portion at the point of attachment. The catheter advancement element includes a flexible elongate body having a proximal end region, an outer diameter, a tapered distal tip portion, a distal opening, and a single lumen extending longitudinally through the flexible elongate body to the distal opening; and a proximal portion extending proximally from the proximal end region to a proximal-most end of the catheter advancement element. When assembled, the catheter advancement element extends through the catheter lumen and the tapered distal tip portion extends distal to the distal end of the distal luminal portion. The method further includes advancing the assembled catheter system until the distal end of the distal luminal portion reaches a target site within the cerebral vessel and the point of attachment between the distal luminal portion and the proximal extension is positioned proximal to the brachiocephalic take-off in the aortic arch. The method further includes removing the catheter advancement element from the lumen of the catheter; and removing occlusive material while applying a negative pressure to the lumen of the catheter.

The distal end of the distal luminal portion can be positioned distal to the carotid siphon when the point of attachment is positioned proximal to the brachiocephalic take-off within the aortic arch. The distal luminal portion can have a length between 35 cm and 60 cm. The proximal portion of the catheter advancement element can be coupled to the proximal end region of the flexible elongate body at a point of attachment, the proximal portion extending proximally from the point of attachment to the proximal-most end of the catheter advancement element. The proximal portion can have a single lumen extending through an entire length of the proximal portion that communicates with the single lumen of the elongate body. The elongate body can have a length sufficient to allow the point of attachment between the elongate body and the proximal portion to remain within or proximal to the aortic arch when assembled with the catheter. The distal end of the catheter can be positioned near the target site within the cerebral vessel.

The assembled catheter system can be pre-packaged with the catheter advancement element coaxially positioned within the lumen of the distal luminal portion such that the proximal portion of the flexible elongate body is locked with the proximal extension of the catheter. At least a portion of the proximal extension of the catheter can be color-coded. The single lumen of the flexible elongate body can be sized to accommodate a guidewire. The flexible elongate body can include a proximal opening sized to accommodate the guidewire. The proximal opening can be located within the proximal end region of the flexible elongate body. The proximal opening can be through a sidewall of the flexible elongate body and can be located a distance distal to the proximal portion coupled to the proximal end region. The distance can be about 10 cm from the distal tip portion up to about 20 cm from the distal tip portion. A hardness of the flexible elongate body can transition proximally towards increasingly harder materials up to the proximal portion forming a first plurality of material transitions. At least a portion of the flexible elongate body can be formed of a plurality of layers including a reinforcement layer. The reinforcement layer can be a braid. The braid can extend from the proximal end region of the flexible elongate body and terminate at a point proximal to the distal tip portion. The point can be located between 4 cm and 15 cm from a distal-most terminus of the flexible elongate body. The plurality of layers can further include a first polymer material layer and a second polymer material layer. The braid can be positioned between the first and second polymer material layers. The proximal portion can be a hypotube having a distal end coupled to the flexible elongate body. The braid positioned between the first and second polymer material layers is positioned over the distal end of the hypotube.

The distal tip portion can include a material having a material hardness that is no more than 35 D. The proximal end region of the elongate body can include a material having a material hardness that is between 55 D to 72 D. The elongate body can include a first segment including the distal tip portion having a hardness of no more than 35 D. The elongate body can include a second segment located proximal to the first segment having a hardness of no more than 55 D. The elongate body can include a third segment located proximal to the second segment having a hardness of no more than 72 D. The proximal portion can couple to the elongate body within the third segment. The first segment can be unreinforced and the third segment can be reinforced. The second segment can be at least partially reinforced. A reinforcement braid can extend through at least the third segment. The first, second, and third segments can combine to form an insert length of the elongate body. The first segment can have a length of about 4 cm to about 12.5 cm. The second segment can have a length of about 5 cm to about 8 cm. The third segment can have a length of about 25 cm to about 35 cm. A material hardness of the flexible distal luminal portion can transition proximally towards increasingly harder materials up to the proximal extension. The flexible distal luminal portion can include a second plurality of material transitions. The flexible elongate body can be coaxially positioned within the lumen of the catheter such that the distal tip portion of the flexible elongate body extends distally beyond the distal end of the catheter such that the first plurality of material transitions of the flexible elongate body are staggered relative to and do not overlap with the second plurality of material transitions of the flexible distal luminal portion.

In an interrelated aspect, described is a method of performing a medical procedure in a cerebral vessel of a patient including inserting a guide sheath into a blood vessel. The guide sheath include a lumen extending between a proximal end region and a distal end region of the guide sheath, the distal end region of the guide sheath having an opening in communication with the lumen of the guide sheath. The method includes positioning the guide sheath such that the distal end region of the guide sheath is positioned within at least to a level of the common carotid artery. The method includes inserting an intermediate catheter through the lumen of the guide sheath. The intermediate catheter includes a lumen and a distal opening at a distal end of the intermediate catheter. The method includes advancing the intermediate catheter such that the distal end of the intermediate catheter is advanced through the opening of the guide sheath and beyond the distal end region of the guide sheath. The method includes inserting a distal access catheter through the lumen of the intermediate catheter. The distal access catheter includes a flexible distal luminal portion having a proximal end, a proximal end region, a proximal opening, a distal end, and a lumen extending between the proximal end and the distal end; and a proximal extension extending proximally from a point of attachment adjacent the proximal opening. The proximal extension is less flexible than the flexible distal luminal portion and is configured to control movement of the catheter. The proximal extension has an outer diameter at the point of attachment that is smaller than an outer diameter of the flexible distal luminal portion at the point of attachment. The method further includes advancing the distal access catheter such that the distal end of the flexible distal luminal portion is advanced through the distal opening of the intermediate catheter and beyond the distal end of the intermediate catheter.

The distal end region of the guide sheath can include an inflatable occlusion balloon. The method can further include inflating the occlusion balloon to occlude antegrade flow through the common carotid artery. The distal end region of the guide sheath can have an unlined, unreinforced region configured to seal onto an outer surface of the intermediate catheter. The distal access catheter can be assembled with a catheter advancement element forming an assembled coaxial catheter system prior to the advancing step. The catheter advancement element includes a flexible elongate body having a proximal end region, an outer diameter, a tapered distal tip portion, a distal opening, and a single lumen extending longitudinally through the flexible elongate body to the distal opening; and a proximal portion extending proximally from the proximal end region to a proximal-most end of the catheter advancement element.

When assembled, the catheter advancement element can extend through the lumen of the distal luminal portion and the tapered distal tip portion can extend distal to the distal end of the distal luminal portion. The method can further include advancing the assembled coaxial catheter system until the distal end of the distal luminal portion reaches a target site within the cerebral vessel and the point of attachment between the distal luminal portion and the proximal extension is positioned proximal to the brachiocephalic take-off in the aortic arch. The method can further include removing the catheter advancement element from the lumen of the catheter; and removing occlusive material while applying a negative pressure to the lumen of the catheter.

The assembled catheter system can be pre-packaged with the catheter advancement element coaxially positioned within the lumen of the distal luminal portion such that the proximal portion of the flexible elongate body is locked with the proximal extension of the catheter. At least one of the intermediate catheter and the distal access catheter can further include a tab to prevent over-insertion of the catheter relative to the lumen through which it extends. At least one of the intermediate catheter and the distal access catheter can further include a distinguishable color-coded element. The single lumen of the flexible elongate body can be sized to accommodate a guidewire. The flexible elongate body can include a proximal opening sized to accommodate the guidewire. The proximal opening can be located within the proximal end region of the flexible elongate body. The proximal opening can be through a sidewall of the flexible elongate body and can be located a distance distal to the proximal portion coupled to the proximal end region. The distance can be about 10 cm from the distal tip portion up to about 20 cm from the distal tip portion.

The intermediate catheter can be assembled with a catheter advancement element forming an assembled coaxial catheter system prior to the advancing step. The catheter advancement element can include a flexible elongate body having a proximal end region, an outer diameter, a tapered distal tip portion, a distal opening, and a single lumen extending longitudinally through the flexible elongate body to the distal opening; and a proximal portion extending proximally from the proximal end region to a proximal-most end of the catheter advancement element. When assembled, the catheter advancement element can extend through the lumen of the intermediate catheter and the tapered distal tip portion can extend distal to the distal end of the intermediate catheter. The intermediate catheter can include a flexible distal luminal portion and a proximal extension extending proximally from a point of attachment adjacent a proximal opening in the flexible distal luminal portion. The proximal extension can be less flexible than the flexible distal luminal portion of the intermediate catheter and have an outer diameter that is smaller than an outer diameter of the proximal elongate body.

In some variations, one or more of the following can optionally be included in any feasible combination in the above methods, apparatus, devices, and systems. More details of the devices, systems, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively, but are intended to be illustrative. Also, relative placement of features and elements may be modified for the purpose of illustrative clarity.

FIG. 4A is a cross-sectional view of first implementation of a proximal extension of a catheter;

FIG. 4B is a cross-sectional view of another implementation of a proximal extension of a catheter;

FIG. 4C is a cross-sectional view of the proximal extension of FIG. 4A within a working lumen of an access sheath;

FIG. 4D is a cross-sectional view of the proximal extension of FIG. 4B within a working lumen of an access sheath having a catheter advancement element extending therethrough;

FIG. 4E is a cross-sectional, schematic view comparing the surface area of the proximal extension of FIG. 4A and the proximal extension of FIG. 4B within the working lumen of an access sheath of FIG. 4D;

FIG. 5A is a side elevational view of an implementation of a catheter;

FIG. 5B is a top plan view of the catheter of FIG. 5A;

FIG. 5C is a cross-sectional view of the catheter taken along line C-C of FIG. 5B;

FIG. 5D is a cross-sectional view of the catheter taken along line D-D of FIG. 5B;

FIGS. 5E-5F are partial perspective views of the catheter of FIG. 5A;

FIG. 6A is a side elevational view of an implementation of a catheter;

FIG. 6B is a top plan view of the catheter of FIG. 6A;

FIG. 6C is a cross-sectional view of the catheter taken along line C-C of FIG. 6B;

FIG. 6D is a cross-sectional view of the catheter taken along line D-D of FIG. 6B;

FIGS. 6E-6F are partial perspective views of the catheter of FIG. 6A;

FIGS. 7F-7J are various views of an implementation of a proximal hub for coupling to the proximal portion shown in FIG. 7E;

FIG. 10A is a schematic cross-sectional view of an implementation of a catheter advancement element;

FIG. 10B is a schematic cross-sectional view of a distal end region of the catheter advancement element of FIG. 10A;

FIG. 10C is a schematic cross-sectional view of a middle region of the catheter advancement element of FIG. 10A;

It should be appreciated that the drawings are for example only and are not meant to be to scale. It is to be understood that devices described herein may include features not necessarily depicted in each figure.

DETAILED DESCRIPTION

Figure 1A:
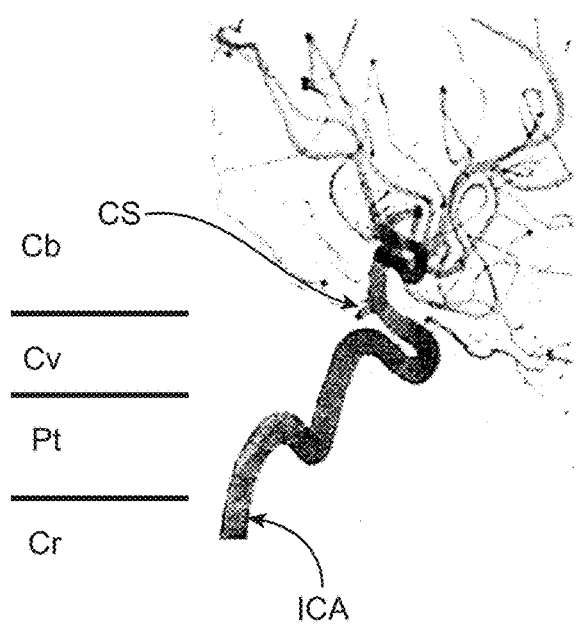
FIGS. 1A-1B illustrate the course of the terminal internal carotid artery through to the cerebral vasculature.

Navigating the carotid anatomy in order to treat various neurovascular pathologies at the level of the cerebral arteries, such as acute ischemic stroke (AIS), requires catheter systems having superior flexibility and deliverability. The internal carotid artery (ICA) arises from the bifurcation of the common carotid artery (CCA) at the level of the intervertebral disc between C3 and C4 vertebrae. As shown in FIG. 1A, the course of the ICA is divided into four parts—cervical Cr, petrous Pt, cavernous Cv and cerebral Cb parts. In the anterior circulation, the consistent tortuous terminal carotid is locked into its position by bony elements. The cervical carotid Cr enters the petrous bone and is locked into a set of turns as it is encased in bone. The cavernous carotid is an artery that passes through a venous bed, the cavernous sinus, and while flexible, is locked as it exits the cavernous sinus by another bony element, which surrounds and fixes the entry into the cranial cavity. Because of these bony points of fixation, the petrous and cavernous carotid (Pt and Cv) and above are relatively consistent in their tortuosity. The carotid siphon CS is an S-shaped part of the terminal ICA. The carotid siphon CS begins at the posterior bend of the cavernous ICA and ends at the ICA bifurcation into the anterior cerebral artery ACA and middle cerebral artery MCA. The ophthalmic artery arises from the cerebral ICA, which represents a common point of catheter hang-up in accessing the anterior circulation. The MCA is initially defined by a single M1 segment and then further bifurcates in two or three M2 segments and then further arborizes to create M3 segments. These points of catheter hang up can significantly increase the amount of time needed to restore blood perfusion to the brain, which in the treatment of AIS is a disadvantage with severe consequences.

With advancing age, the large vessels often enlarge and lengthen. Fixed proximally and distally, the cervical internal carotid artery often becomes tortuous with age. The common carotid artery CCA is relatively fixed in the thoracic cavity as it exits into the cervical area by the clavicle. The external and internal carotid arteries ECA, ICA are not fixed relative to the common carotid artery CCA, and thus they develop tortuosity with advancing age with lengthening of the entire carotid system. This can cause them to elongate and develop kinks and tortuosity or, in worst case, a complete loop or so-called "cervical loop". If catheters used to cross these kinked or curved areas are too stiff or inflexible, these areas can undergo a straightening that can cause the vessel to wrap around or "barbershop pole" causing focused kinking and folding of the vessel. These sorts of extreme tortuosity also can significantly increase the amount of time needed to restore blood perfusion to the brain, particularly in the aging population. In certain circumstances, the twisting of vessels upon themselves or if the untwisted artery is kinked, normal antegrade flow may be reduced to a standstill creating ischemia. Managing the unkinking or unlooping the vessels such as the cervical ICA can also increase the time it takes to perform a procedure.

A major drawback of current catheter systems and methods for stroke intervention procedures is the amount of time required to restore blood perfusion to the brain, including the time it takes to access the occlusive site or sites in the cerebral artery and the time it takes to completely remove the occlusion in the artery. Because it is often the case that more than one attempt must be made to completely remove the occlusion, reducing the number of attempts as well as reducing the time required to exchange devices for additional attempts is an important factor in minimizing the overall time. Additionally, each attempt is associated with potential procedural risk due to device advancement in the delicate cerebral vasculature. Another limitation is the need for multiple operators to deliver and effectively manipulate long tri-axial systems with multiple RHVs typically used with conventional guide and distal access catheters.

Described herein are catheter systems for treating various neurovascular pathologies, such as acute ischemic stroke (AIS). The systems described herein provide quick and simple single-operator access to distal target anatomy, in particular tortuous anatomy of the cerebral vasculature at a single point of manipulation. The medical methods, devices and systems described herein allow for navigating complex, tortuous anatomy to perform rapid and safe aspiration and removal of cerebral occlusions for the treatment of acute ischemic stroke. The medical methods, devices and systems described herein can also be used to deliver intracranial medical devices, with or without aspiration for the removal of cerebral occlusions in the treatment of acute ischemic stroke. The systems described herein can be particularly useful for the treatment of AIS whether a user intends to perform stent retriever delivery alone, aspiration alone, or a combination of aspiration and stent retriever delivery as a frontline treatment for AIS. Further, the extreme flexibility and deliverability of the distal access catheter systems described herein allow the catheters to take the shape of the tortuous anatomy rather than exert straightening forces creating new anatomy. The distal access catheter systems described herein can pass through tortuous loops while maintaining the natural curves of the anatomy therein decreasing the risk of vessel straightening. The distal access catheter systems described herein can thereby create a safe conduit through the neurovasculature maintaining the natural tortuosity of the anatomy for other catheters to traverse (e.g. interventional device delivery catheters). The catheters traversing the conduit need not have the same degree of flexibility and deliverability such that if they were delivered directly to the same anatomy rather than through the conduit, would lead to straightening, kinking, or folding of the anterior circulation.

While some implementations are described herein with specific regard to accessing a neurovascular anatomy or delivery of treatment devices, the systems and methods described herein should not be limited to this and may also be applicable to other uses. For example, the catheter systems described herein may be used to deliver working devices to a target vessel of a coronary anatomy, peripheral anatomy, or other vasculature anatomy. Coronary vessels are considered herein including left and right coronary arteries, posterior descending artery, right marginal artery, left anterior descending artery, left circumflex artery, M1 and M2 left marginal arteries, and D1 and D2 diagonal branches. Any of a variety of peripheral vessels are considered herein including the popliteal arteries, anterior tibial arteries, dorsalis pedis artery, posterior tibial arteries, and fibular artery. It should also be appreciated that where the phrase "aspiration catheter" is used herein that such a catheter may be used for other purposes besides or in addition to aspiration, such as the delivery of fluids to a treatment site or as a support catheter or distal access catheter providing a conduit that facilitates and guides the delivery or exchange of other devices such as a guidewire or interventional devices, such as stent retrievers. Alternatively, the access systems described herein may also be useful for access to other parts of the body outside the vasculature. Similarly, where the working device is described as being an expandable cerebral treatment device, stent retriever or self-expanding stent other interventional devices can be delivered using the delivery systems described herein.

Figure 2A:
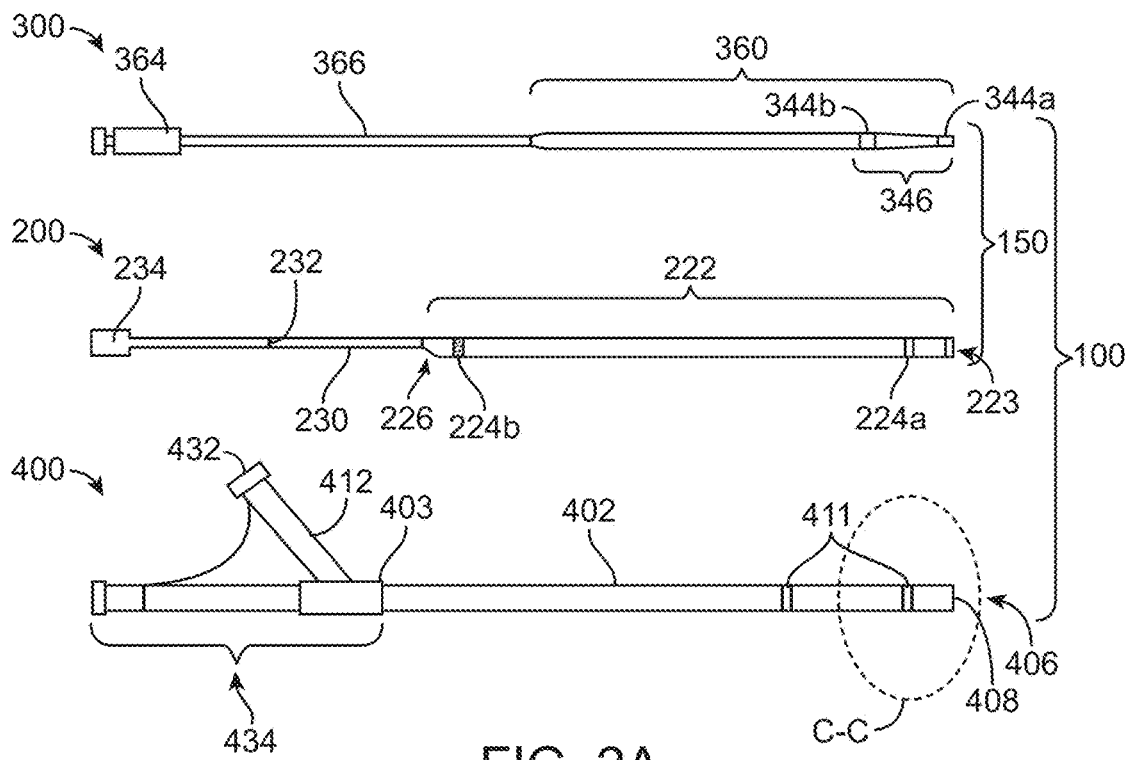
FIG. 2A is an exploded view of an implementation of an aspiration catheter system.
Figure 2B:
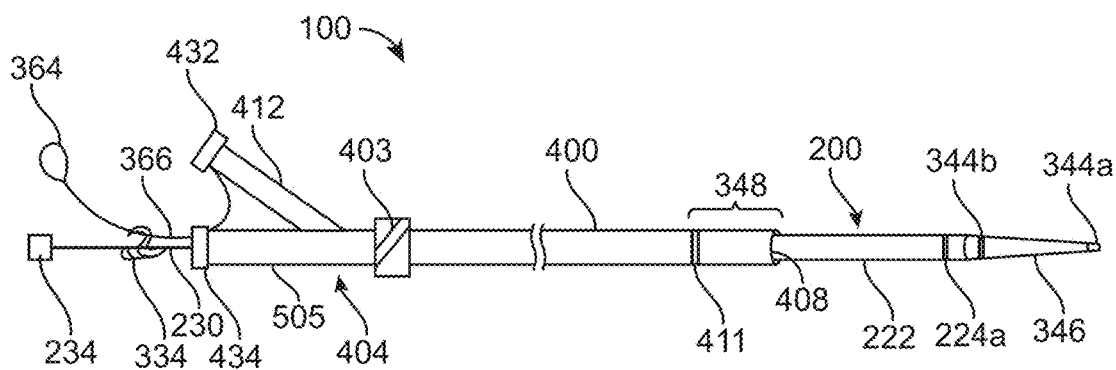
FIG. 2B is an assembled view of the system of FIG. 2A.

Referring now to the drawings, FIGS. 2A-2B illustrate a system 100 including devices for accessing and removing a cerebral occlusion to treat acute ischemic stroke from an access site. The system 100 can be a single operator system such that each of the components and systems can be delivered and used together by one operator through a single point of manipulation requiring minimal hand movements. As will be described in more detail below, all wire and catheter manipulations can occur at or in close proximity to a single rotating hemostatic valve (RHV) 434 or more than a single RHV co-located in the same device. The system 100 can include one or more of a catheter 200, a catheter advancement element 300, and an access guide sheath 400, each of which will be described in more detail below. The catheter 200 is configured to be received through the guide sheath 400 and is designed to have exceptional deliverability. The catheter 200 can be a spined, distal access catheter co-axial with a lumen of the guide sheath 400 thereby providing a step-up in inner diameter within the conduit. The catheter 200 can be delivered using a catheter advancement element 300 inserted through a lumen 223 of the catheter 200 forming a catheter delivery system 150. The system 100 can be a distal access system that can create a variable length from point of entry at the percutaneous arteriotomy (e.g. the femoral artery or other point of entry) to the target control point of the distal catheter. Conventional distal access systems for stroke intervention typically include a long guide sheath or guide catheter placed through a shorter "introducer" sheath (e.g. 11-30 cm in length) at the groin. The long guide sheath is typically positioned in the ICA to support neurovascular interventions including stroke embolectomy (sometimes referred to as "thrombectomy"). For added support, these can be advanced up to the bony terminal petrous and rarely into the cavernous or clinoid or supraclinoid terminal ICA when possible. To reach targets in the M1 or M2 distribution for ADAPT/MAT or Solumbra/SMAT approaches, an additional catheter may be inserted through the long guide catheter. These catheters are typically large-bore aspiration catheters that can be, for example 130 cm in length or longer. As will be described in more detail below, the distal access systems 100 described herein can be shorter, for example, only 115 cm in length when taken as a system as measured from the access point, typically the common femoral artery. Additionally, the single operator can use the systems described herein by inserting them through a single rotating hemostatic valve (RHV) 434 on the guide sheath 400 or more than one RHV co-located in the same device such as a dual-headed RHV. Thus, what was once a two-person procedure can be a one-person procedure.

Each of the various components of the various systems will now be described in more detail.

Access Guide Sheath

Now with respect to FIGS. 2A-2D, the distal access system 100 can include an access guide sheath 400 having a body 402 through which a working lumen extends from a proximal hemostasis valve 434 coupled to a proximal end region 403 of the body 402 to a distal opening 408 of a distal end region. The working lumen is configured to receive the catheter 200 therethrough such that a distal end of the catheter 200 can extend beyond a distal end of the sheath 400 through the distal opening 408. The guide sheath 400 can be used to deliver the catheters described herein as well as any of a variety of working devices known in the art. For example, the working devices can be configured to provide thrombotic treatments and can include large-bore catheters, aspiration embolectomy (or thrombectomy), advanced catheters, wires, balloons, retrievable structures such as coil-tipped retrievable stents "Stentriever" as well as permanent structures including flow diverters, and vessel support implants including balloon expandable stents, self-expanding stents, and mesh sleeves. The guide sheath 400 in combination with the catheter 200 can be used to apply distal aspiration as will be described in more detail below.

The guide sheath 400 can be any of a variety of commercially available guide sheaths. For example, the guide sheath 400 can have an ID between 0.087"-0.089" such as the Cook SHUTTLE 6 F (Cook Medical, Inc., Bloomington, Ind.), Terumo DESTINATION 6 F (Terumo Europe NV), Cordis VISTA BRITE TIP (Cordis Corp., Hialeah, Fla.), and Penumbra NEURON MAX 088 (Penumbra, Inc., Alameda, Calif.), or comparable commercially available guiding sheath. Generally, sheath sizes are described herein using the French (F) scale. For example, where a sheath is described as being 6 French, the inner diameter of that sheath is able to receive a catheter having a 6 F outer diameter, which is about 1.98 mm or 0.078". A catheter may be described herein as having a particular size in French to refer to the compatibility of its inner diameter to receive an outer diameter of another catheter. A catheter may also be described herein as having a particular size in French to refer to its outer diameter being compatible with another catheter having a particular inner diameter.

Again with respect to FIGS. 2A-2D, the catheter body 402 can extend from a proximal furcation or rotating hemostatic valve (RHV) 434 at a proximal end region 403 to a tip 406 at a distal end of the body 402. The proximal RHV 434 may include one or more lumens molded into a connector body to connect to the working lumen of the body 402 of the guide sheath 400. As described above, the working lumen can receive the catheter 200 and/or any of a variety of working devices for delivery to a target anatomy. The RHV 434 can be constructed of thick-walled polymer tubing or reinforced polymer tubing. The RHV 434 allows for the introduction of devices through the guide sheath 400 into the vasculature, while preventing or minimizing blood loss and preventing air introduction into the guide sheath 400. The RHV 434 can be integral to the guide sheath 400 or the guide sheath 400 can terminate on a proximal end in a female Luer adaptor to which a separate hemostasis valve component, such as a passive seal valve, a Tuohy-Borst valve or rotating hemostasis valve may be attached. The RHV 434 can have an adjustable opening that is open large enough to allow removal of devices that have adherent clot on the tip without causing the clot to dislodge at the RHV 434 during removal. Alternately, the RHV 434 can be removable such as when a device is being removed from the sheath 400 to prevent clot dislodgement at the RHV 434. The RHV 434 can be a dual RHV.

The RHV 434 can form a Y-connector on the proximal end 403 of the sheath 400 such that the first port of the RHV 434 can be used for insertion of a working catheter into the working lumen of the sheath 400 and a second port into arm 412 can be used for another purpose. For example, a syringe or other device can be connected at arm 412 via a connector 432 to deliver a forward drip, a flush line for contrast or saline injections through the body 402 toward the tip 406 and into the target anatomy. Arm 412 can also connect to a large-bore aspiration line and an aspiration source (not shown) such as a syringe or pump to draw suction through the working lumen. The aspiration source can be an active source of aspiration such as an aspiration pump, a regular or locking syringe, a hand-held aspirator, hospital suction, or the like, configured to draw suction through the working lumen. The aspiration source can be a locking syringe (for example a VacLok syringe) attached to a flow controller. The arm 412 can also allow the guide sheath 400 to be flushed with saline or radiopaque contrast during a procedure. The working lumen can extend from a distal end to a working proximal port of the proximal end region 403 of the catheter body 402.

The length of the catheter body 402 is configured to allow the distal tip 406 of the body 402 to be positioned as far distal in the internal carotid artery (ICA), for example, from a transfemoral approach with additional length providing for adjustments if needed. In some implementations (e.g. femoral or radial percutaneous access), the length of the body 402 can be in the range of 80 to 90 cm although the of the body 402 can be longer, for example, up to about 100 cm or up to about 105 cm or up to about 117 cm total. In implementations, the body 402 length is suitable for a transcarotid approach to the bifurcation of the carotid artery, in the range of 20-25 cm. In further implementations, the body 402 length is suitable for a percutaneous transcarotid approach to the CCA or proximal ICA, and is in the range of 10-15 cm. The body 402 is configured to assume and navigate the bends of the vasculature without kinking, collapsing, or causing vascular trauma, even, for example, when subjected to high aspiration forces. The point of insertion for the guide sheath 400 can vary including femoral, carotid, radial, brachial, ulnar, or subclavian arteries. The lengths of the body 402 described herein can be modified to accommodate different access points for the guide sheath 400. For example a body 402 of a guide sheath 400 for entry through the femoral artery near the groin may be longer than a body 402 of a guide sheath 400 for entry through the subclavian artery.

The tip 406 of the guide sheath 400 can have a same or similar outer diameter as a section of the body 402 leading up to the distal end. Accordingly, the tip 406 may have a distal face orthogonal to a longitudinal axis passing through the body 402 and the distal face may have an outer diameter substantially equal to a cross-sectional outer dimension of the body 402. In an implementation, the tip 406 includes a chamfer, fillet, or taper, making the distal face diameter slightly less than the cross-sectional dimension of the body 402. In a further implementation, the tip 406 may be an elongated tubular portion extending distal to a region of the body 402 having a uniform outer diameter such that the elongated tubular portion has a reduced diameter compared to the uniform outer diameter of the body 402. Thus, the tip 406 can be elongated or can be more bluntly shaped. Accordingly, the tip 406 may be configured to smoothly track through a vasculature and/or to dilate vascular restrictions as it tracks through the vasculature. The working lumen may have a distal end forming a distal opening 408.

The guide sheath 400 may include a tip 406 that tapers from a section of the body 402 leading up to the distal end. That is, an outer surface of the body 402 may have a diameter that reduces from a larger dimension to a smaller dimension at a distal end. For example, the tip 406 can taper from an outer diameter of approximately 0.114" to about 0.035" or from about 0.110" to about 0.035" or from about 0.106" to about 0.035". The angle of the taper of the tip 406 can vary depending on the length of the tapered tip 406. For example, in some implementations, the tip 406 tapers from 0.110" to 0.035" over a length of approximately 50 mm.

In an implementation, the guide sheath 400 includes one or more radiopaque markers 411. The radiopaque markers 411 can be disposed near the distal tip 406. For example, a pair of radiopaque bands may be swaged, painted, embedded, or otherwise disposed in or on the body 402. In some implementations, the radiopaque markers 411 include a barium polymer, tungsten polymer blend, tungsten-filled or platinum-filled marker that maintains flexibility of the distal end of the device and improves transition along the length of the guide sheath 400 and its resistance to kinking. In some implementations, the radiopaque marker 411 is a tungsten-loaded PEBAX or polyurethane that is heat welded to the body 402. The markers 411 are shown in the figures as rings around a circumference of one or more regions of the body 402. However, the markers 411 need not be rings and can have other shapes or create a variety of patterns that provide orientation to an operator regarding the position of the distal opening 408 within the vessel. Accordingly, an operator may visualize a location of the distal opening 408 under fluoroscopy to confirm that the distal opening 408 is directed toward a target anatomy where a catheter 200 is to be delivered. For example, radiopaque marker(s) 411 allow an operator to rotate the body 402 of the guide sheath 400 at an anatomical access point, e.g., a groin of a patient, such that the distal opening provides access to an ICA by subsequent working device(s), e.g., catheters and wires advanced to the ICA. In some implementations, the radiopaque marker(s) 411 include platinum, gold, tantalum, tungsten or any other substance visible under an x-ray fluoroscope. Any of the components of the systems described herein can incorporate radiopaque markers as described above.

In some implementations, the guide sheath 400 can have performance characteristics similar to other sheaths used in carotid access and AIS procedures in terms of kinkability, radiopacity, column strength, and flexibility. The inner liners can be constructed from a low friction polymer such as PTFE (polytetrafluoroethylene) or FEP (fluorinated ethylene propylene) to provide a smooth surface for the advancement of devices through the inner lumen. An outer jacket material can provide mechanical integrity to the inner liners and can be constructed from materials such as PEBAX, thermoplastic polyurethane, polyethylene, nylon, or the like. A third layer can be incorporated that can provide reinforcement between the inner liner and the outer jacket. The reinforcement layer can prevent flattening or kinking of the inner lumen of the body 402 to allow unimpeded device navigation through bends in the vasculature as well as aspiration or reverse flow. The body 402 can be circumferentially reinforced. The reinforcement layer can be made from metal such as stainless steel, Nitinol, Nitinol braid, helical ribbon, helical wire, cut stainless steel, or the like, or stiff polymer such as PEEK. The reinforcement layer can be a structure such as a coil or braid, or tubing that has been laser-cut or machine-cut so as to be flexible. In another implementation, the reinforcement layer can be a cut hypotube such as a Nitinol hypotube or cut rigid polymer, or the like. The outer jacket of the body 402 can be formed of increasingly softer materials towards the distal end. For example, proximal region of the body 402 can be formed of a material such as Nylon, a region of the body 402 distal to the proximal region of the body 402 can have a hardness of 72 D whereas areas more distal can be increasingly more flexible and formed of materials having a hardness of 55 D, 45 D, 35 D extending towards the distal tip 406, which can be formed of a material having a hardness of no more than 35 D and in some implementations softer than 35 D. The body 402 can include a hydrophilic coating.

The flexibility of the body 402 can vary over its length, with increasing flexibility towards the distal portion of the body 402. The variability in flexibility may be achieved in various ways. For example, the outer jacket may change in durometer and/or material at various sections. A lower durometer outer jacket material can be used in a distal section of the guide sheath compared to other sections of the guide sheath. Alternately, the wall thickness of the jacket material may be reduced, and/or the density of the reinforcement layer may be varied to increase the flexibility. For example, the pitch of the coil or braid may be stretched out, or the cut pattern in the tubing may be varied to be more flexible. Alternately, the reinforcement structure or the materials may change over the length of the elongate body 402. In another implementation, there is a transition section between the distal-most flexible section and the proximal section, with one or more sections of varying flexibilities between the distal-most section and the remainder of the elongate body 402. In this implementation, the distal-most section is about 2 cm to about 5 cm, the transition section is about 2 cm to about 10 cm and the proximal section takes up the remainder of the sheath length.

The different inner diameters of the guide sheaths 400 can be used to receive different outer diameter catheters 200. In some implementations, the working lumen of a first guide sheath 400 can have an inner diameter sized to receive a 6 F catheter and the working lumen of a second guide sheath 400 can have an inner diameter sized to receive an 8 F catheter. In some implementations, the distal region of the guide sheath 400 can have an inner diameter of about 0.087" to 0.088". The guide sheaths 400 can receive catheters having an outer diameter that is snug to these inner diameter dimensions. The guide sheath 400 (as well as any of the variety of components used in combination with the sheath 400) can be an over-the-wire (OTW) or rapid exchange type device, which will be described in more detail below.

As described above, the sheath 400 can include a body 402 formed of generally three layers, including a lubricious inner liner, a reinforcement layer, and an outer jacket layer. The reinforcement layer can include a braid to provide good torqueability optionally overlaid by a coil to provide good kink resistance. In sheaths where the reinforcement layer is a braid alone, the polymers of the outer jacket layer can be generally higher durometer and thicker to avoid issues with kinking. The wall thickness of such sheaths that are braid alone with thicker polymer can be about 0.011". The wall thickness of the sheaths 400 described herein having a braid with a coil overlay provide both torqueability and kink resistance and can have a generally thinner wall, for example, a wall thickness of about 0.0085". The proximal end outer diameter can thereby be reduced to about 0.107" outer diameter. Thus, the sheath 400 is a high performance sheath 400 that has good torque and kink resistance with a thinner wall providing an overall lower profile to the system. The thinner wall and lower profile allows for a smaller insertion hole through the vessel without impacting overall lumen size. In some implementations, the wall thickness of the guide sheath 400 can slowly step down to be thinner towards a distal end of the sheath compared to a proximal end.

The guide sheath 400 may include a distal tip 406 that is designed to seal well with an outer diameter of a catheter extending through its working lumen. The distal tip 406 can be formed of soft material that is devoid of both liner and reinforcement layers. The lubricious liner layer and also the reinforcement layer can extend through a majority of the body 402 except for a length of the distal tip 406 (see FIG. 2C). The length of this unlined, unreinforced portion of the distal tip 406 of the sheath 400 can vary. In some implementations, the length is between about 3 mm to about 6 mm of the distal end region of the sheath 400. Thus, the liner 409 of the sheath 400 can terminate at least about 3 mm away from the distal-most terminus of the sheath 400 leaving the last 3 mm unlined soft material forming the distal tip 406. In some implementations, the coil and braid of the reinforcement layer can have their ends held in place by a radiopaque markers 411, such as a marker band positioned near a distal-most terminus of the sheath 400. The liner layer 409 can extend at least a length distal to the marker band 411 before terminating, for example, a length of about 1 mm. The staggered termination of the wall layers can aid in the transition from the marker band 411 to the soft polymer material 407 of the distal tip 406. The soft polymer material 407 can extend a length beyond the liner layer 409. The unlined, soft material 407 forming the distal tip 406 can be a PEBAX material having a durometer of no more than about 40 D, no more than about 35 D, no more than about 62 A, or no more than about 25 D. The softness of the material and the length of this unlined distal tip 406 of the sheath 400 can vary. Generally, the material is soft enough to be compressed down onto the outer diameter of the catheter 200 extending through the lumen of the sheath 400, such as upon application of a negative pressure through the lumen. The length of this unlined, unreinforced region 407 of the distal tip 406 is long enough to provide a good seal, but not so long as to cause problems with according or folding over during relative sliding between the sheath 400 and the catheter 200 that might blocking the sheath lumen or negatively impacting slidability of the catheter 200 within the sheath lumen.

The distal tip 406 can have an inner diameter that approaches the outer diameter of the catheter 200 that extends through the sheath 400. In some implementations, the inner diameter of the distal tip 406 can vary depending on what size catheter is to be used. For example, the inner diameter of the sheath at the distal tip 406 can be about 0.106" when the outer diameter of the catheter near the proximal end is about 0.101" such that the difference in diameters is about 0.005". Upon application of a vacuum, the soft unlined and unreinforced distal tip 406 can move to eliminate this 0.005" gap and compress down onto the outer diameter of the catheter 200 near its proximal end region upon extension of the catheter 200 out its distal opening 408. The difference between the inner diameter of the distal tip 406 and the outer diameter of the catheter can be between about 0.002"-0.006". The inner diameter of the distal tip 406 can also be tapered such the inner diameter at the distal-most terminus of the opening 408 is only 0.001" to 0.002" larger than the outer diameter of the proximal end of the catheter 200 extending through the working lumen. In some implementations, the distal tip 406 is shaped such that the walls are beveled at an angle relative to a central axis of the sheath 400, such as about 60 degrees.

Figure 2C:
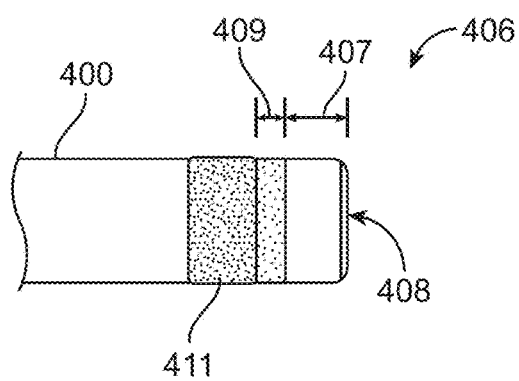
FIG. 2C is a detail view of FIG. 2A taken at circle C-C.
Figure 2D:
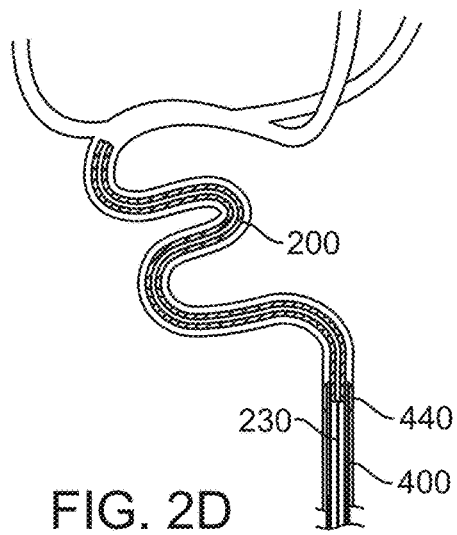
FIG. 2D illustrates an implementation of an arterial access device having a distal occlusion balloon.

In some instances it is desirable for the sheath body 402 to also be able to occlude the artery in which it is positioned, for example, during procedures that may create distal emboli. Occluding the artery stops antegrade blood flow and thereby reduces the risk of distal emboli that may lead to neurologic symptoms such as TIA or stroke. FIG. 2D shows an arterial access device or sheath 400 that has a distal occlusion balloon 440 that upon inflation occludes the artery at the position of the sheath distal tip 406. At any point in a procedure, for example, during removal of an occlusion by aspiration and/or delivery of a stentriever or other interventional device, the occlusion balloon 440 can be inflated to occlude the vessel to reduce the risk of distal emboli to cerebral vessels. The sheath 400 can include an inflation lumen configured to deliver a fluid for inflation of the occlusion balloon 440 in addition to the working lumen of the sheath 400. The inflation lumen can fluidly connect the balloon 440, for example, to arm 412 on the proximal adaptor. This arm 412 can be attached to an inflation device such as a syringe to inflate the balloon 440 with a fluid when vascular occlusion is desired. The arm 412 may be connected to a passive or active aspiration source to further reduce the risk of distal emboli.

According to some implementations, the length of the guide sheath 400 is long enough to access the target anatomy and exit the arterial access site with extra length outside of a patient's body for adjustments. For example, the guide sheath 400 (whether having a distal occlusion balloon 440 or not) can be long enough to access the petrous ICA from the femoral artery such that an extra length is still available for adjustment. The guide sheath 400 can be a variety of sizes to accept various working devices and can be accommodated to the operator's preference. For example, current MAT and SMAT techniques describe delivering aspiration catheters having inside diameters of 0.054"-0.072" to an embolus during AIS. Accordingly, the working lumen of the guide sheath 400 can be configured to receive the catheter 200 as well as other catheters or working devices known in the art. For example, the working lumen can have an inner diameter sized to accommodate at least 6 French catheters (1.98 mm or 0.078" OD), or preferably at least 6.3 French catheters (2.079 mm or 0.082" OD). The inner diameter of the guide sheath 400, however, may be smaller or larger to be compatible with other catheter sizes. In some implementations, the working lumen can have an inner diameter sized to accommodate 7 French (2.31 mm or 0.091" OD) catheters or 8 French (2.64 mm or 0.104" OD) or larger catheters. In some implementations, the working lumen can have an inner diameter that is at least about 0.054" up to about 0.070", 0.071", 0.074", 0.087", 0.088", or 0.100" and thus, is configured to receive a catheter 200 having an outer diameter that fits snug with these dimensions. Regardless of the length and inner diameter, the guide sheath 400 is resistant to kinking during distal advancement through the vasculature.

The working lumen included in the sheath 400 can be sized to receive its respective working devices in a sliding fit. The working lumen may have an inner diameter that is at least 0.001 inch larger than an outer diameter of any catheter 200 it is intended to receive, particularly if the catheter 200 is to be used for aspiration as will be described in more detail below. As described in more detail below, the catheter 200 can include a slit 236 in the luminal portion 222 configured to widen slightly upon application of suction from an aspiration source and improve sealing between the catheter 200 and the guide sheath 400. Additionally or alternatively, the distal tip 406 of the sheath 400 can be designed to move downward onto the outer diameter of the catheter 200 to improve sealing, as described above. The strength of the seal achieved allows for a continuous aspiration lumen from the distal tip of the catheter 200 to a proximal end 403 of the guide sheath 400 where it is connected to an aspiration source, even in the presence of lower suction forces with minimal to no leakage. Generally, when there is enough overlap between the catheter 200 and the guide sheath 400 there is no substantial leakage. However, when trying to reach distal anatomy, the catheter 200 may be advanced to its limit and the overlap between the catheter 200 and the guide sheath 400 is minimal. Thus, additional sealing can be desirable to prevent leakage around the catheter 200 into the sheath 400. The sealing between the catheter 200 and the guide sheath 400 can prevent this leakage upon maximal extension of catheter 200 relative to sheath 400.

Distal Access Catheter

Figure 3:
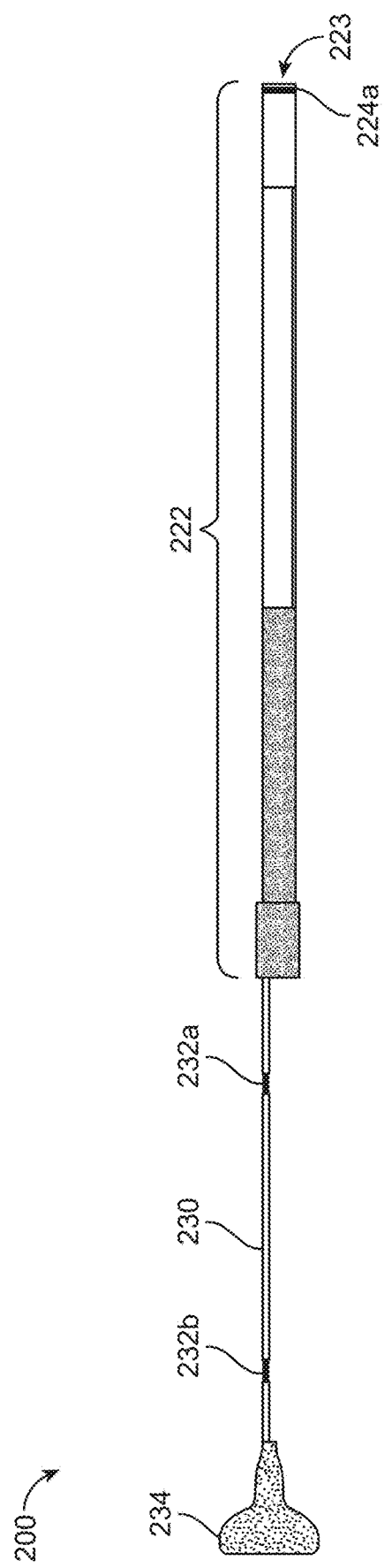
FIG. 3 is a side view of an implementation of a catheter.

Again with respect to FIGS. 2A-2B and also FIGS. 3, and 8A-8C, the distal access system 100 can include a distal access or support catheter 200 configured to extend through and out the distal end of the guide sheath 400. FIG. 3 illustrates a side elevational view of an implementation of the catheter 200. The catheter 200 can include a relatively flexible, distal luminal portion 222 coupled to a more rigid, kink-resistant proximal extension 230. The term "control element" as used herein can refer to a proximal region configured for a user to cause pushing movement in a distal direction as well as pulling movement in a proximal direction. The control elements described herein may also be referred to as spines, tethers, push wires, push tubes, or proximal extensions having any of a variety of configurations. The proximal extension can be hollow or tubular element. The proximal extension can also be solid and have no inner lumen, such as a solid rod, ribbon, or other solid wire type element. Generally, the proximal extensions describes herein are configured to move its respective component (to which it may be attached or integral) in a bidirectional manner through a lumen.

Figure 1B:
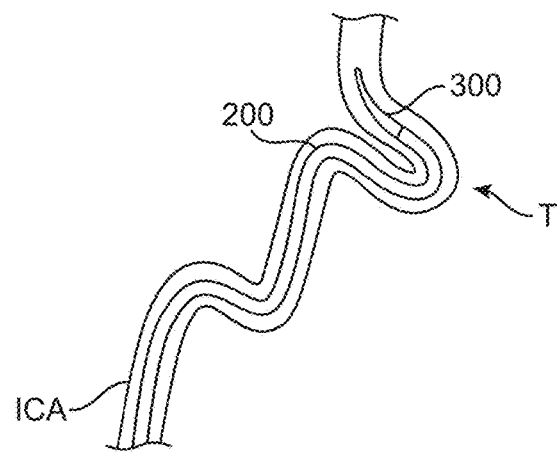

The catheter 200 provides a quick way to access stroke locations with simplicity even through the extreme tortuosity of the cerebral vasculature. The catheters described herein have a degree of flexibility and deliverability that makes them optimally suitable to be advanced through the cerebral vascular anatomy without kinking or ovalizing even when navigating hairpin turns. For example, the distal luminal portion 222 can perform a 180 degree turn (see turn T shown in FIG. 1B near the carotid siphon) and maintain a folded width across of 4.0 mm without kinking or ovalizing. Further, the distal luminal portion 222 has a degree of flexibility that maintains the natural tortuosity of the vessels through which it is advanced without applying straightening forces such that the natural shape and curvature of the anatomy is maintained during use. The catheter 200, particularly in combination with a catheter advancement element 300, which will be described in more detail below, provides an extended conduit beyond the guide sheath 400 having exceptional deliverability through convoluted anatomy that allows for delivering aspirational forces to a target stroke site as well as for the delivery of stroke interventional devices such as another catheter, or a device such as a stent retriever, stent, flow diverter or other working devices.

An inner lumen 223 extends through the luminal portion 222 between a proximal end and a distal end of the luminal portion 222. The inner lumen 223 of the catheter 200 can have a first inner diameter and the working lumen of the guide sheath 400 can have a second, larger inner diameter. Upon insertion of the catheter 200 through the working lumen of the sheath 400, the lumen 223 of the catheter 200 can be configured to be fluidly connected and contiguous with the working lumen of the sheath 400 such that fluid flow into and/or out of the system 100 is possible, such as by applying suction from an aspiration source coupled to the system 100 at a proximal end. The combination of sheath 400 and catheter 200 can be continuously in communication with the bloodstream during aspiration at the proximal end with advancement and withdrawal of catheter 200.

The spined catheter system can create advantages for distal access over conventional catheters particularly in terms of aspiration. The step change in the internal diameter of the catheter column creates a great advantage in aspiration flow and force that can be generated by the spined catheter 200 in combination with the conventional guide catheter. For example, where a spined catheter 200 with a 0.070" internal diameter is paired with a standard 6 F outer diameter/0.088" internal diameter guide catheter (e.g. Penumbra Neuron MAX 088) can create aspiration physics where the 0.088" catheter diameter will predominate and create a 0.080 equivalent flow in the entire system.

In addition to aspiration procedures, the catheter 200 and distal access system 100 can be used for delivery of tools and interventional working devices. As will be described in more detail below, a typical stent retriever to be delivered through the catheter 200 can have a push wire control element of 180 cm. The distal access system 100 having a spined support catheter 200 allows for reaching distal stroke sites using much shorter lengths (e.g. 120 cm-150 cm). The overall length can be as important as diameter and radius on aspiration through the catheter. The shorter lengths in combination with the elimination of the multiple RHVs typical in tri-axial systems allows for a single-operator use.

Where the catheter is described herein as an aspiration catheter it should not be limited to only aspiration. Similarly, where the catheter is described herein as a way to deliver a stent retriever or other working device it should not be limited as such. It should also be appreciated that the systems described herein can be used to perform procedures that incorporate a combination of treatments. For example, the catheter 200 can be used for the delivery of a stent retriever delivery system, optionally in the presence of aspiration through the catheter 200. As another example, a user may start out performing a first interventional procedure using the systems described herein, such as aspiration thrombectomy, and switch to another interventional procedure, such as delivery of a stent retriever or implant.

It should also be appreciated that the catheter 200 need not be spined or include the proximal extension 230 and instead can be a non-spined, conventional catheter having a uniform diameter. The terms "support catheter", "spined catheter", "distal access catheter", "aspiration catheter," and "intermediate catheter" may be used interchangeably herein.

It is desirable to have a catheter 200 having an inner diameter that is as large as possible that can be navigated safely to the site of the occlusion, in order to optimize the aspiration force in the case of aspiration and/or provide ample clearance for delivery of a working device. A suitable size for the inner diameter of the distal luminal portion 222 may range between 0.040" and 0.100", or more preferably between 0.054" and 0.088", depending on the patient anatomy and the clot size and composition. The outer diameter of the distal luminal portion 222 can be sized for navigation into cerebral arteries, for example, at the level of the M1 segment or M2 segment of the cerebral vessels. The outer diameter (OD) should be as small as possible while still maintaining the mechanical integrity of the catheter 200. In an implementation, the difference between the OD of distal luminal portion 222 of the catheter 200 and the inner diameter of the working lumen of the guide sheath 400 is between 0.001" and 0.002". In another implementation, the difference is between 0.001" and 0.004". The clearance between inner diameter of the guide sheath 400 and the outer diameter of the catheter 200 can vary throughout the length of the catheter 200. For example, the distal luminal portion 222 of the catheter 200 can have localized regions of enlarged outer diameter creating localized low clearance regions (e.g., about 0.001" difference) configured for localized sealing upon application of aspiration pressure through the system.

In some implementations, the distal luminal portion 222 of the catheter 200 has an outer diameter (OD) configured to fit through a 6 F introducer sheath (0.070"-0.071") and the lumen 223 has an inner diameter (ID) that is sized to receive a 0.054" catheter. In some implementations, the distal luminal portion 222 of the catheter 200 has an OD configured to fit through an 8 F introducer sheath (0.088") and the lumen 223 has an ID that is sized to receive a 0.070" or 0.071" catheter. In some implementations, the OD of the distal luminal portion 222 is 2.1 mm and the lumen 223 has an ID that is 0.071". In some implementations, the lumen 223 has an ID that is 0.070" to 0.073". The outer diameter of the guide sheath 400 can be suitable for insertion into at least the carotid artery, with a working lumen suitably sized for providing a passageway for the catheter 200 to treat an occlusion distal to the carotid artery towards the brain. In some implementations, the ID of the working lumen can be about 0.074" and the OD of the body of the guide sheath 400 can be about 0.090", corresponding to a 5 French sheath size. In some implementations, the ID of the working lumen can be about 0.087" and the OD of the body of the guide sheath 400 can be about 0.104", corresponding to a 6 French sheath size. In some implementations, the ID of the working lumen can be about 0.100" and the OD of the body of the guide sheath 400 can be about 0.117", corresponding to a 7 French sheath size. In some implementations, the guide sheath 400 ID is between 0.087" and 0.088" and the OD of the distal luminal portion 222 of the catheter 200 is approximately 0.082" and 0.086" such that the difference in diameters is between 0.001" and 0.005".

Smaller or larger sheath sizes are considered. For example, in some implementations the ID of the lumen 223 is about 0.088" and the OD of the distal luminal portion is between 0.101"-0.102". However, a conventional 7 French sheath has an ID that is only about 0.100" and a conventional 8 French sheath has an ID that is about 0.113" such that it would not provide a suitable sealing fit with the OD of the distal luminal portion of the catheter for aspiration embolectomy (i.e. 0.011" clearance). Thus, the guide sheath 400 can be designed to have an inner diameter that is better suited for the 0.088" catheter, namely between 0.106"-0.107". Additionally, the 0.088" catheter can have a step-up in OD from 0.101"-0.102" to about 0.105"-0.107" OD near a proximal end region to provide a localized area optimized for sealing with the guide sheath during application of high pressure.

In an implementation, the luminal portion 222 of the catheter 200 has a uniform diameter from a proximal end to a distal end. In other implementations, the luminal portion 222 of the catheter 200 is tapered and/or has a step-down towards the distal end of the distal luminal portion 222 such that the distal-most end of the catheter 200 has a smaller outer diameter compared to a more proximal region of the catheter 200, for example, near where the distal luminal portion 222 seals with the guide sheath 400. In another implementation, the luminal portion 222 of the catheter OD steps up at or near an overlap portion to more closely match the sheath inner diameter as will be described in more detail below. This step-up in outer diameter can be due to varying the wall thickness of the catheter 200. For example, the catheter 200 can have a wall thickness that is slightly thicker near the proximal end to provide better sealing with the sheath compared to a wall thickness of the catheter 200 near the distal end. The catheter 200 can have a thicker wall at this location while maintaining a uniform inner diameter. This implementation is especially useful in a system with more than one catheter suitable for use with a single access sheath size. Smaller or larger sheath sizes are considered herein. In some implementations, a thicker wall can be created by embedding a radiopaque material (e.g. tungsten) such that the localized step-up in OD can be visualized during a procedure. The catheter 200 may have a step-up in outer diameter near the proximal end region that does not result from a thicker wall. For example, the inner diameter of the lumen may also step-up such that the wall thickness remains uniform, but the lumen size increases thereby increasing the overall OD at this location.

The length of the luminal portion 222 can be shorter than a length of the working lumen of the guide sheath 400 such that upon advancement of the luminal portion 222 towards the target location results in an overlap region 348 between the luminal portion 222 and the working lumen (see FIG. 2B). The length of the overlap region 348 can vary depending on the length of the distal luminal portion 222 and the distance to the target location relative to the distal end of the guide sheath 400. Taking into account the variation in occlusion sites and sites where the guide sheath 400 distal tip 406 may be positioned, the length of the luminal portion 222 may range from about 10 cm to about 80 cm, or between 35 cm to about 74 cm, or between about 45 cm to about 60 cm. In some implementations, the distal luminal portion 222 of the catheter 200 can be between 20-45 cm and the proximal extension 230 of the catheter 200 can be between about 90 cm to about 100 cm such that the catheter 200 can have a total working length that is approximately 115 cm. The body 402 of the guide sheath 400 can be between 80 cm to about 90 cm. In other implementations, the working length of the catheter 200 between a proximal end of the catheter to a distal end of the catheter can be greater than 115 cm up to about 130 cm. In some implementations, the catheter 200 can have a working length greater than 130 cm between a proximal tab 234 (or proximal hub) and the distal tip, the distal luminal portion 222 can have a shaft length of about 40 cm±3 cm. The distal luminal portion 222 can have a shaft length that is at least about 45 cm up to a length that is shorter than the working length of the sheath 400. The body 402 of the guide sheath 400 can be between about 80 cm to about 90 cm.

The length of the luminal portion 222 can be less than the length of the body 402 of the guide sheath 400 such that as the catheter 200 is extended from the working lumen there remains an overlap region 348 of the catheter 200 and the inner diameter of the working lumen. A seal can be formed within a region of the overlap region 348. In some implementations, the length of the luminal portion 222 is sufficient to reach a region of the M1 segment of the middle cerebral artery (MCA) and other major vessels from a region of the internal carotid artery such that the proximal end region of the luminal portion 222 of the catheter 200 is still maintained proximal to certain tortuous anatomies (e.g., brachiocephalic take-off BT, the aortic arch AA, or within the descending aorta DA). In an implementation, the luminal portion 222 of the catheter has a length sufficient to position its distal end within the M1 segment of the MCA and a proximal end within the aortic arch proximal to take-offs from the arch. In an implementation, the luminal portion 222 of the catheter has a length sufficient to position its distal end within the M1 segment of the MCA and a proximal end within the descending aorta DA proximal to the aortic arch AA. Used in conjunction with a guide sheath 400 having a sheath body 402 and a working lumen, in an implementation where the catheter 200 reaches the ICA and the distance to embolus can be less than 20 cm.

The distal luminal portion 222 having a length that is less than 80 cm, for example approximately 45 cm up to about 70 cm, The distal luminal portion 222, can allow for an overlap region 348 with the body 402 within which a seal forms with the sheath while still providing sufficient reach to intracranial vessels. The carotid siphon CS is an S-shaped part of the terminal ICA beginning at the posterior bend of the cavernous ICA and ending at the ICA bifurcation into the anterior cerebral artery ACA and middle cerebral artery MCA. In some implementations, the distal luminal portion 222 can be between about 35 cm-80 cm, or between 40 cm-75 cm, or between 45 cm-60 cm long to allow for the distal end of the catheter 200 to extend into at least the middle cerebral arteries while the proximal control element 230 and/or the sealing element on the proximal end region of the distal luminal portion 222 remains proximal to the carotid siphon, and preferably within the aorta as will be described in more detail below.

The distal luminal portion 222 can have a length measured from its point of attachment to the proximal control element 230 to its distal end that is long enough to extend from a region of the internal carotid artery (ICA) that is proximal to the carotid siphon to a region of the ICA that is distal to the carotid siphon, including at least the M1 region of the brain. There exists an overlap region 348 between the luminal portion 222 of the catheter 200 and the working lumen of the guide sheath 400 upon extension of the luminal portion 222 into the target anatomy. A seal to fluid being injected or aspirated can be achieved within the overlap region 348 where the OD of the catheter 200 along at least a portion of the distal luminal portion 222 substantially matches the inner diameter of the guide sheath 400 or the difference can be between 0.001"-0.002". The difference between the catheter OD and the inner diameter of the guide sheath 400 can vary, for example, between 1-2 thousandths of an inch, or between 1-4 thousandths of an inch, or between 1-12 thousandths of an inch. This difference in OD/ID between the sheath and the catheter can be along the entire length of the distal luminal portion 222 or can be a difference in a discrete region of the distal luminal portion 222, for example, a cylindrical, proximal end region of the distal luminal portion 222. In some implementations, a seal to fluid being injected or aspirated between the catheter and the sheath can be achieved within the overlap 348 between their substantially similar dimensions without incorporating any separate sealing structure or seal feature. In some implementations, an additional sealing structure located near the proximal end region of the distal luminal portion 222 provides sealing between the inner diameter of the sheath and the outer diameter of the catheter.

The length of the overlap region 348 between the sheath and the distal luminal portion varies depending on the distance between the distal end of the sheath and the embolus as well as the length of the luminal portion 222 between its proximal and distal ends. The overlap region 348 can be sized and configured to create a seal that allows for a continuous aspiration lumen from the distal tip region of the catheter 200 to a proximal end region 403 of the guide sheath 400 where it can be connected to an aspiration source. In some implementations, the strength of the seal achieved can be a function of the difference between the outer diameter of the catheter 200 and the inner diameter of the working lumen as well as the length of the overlap region 348, the force of the suction applied, and the materials of the components. For example, the sealing can be improved by increasing the length of the overlap region 348. However, increasing the length of the overlap region 348 can result in a greater length through which aspiration is pulled through the smaller diameter of the luminal portion 222 rather than the larger diameter of the working lumen. As another example, higher suction forces applied by the aspiration source can create a stronger seal between the luminal portion 222 and the working lumen even in the presence of a shorter overlap region 348. Further, a relatively softer material forming the luminal portion and/or the body 402 can still provide a sufficient seal even if the suction forces are less and the overlap region 348 is shorter. In an implementation, the clearance of the overlap region 348 can enable sealing against a vacuum of up to approximately 28 inHg with minimal to no leakage. The clearance of the overlap region can enable sealing against a vacuum of up to about 730 mmHg with minimal to no leakage.

In other implementations, the overlap region 348 itself does not provide the sealing between the body 402 and the luminal portion 222. Rather, an additional sealing element positioned within the overlap region 348, for example, a discreet location along a region of the luminal portion 222 narrows the gap between their respective ID and ODs such that sealing is provided by the sealing element within the overlap region 348. In this implementation, the location of the seal between the luminal portion 222 and the body 402 can be positioned more proximally relative to certain tortuous regions of the anatomy. For example, the proximal end region of the luminal portion 222 can have a discreet step-up in outer diameter that narrows the gap between the OD of the luminal portion 222 and the ID of the body 402. This step-up in outer diameter of the luminal portion 222 can be positioned relative to the overall length of the luminal portion 222 such that the sealing region between the two components avoids making sharp turns. For example, the sealing region can include the proximal end region of the luminal portion 222 a certain distance away from the distal tip of the catheter and this sealing region can be designed to remain within the descending aorta DA when the distal end region of the luminal portion 222 is advanced through the aortic arch, into the brachiocephalic trunk BT, the right common carotid RCC, up to the level of the petrous portion of the internal carotid artery and beyond. Maintaining the sealing region below the level of the aortic arch while the distal end of the catheter is positioned within, for example, the M1 region of the MCA is a function of the length of the luminal portion 222 as well as the length and position of the sealing portion on the catheter. The sealing region on the luminal portion 222 can be located a distance from the distal tip of the catheter that is at least about 40 cm, 45 cm, 50 cm, 55 cm, 60 cm, 65 cm, 70 cm, up to about 75 cm from the distal tip of the catheter.

Use of the term "seal" in the context of the catheter and the guide sheath refers to a condition where upon application of an aspiration force fluid is prevented from substantially passing from one side of the seal to the other. For example, the low clearance between the OD of the catheter and the ID of the sheath at the seal can prevent, upon application of aspiration pressure through the system, substantial passage of blood between outer surface of the catheter and the inner surface of the sheath and thereby create a seal. The seal does not necessarily mean the entire catheter system is sealed. For example, even when the catheter is "sealed" with the sheath, blood can still be aspirated into the lumen of the catheter and through the guide sheath (at least until "corking" of the distal end of the catheter 200 where a full seal of the entire system may occur).

Figure 1C:
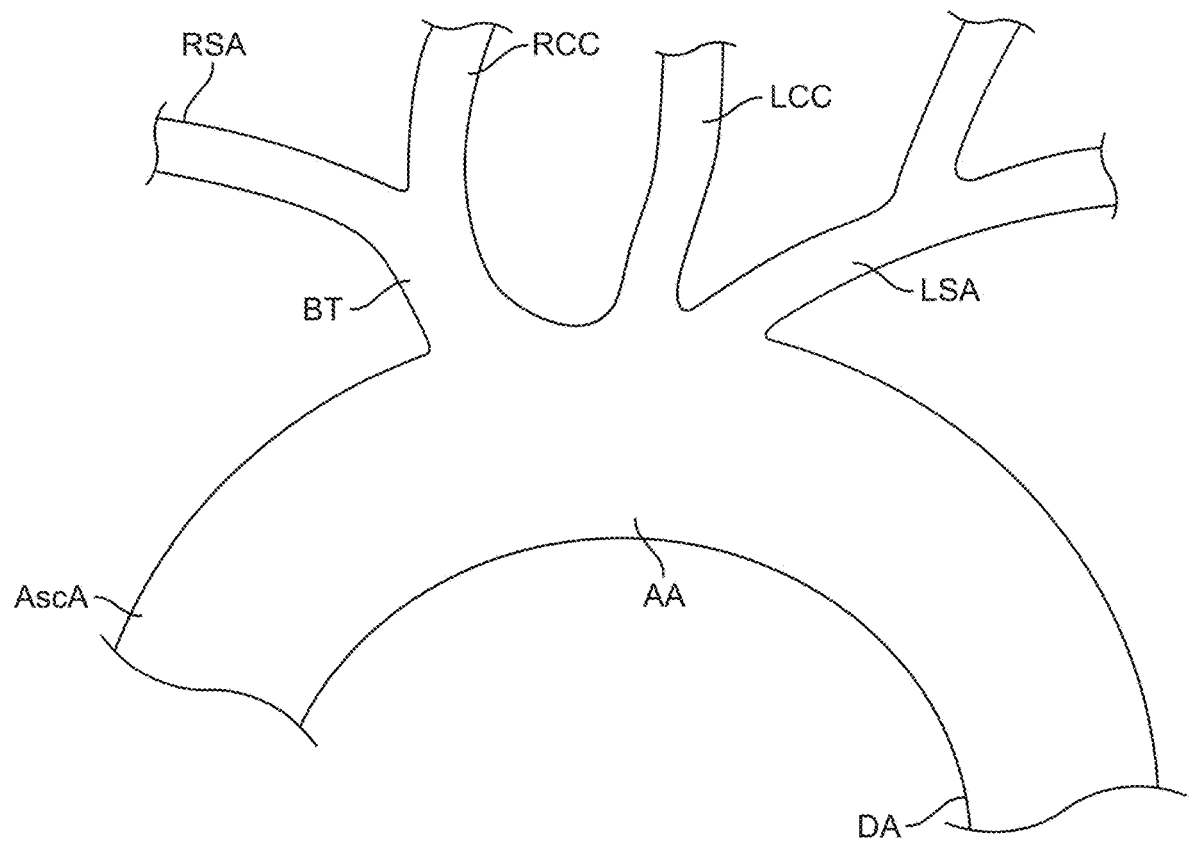
FIG. 1C illustrates the aortic arch including the take-offs of the brachiocephalic BT, left common carotid LCC, and left subclavian arteries LSA from the aortic arch AA.

The brachiocephalic take-off (BT) is typically a very severe turn off the aortic arch AA for a transfemorally-delivered catheter seeking the right-sided cerebral circulation (shown in FIG. 1C). A catheter traversing from the femoral artery through the iliac circulation into the descending aorta DA turns as it approaches the aortic arch AA and reaches across the take-off of other great vessels to reach the brachiocephalic take-off (BT), which is the furthest "reach" of the great vessels of the aortic arch AA. FIG. 1C shows the substantial and obligatory S-turn created by that anatomy. A catheter must traverse this S-turn along a path of insertion from a femoral artery insertion location in order to reach the internal carotid artery (ICA). The left ICA often takes off from the brachiocephalic and thus, has a similar challenge and can create an even tighter S-turn. Should the left ICA have a typical take-off between the brachiocephalic BT and the left subclavian artery LSA take-off, then the reach may be less severe, but an S-turn still develops of lesser severity. In some implementations, the length of the luminal portion 222 is sufficient to reach a region of the M1 segment of the middle cerebral artery (MCA) and other major vessels from a region of the internal carotid artery while the proximal end region of the luminal portion 222 of the catheter 200 is still maintained proximal to certain tortuous anatomies (e.g. brachiocephalic take-off BT, the aortic arch AA, or within the descending aorta DA). In an implementation, the luminal portion 222 of the catheter has a length sufficient to position its distal end within the M1 segment of the MCA and a proximal end within the aortic arch proximal to take-offs from the arch. In an implementation, the luminal portion 222 of the catheter has a length sufficient to position its distal end within the M1 segment of the MCA and a proximal end within the descending aorta DA proximal to the aortic arch AA. Used in conjunction with a guide sheath 400 having a sheath body 402 and a working lumen, in an implementation where the catheter 200 reaches the ICA and the distance to embolus can be less than 20 cm.

The catheter 200 can telescope relative to the sheath (and/or relative to another catheter 200) such that the distal end of the distal luminal portion 222 can reach cerebrovascular targets within, for example, the M1, M2 regions while the proximal end of the distal luminal portion 222 remains proximal to or below the level of severe turns along the path of insertion. For example, the entry location of the catheter system can be in the femoral artery and the target embolus can be distal to the right common carotid artery (RCC), such as within the M1 segment of the middle cerebral artery on the right side. The proximal end region of the distal luminal portion 222 (e.g. where the sealing element is located and/or where the material transition to the proximal extension 230 occurs) can remain within a vessel that is proximal to severely tortuous anatomy: the carotid siphon, the right common carotid RCC, the brachiocephalic trunk BT, the take-off of the brachiocephalic artery from the aortic arch, the aortic arch AA as it transitions from the descending aorta DA. The descending aorta DA is a consistently straight segment in most anatomies. FIG. 1C illustrates the aortic arch AA, which separates the ascending aorta AscA and descending aorta DA. The distal-most carotid from a femoral access point is the right common carotid RCC artery, which takes off from the brachiocephalic trunk BT (or the left common carotid LCC, which takes off from the same brachiocephalic trunk BT in some patients—the so-called "bovine anatomy"). The distal luminal portion 222 may have a length that, when inserted into the RCC, is configured to extend from a target location in the M1 or M2 regions down to the brachiocephalic trunk BT, or down to the level of the aortic arch AA, or down to the descending aorta DA, which is sometimes referred to herein as being "below the takeoff" of the brachiocephalic trunk BT. This avoids inserting the stiffer proximal extension 230, or the material transition between the stiffer proximal extension 230 and the distal luminal portion 222, from taking the turn of the aortic arch or the turn of the brachiocephalic take-off, which can often be very severe. The turn of the aortic arch and the takeoff of the brachiocephalic are often the first severe turns catheters are likely to traverse as they ascend to the brain via the RCC artery. The less flexible portions of the catheter segment are able to avoid the regions of increased tortuosity near the level of the internal carotid artery. The distal luminal portion 222 can transition in flexibility towards the proximal region to approach the flexibility of the stiffer proximal extension 230. The distal end of the catheter can be used to target the left cerebral circulation while the proximal extension 230 of the catheter 200 as well as the material transitions of the distal luminal portion 222 near the proximal extension 230 remain below the level of tortuosity of the brachiocephalic turn (e.g., within the aorta, proximal to the take-off of the left common carotid (LCC) artery, and preferably within the descending aorta DA). Similarly, the sealing region or a majority of the sealing region between the distal luminal portion 222 and the sheath preferably remains proximal to these severe turns.

In some implementations, the distal luminal portion 222 can have a length that allows the distal end of the distal luminal portion 222 to reach distal to the carotid siphon into the cerebral portion of the internal carotid artery while at the same time the proximal end of the distal luminal portion 222 (e.g. where it transitions to the proximal extension 230 as will be described in more detail below) remains within the aorta proximal to the take-off of the brachiocephalic trunk BT, for example within the descending aorta DA (see FIG. 2C). In this implementation, the distal luminal portion can be between about 35 cm and 75 cm in length, for example, between 45 cm-70 cm, or 65 cm long.

The attachment region between the more rigid, proximal extension 230 and the more flexible, distal luminal portion 222 creates a transition in material and flexibility that can be prone to kinking. Thus, it is preferable to avoid advancing the attachment region into extreme curvatures. For example, the distal luminal portion 222 can have a length that allows the point of attachment to be advanced no further than the first turn of the carotid siphon, or no further than the brachiocephalic artery take-off, or nor further than the aortic arch AA, or no further than the descending aorta DA when the catheter is advanced from a femoral access site. In some implementations, the distal luminal portion 222 has a length sufficient to allow the point of attachment to remain within the descending aorta DA while still accessing M1 or M2 regions of the neurovasculature. Locating the material transition within the extreme turn of the brachiocephalic take-off BT from the aortic arch AA is generally avoided when the distal luminal portion 222 has a length that is between about 35 cm to about 75 cm, or 45 cm-70 cm, or 65 cm.

The site of insertion for the guide sheath 400 and thus for the catheter 200 being inserted through the guide sheath 400 can vary including the femoral artery near the groin as well as the carotid, radial, ulnar, or brachial arteries of the arm, or subclavian artery. The length of the distal luminal portion 222 can remain substantially the same no matter the point of access being used to ensure the distal end of the distal luminal portion 222 is long enough to reach the distal regions of the M1 or M2 while the material transition with the proximal extension 230 remains proximal to the brachiocephalic take-off (e.g., within the aortic arch). The length of the proximal extension 230, however, may be shorter for certain access points such as the subclavian artery compared to a catheter designed for insertion from more distant access points such as the femoral artery. Similar modifications can be made to the guide sheath 400 and the catheter advancement element 300 if access points other than the femoral artery are used. Alternatively, the catheter lengths can remain unchanged regardless the access point being used.

In some implementations, the distal luminal portion 222 can have a length that allows the distal end of the distal luminal portion 222 to reach distal to the carotid siphon into the cerebral portion of the internal carotid artery while at the same time the proximal end of the distal luminal portion 222 (e.g. where it transitions to the proximal extension 230 as will be described in more detail below) remains within the aorta proximal to the take-off of the brachiocephalic trunk BT, for example within the descending aorta DA (see FIG. 1C). In this implementation, the distal luminal portion can be between about 35 cm and 60 cm.

As mentioned, the point of attachment between the proximal extension 230 and the distal luminal portion 222 creates a transition in material and flexibility that can be prone to kinking. Thus, it is preferable to avoid advancing the point of attachment into extreme curvatures. For example, the distal luminal portion 222 can have a length that allows the point of attachment to be advanced no further than the first turn of the carotid siphon, or no further than the brachiocephalic artery take-off BT, or the aortic arch AA. In some implementations, the distal luminal portion 222 has a length sufficient to allow the point of attachment to remain within the descending aorta DA while still accessing M1 or M2 regions of the neurovasculature. Locating the material transition within the extreme turn of the brachiocephalic take-off BT from the aortic arch AA is generally avoided when the distal luminal portion 222 has a length that is between about 35 cm to about 60 cm.

As described above, a seal can be created at the overlap region 348 between the distal luminal portion 222 and the sheath body 402. It can be generally desirable to position the sealing overlap region 348 outside of extreme curvatures of the neurovasculature. In some implementations, the distal luminal portion 222 can have a length that allows for the distal end of the distal luminal portion 222 to extend distal to the carotid siphon into the cerebral portion of the internal carotid artery while at the same time the overlap region 348 remain proximal to the brachiocephalic takeoff BT, the aortic arch AA, or within the descending aorta DA. In this implementation, the length can be between about 35 cm to about 60 cm, about 40 cm to about 60 cm, or greater than 40 cm up to less than the working length of the sheath body 402.

As described above with respect to FIG. 2C, the unreinforced region 407 of the distal tip 406 of the sheath 400 can have a length that allows it to provide sufficient sealing force onto the outer surface of the catheter 200 upon application of a negative pressure. The distal luminal portion 222 of the catheter 200 used with this implementation of sheath 400 can have a length that is shorter than 60 cm, shorter than 50 cm, shorter than 40 cm, shorter than 35 cm, shorter than 30 cm to about 10 cm. For example, the distal luminal portion 222 of the catheter 200 when used with a sheath 400 having an unreinforced region 407 configured for sealing can be less than about 30 cm, for example, between 10 cm and about 30 cm.

Sealing within the overlap region 348 can be due to the small difference in inner and outer diameters. The proximal end region of the distal luminal portion 222 can have a step-up in outer diameter (e.g. increased wall thickness) providing a region of localized sealing with the inner diameter of the guide sheath. Additionally or alternatively, the localized sealing can be due to an additional sealing element positioned on an external surface of the distal luminal portion or an inner surface of the sheath body. A sealing element can include a stepped up diameter or protruding feature in the overlap region. The sealing element can include one or more external ridge features. The one or more ridge features can be compressible when the luminal portion is inserted into the lumen of the sheath body. The ridge geometry can be such that the sealing element behaves as an O-ring, quad ring, or other piston seal design. The sealing element can include one or more inclined surfaces biased against an inner surface of the sheath body lumen. The sealing element can include one or more expandable members actuated to seal. The inflatable or expandable member can be a balloon or covered braid structure that can be inflated or expanded and provide sealing between the two devices at any time, including after the catheter is positioned at the desired site. Thus, no sealing force need be exerted on the catheter during positioning, but rather applied or actuated to seal after the catheter is positioned. The sealing element can be positioned on the external surface of the distal luminal portion, for example, near the proximal end region of the distal luminal portion and may be located within the overlap region. More than a single sealing element can be positioned on a length of the catheter.

In some implementations, the additional sealing element of the distal luminal portion 222 can be a cup seal, a balloon seal, or a disc seal formed of a soft polymer positioned around the exterior of the distal luminal portion near the overlap region to provide additional sealing. The sealing element can be a thin-wall tubing with an outer diameter that substantially matches the inner diameter of the sheath body lumen. The tubing can be sealed on one end to create a cup seal or on both ends to create a disc or balloon seal. The balloon seal can include trapped air that creates a collapsible space. One or more slits can be formed through the wall tubing such that the balloon seal can be collapsible and more easily passed through an RHV. The balloon seal need not include slits for a less collapsible sealing element that maintains the trapped air. The sealing element can be tunable for sheath fit and collapse achieved.

In some implementations, the system can include one or more features that restrict extension of the catheter 200 relative to the sheath 400 to a particular distance such that the overlap region 348 achieved is optimum and/or the catheter 200 is prevented from being over-inserted. For example, a tab can be positioned on a region of the catheter 200 such that upon insertion of the catheter 200 through the sheath 400 a selected distance, the tab has a size configured to abut against the port through which the catheter 200 is inserted to prevent further distal extension of the catheter 200 through the sheath 400. A tab can also be positioned on a region of the catheter advancement element 300 to ensure optimum extension of the catheter advancement element 300 relative to the distal end of the catheter 200 to aid in advancement of the catheter 200 into the intracranial vessels.

Again with respect to FIG. 3, the proximal extension 230 is configured to move the distal luminal portion 222 in a bidirectional manner through the working lumen of the guide sheath 400 such that the distal luminal portion 222 can be advanced out of the guide sheath 400 into a target location for treatment within the target vessel. In some implementations and as shown in FIG. 3, the proximal extension 230 of the catheter 200 can have a smaller outer diameter than the outer diameter of the distal luminal portion 222 forming a proximal spine or tether to the catheter 200. A smaller outer diameter for the proximal extension 230 than the outer diameter of the distal luminal portion 222 allows for the larger diameter working lumen of the sheath 400 to maintain greater aspiration forces than would otherwise be provided by the smaller diameter luminal portion 222 of the catheter 200 or allow for the delivery of working devices through the lumen with less frictional forces. The markedly shorter length of the luminal portion 222 results in a step up in luminal diameter between the luminal portion 222 contiguous with the working lumen providing a markedly increased radius and luminal area for delivery of a working device and/or aspiration of the clot, particularly in comparison to other systems where the aspiration lumen runs along the entire inner diameter of the aspiration catheter. More particularly, the combined volume of the luminal area of the catheter 200 and the luminal area of the working lumen proximal to the distal luminal portion 222 is greater than the luminal area of the large bore catheter along the entire length of the system. Thus, the likelihood of removing the embolus during a single aspiration attempt may be increased. More particularly, the stepped up luminal diameter along the proximal extension 230 may enable a greater aspiration force to be achieved resulting in improved aspiration of the embolus. Further, this configuration of the catheter 200 and proximal extension 230 greatly speeds up the time required to retract and re-advance the catheter 200 and/or working devices through the working lumen out the distal lumen 408. This describes the time it takes to aspirate the occlusion. The proximal extension 230 of the catheter 200 has a length and structure that extends through the working lumen of the sheath-guide 400 to a proximal end of the system 100 such that the proximal extension 230 can be used to advance and retract the catheter 200 through the working lumen. The proximal extension 230 of the catheter 200, however, takes up only a fraction of the luminal space of the system 100 resulting in increased luminal area for aspiration and/or delivery of working devices. The stepped up luminal diameter also increases the annular area available for forward flushing of contrast, saline, or other solutions while devices such as microcatheters or other devices may be coaxially positioned in the luminal portion 222 of the catheter 200 and/or the working lumen. This can increase the ease and ability to perform angiograms during device navigation.

In an implementation, the distal luminal portion 222 of the catheter 200 is constructed to be flexible and lubricious, so as to be able to safely navigate to the target location. The distal luminal portion 222 can be kink resistant and collapse resistant when subjected to high aspiration forces so as to be able to effectively aspirate a clot. The luminal portion 222 can have increasing flexibility towards the distal end with smooth material transitions along its length to prevent any kinks, angulations or sharp bends in its structure, for example, during navigation of severe angulations such as those having 90° or greater to 180° turns, for example at the aorto-iliac junction, the left subclavian take-off from the aorta, the takeoff of the brachiocephalic (innominate) artery from the ascending aorta and many other peripheral locations just as in the carotid siphon. The distal luminal portion 222 can transition from being less flexible near its junction with the proximal extension 230 to being more flexible at the distal-most end. The change in flexibility from proximal to distal end of the distal luminal portion 222 can be achieved by any of a variety of methods as described herein. For example, a first portion of the distal luminal portion 222 can be formed of a material having a hardness of at least about 72 D or greater along a first length, a second portion can be formed of a material having a hardness that is less than about 72 D, such as about 55 D along a second length, a third portion can be formed of a material having a hardness that is less than about 55 D, such as about 40 D along a third length, a fourth portion can be formed of a material having a hardness less than about 40 D, such as about 35 D along a fourth length, a fifth portion can be formed of a material having a hardness less than about 35 D, such as about 25 D along a fifth length, a sixth portion can be formed of a material having a hardness less than about 25 D, such as about 85 A Tecoflex along a sixth length, a seventh portion can be formed of a material having a hardness less than about 85 A, such as about 80 A Tecoflex. In some implementations, the final distal portion of the distal luminal portion 222 of the catheter 200 can be formed of a material such as Tecothane having a hardness of 62 A that is matched in hardness to a region of the catheter advancement element 300, which will be described in more detail below. Thus, the distal luminal portion 222 transitions from being less flexible near its junction with the proximal extension 230 to being more flexible at the distal-most end where, for example, a distal tip of the catheter advancement element 300 can extend from. Other procedural catheters described herein can have a similar construction providing a variable relative stiffness that transitions from the proximal end towards the distal end of the catheter as will be described elsewhere herein.

The material hardnesses described herein with respect to the distal luminal portion 222 of the catheter as well as with regard to the flexible elongate body 360 of the catheter advancement element 300 can be achieved by a single polymer material or by mixtures of polymer materials. For example, a mixture of 35 D PEBAX and 55 D PEBAX can provide a harder polymeric material than that of 35 D PEBAX alone and a softer polymer material than that of 55 D PEBAX alone. The polymer segments of the various catheter components described herein can incorporate any of a variety of hardnesses between the specific hardnesses identified by blending of one or more polymer materials to achieve a transition in flexibility along a length of the structure. Additionally, the ranges of hardnesses between the proximal end portions of the catheters described herein and a distal end portions of the catheters can vary from greater than 72 D PEBAX (e.g. 72 D PEBAX reinforced with a metallic or non-metallic element) down to less than 35 D (e.g., 62 A Tecothane).

The distal luminal portion 222 can include two or more layers. In some implementations, the distal luminal portion 222 includes an inner lubricious liner, a reinforcement layer, and an outer jacket layer, each of which will be described in more detail.

The lubricious inner liner can be a PTFE liner, with one or more thicknesses along variable sections of flexibility. The PTFE liner can be a tubular liner formed by dip coating or film-casting a removable mandrel, such as a silver-plated copper wire as is known in the art. Various layers can be applied having different thicknesses. For example, a base layer of etched PTFE can be formed having a thickness of about 0.005". A second, middle layer can be formed over the base layer that is Tecoflex SG-80A having a thickness of about 0.0004". A third, top layer can be formed over the middle layer that is Tecoflex SG-93A having a thickness of about 0.0001" or less. The distal luminal portion 222 can additionally incorporate one or more reinforcement fibers (see FIGS. 8B-8C) configured to prevent elongation of the coils, as will be described in more detail below. A reinforcement layer and/or reinforcement fiber can be applied to the inner liner, followed by the outer jacket layer and/or additional outer coating prior to removing the mandrel by axial elongation.

The reinforcement layer is a generally tubular structure formed of, for example, a wound ribbon or wire coil or braid. The material for the reinforcement structure may be stainless steel, for example 304 stainless steel, Nitinol, cobalt chromium alloy, or other metal alloy that provides the desired combination of strengths, flexibility, and resistance to crush. In some implementations, the distal luminal portion 222 has a reinforcement structure that is a Nitinol ribbon wrapped into a coil. For example, the coil reinforcement can be a tapered ribbon of Nitinol set to a particular inner diameter (e.g. 0.078" to 0.085" inner diameter) and having a pitch (e.g. between 0.012" and 0.016"). The ribbon can be 304 stainless steel (e.g. about 0.012"×0.020"). The coil can be heat-set prior to transferring the coil onto the catheter. The pitch of the coil can increase from proximal end towards distal end of the distal luminal portion 222. For example, the ribbon coils can have gaps in between them and the size of the gaps can increase moving towards the distal end of the distal luminal portion 222. For example, the size of the gap between the ribbon coils can be approximately 0.016" gap near the proximal end of the distal luminal portion 222 and the size of the gap between the ribbon coils near the distal end can be larger such as 0.036" gap. This change in pitch provides for increasing flexibility near the distal-most end of the distal luminal portion 222. The reinforcement structure can include multiple materials and/or designs, again to vary the flexibility along the length of the distal luminal portion 222.

The outer jacket layer may be composed of discreet sections of polymer with different durometers, composition, and/or thickness to vary the flexibility along the length of the distal luminal portion 222 as described above.

At least a portion of the outer surface of the catheter 200 can be coated with a lubricious coating such as a hydrophilic coating. In some implementations, the coating may be on an inner surface and/or an outer surface to reduce friction during tracking. The coating may include a variety of materials as is known in the art. The proximal extension 230 may also be coated to improve tracking through the working lumen. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinyl alcohols, hydroxy alkyl cellulosics, algins, saccharides, caprolactones, HYDAK coatings (e.g. B-23K, HydroSleek), and the like, and mixtures and combinations thereof. Hydrophilic polymers may be blended among themselves or with formulated amounts of water insoluble compounds (including some polymers) to yield coatings with suitable lubricity, bonding, and solubility.

In an implementation, the distal-most end of the distal luminal portion 222 has a flexural stiffness (E*I) in the range of 0.05-0.5 N-mm$^2$ and the remaining portion of the distal luminal portion 222 has a higher flexural stiffness, where E is the elastic modulus and I is the area moment of inertia of the device. These bending stiffness ranges in N-mm$^2$ can be measured by assessing the force in Newtons generated upon deflecting the device a certain distance using a particular gauge length. The bending stiffness (Elastic modulus×area moment of inertia) can be calculated according to the equation $EI=FL^3/3\delta$, where F is deflection force, L is gauge length, and $\delta$ is deflection. For example, using a 3 mm gauge length (L=3 mm) and deflecting a tip of the catheter 2 mm ($\delta$=2 mm), 0.05-0.5 N of force can be generated. In some implementations, the distal-most end of the distal luminal portion 222 can range in bending stiffness between 0.225-2.25 N-mm$^2$. As a comparison, the flexibility of the catheter advancement element 300 based on similar deflection measurements and calculations can be as follows. Upon 2 mm deflection and force gauge length of 3 mm, the catheter advancement element 300 can range in bending force between 0.005-0.05 Newtons or can range in bending stiffness between 0.0225-0.225 N-mm$^2$. Other procedural catheters described herein can have a similar flexibility ranges providing a variable relative stiffness that transitions from the proximal end towards the distal end of the catheter as will be described elsewhere herein and as also described in U.S. Publication No. 2019/0351182, filed May 16, 2019, which is incorporated by reference herein in its entirety.

The catheter 200 can reach anatomic targets with the largest possible internal lumen size for the catheter with the help of the exceedingly flexible catheter advancement element 300. Both the catheter 200 and the catheter advancement element 300, individually and assembled as a system, are configured to navigate around a 180° bend around a radius as small as 0.050" to 0.150" or as small as 0.080" to 0.120" without kinking, for example, to navigate easily through the carotid siphon. The catheter 200 and catheter advancement element 300 can resist kinking and ovalizing even while navigating a tortuous anatomy up to 180°×0.080" radius bend.

In some implementations, the distal luminal portion 222 includes two or more layers. In some implementations, the distal luminal portion 222 includes an inner lubricious liner, a reinforcement layer, and an outer jacket layer. The outer jacket layer may be composed of discreet sections of polymer with different durometers, composition, and/or thickness to vary the flexibility along the length of the distal luminal portion 222. In an implementation, the lubricious inner liner is a PTFE liner, with one or more thicknesses along variable sections of flexibility. In an implementation, the reinforcement layer is a generally tubular structure formed of, for example, a wound ribbon or wire coil or braid. The material for the reinforcement structure may be stainless steel, for example 304 stainless steel, nitinol, cobalt chromium alloy, or other metal alloy that provides the desired combination of strengths, flexibility, and resistance to crush. In an implementation, the reinforcement structure includes multiple materials and/or designs, again to vary the flexibility along the length of the distal luminal portion 222. In an implementation, the outer surface of the catheter 200 is coated with a lubricious coating such as a hydrophilic coating. The proximal control element 230 may also be coated to improve tracking through the working lumen. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinyl alcohols, hydroxy alkyl cellulosics, algins, saccharides, caprolactones, and the like, and mixtures and combinations thereof.

Again with respect to FIGS. 2A-2B, the distal luminal portion 222 of the catheter 200 can have a plurality of radiopaque markers. A first radiopaque marker 224a can be located near the distal tip region to aid in navigation and proper positioning of the tip under fluoroscopy. Additionally, a proximal region of the catheter 200 may have one or more proximal radiopaque markers 224b so that the overlap region 348 can be visualized as the relationship between a radiopaque marker 411 on the guide sheath 400 and the radiopaque marker 224b on the catheter 200. The proximal region of the catheter 200 may also have one or more radiopaque markings providing visualization, for example, of the proximal opening into the single lumen of the catheter as will be described in more detail below. In an implementation, the two radiopaque markers (marker 224a at distal tip and a more proximal marker 224b) are distinct so as to minimize confusion of the fluoroscopic image, for example the catheter proximal marker 224b may be a single band and the marker 411 on the guide sheath 400 may be a double band and any markers on a working device delivered through the distal access system can have another type of band or mark. The radiopaque markers 224 of the distal luminal portion 222, particularly those near the distal tip region navigating extremely tortuous anatomy, can be relatively flexible such that they do not affect the overall flexibility of the distal luminal portion 222 near the distal tip region. The radiopaque markers 224 can be tungsten-loaded or platinum-loaded markers that are relatively flexible compared to other types of radiopaque markers used in devices where flexibility is not paramount. In some implementations, the radiopaque marker can be a band of tungsten-loaded PEBAX having a durometer of 35 D.

Figure 8A:
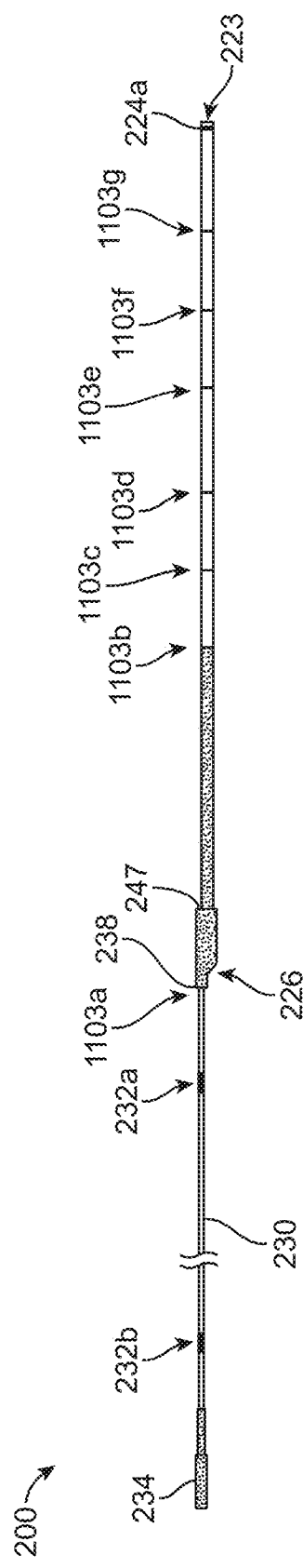
FIG. 8A is a side view of an implementation of a catheter.
Figure 8B:
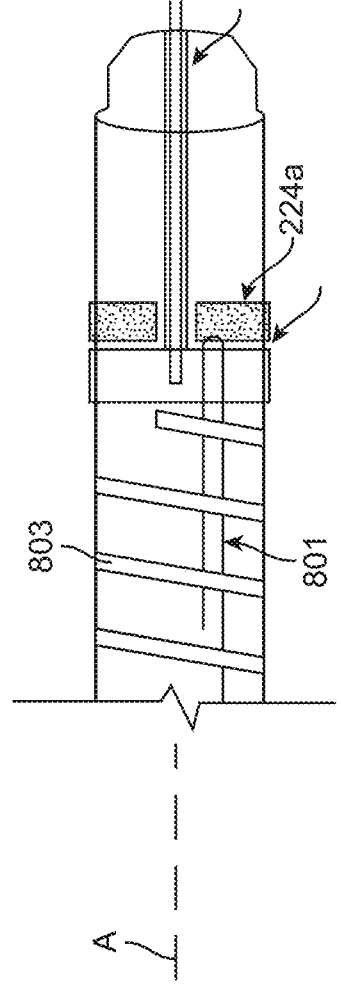
FIG. 8B is a schematic cut-away view of the distal end region of the catheter of FIG. 8A.
Figure 8C:
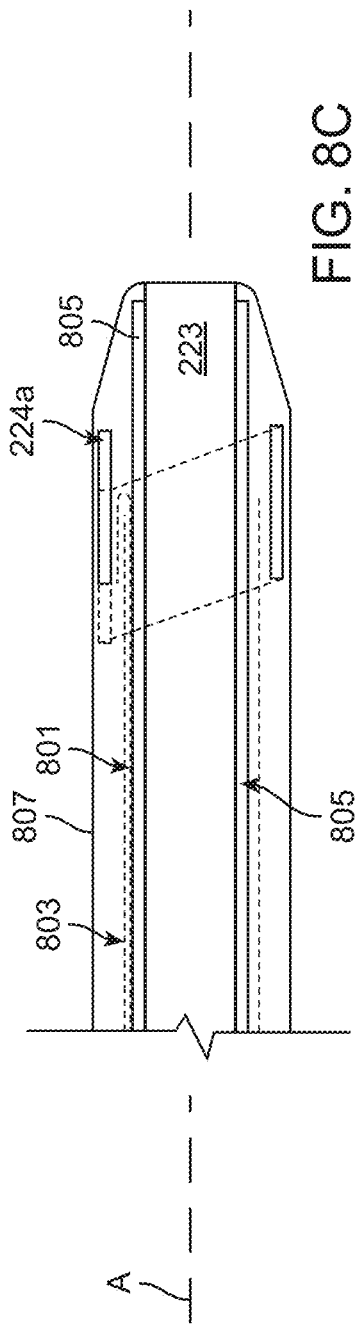
FIG. 8C is a schematic cross-sectional view of the distal end region of the catheter of FIG. 8A.

As best shown in FIGS. 8B-8C, at least one reinforcement fiber 801 can be incorporated within a wall of the distal luminal portion 222 to prevent elongation of a coiled reinforcement layer 803. The fiber 801 can be positioned between the liner layer 805 and the reinforcement layer 803. The fiber 801 can extend along the longitudinal axis A of the catheter 200 from a proximal end region of the distal luminal portion 222 to a distal end region of the portion 222. The proximal end of the fiber 801 can be coupled to a region of the distal luminal portion 222 near where it couples to the proximal extension 230. A distal end of the fiber 801 can terminate near the distal end of the distal luminal portion 222. The distal end of the fiber 801 can be captured between the distal marker band 224a and an end of the reinforcement layer 803. The distal marker band 224a can be fully encapsulated between the inner liner 805 and the outer jacket 807. In some implementations, the distal end of the fiber 801 extends distal to the last coil of the reinforcement layer 803 running under the marker band 224a and then looping around the band 224a back in a proximal direction. The free end of the fiber 801 is thereby captured under the reinforcement layer 803 and the marker band 224a. The reinforcement fiber 801 thus terminates at the location the reinforcement layer 803 terminates thereby leaving a length of between about 10 cm-12 cm of the unreinforced distal-most tip region. The catheter 200 can include a plurality of reinforcement fibers 801 extending longitudinally along the distal luminal portion 222, such as two, three, four, or more fibers 801 distributed around the circumference of the portion 222 and aligned parallel with one another and with the longitudinal axis A of the catheter 200. The reinforcement fiber 801 may also terminate at a more distal location or at a more proximal location than the location of the distal terminal marker 224a. The material of the reinforcement fiber 801 can vary, including but not limited to various high tenacity polymers like polyester, PEEK, and other similar materials.

Figure 9B:
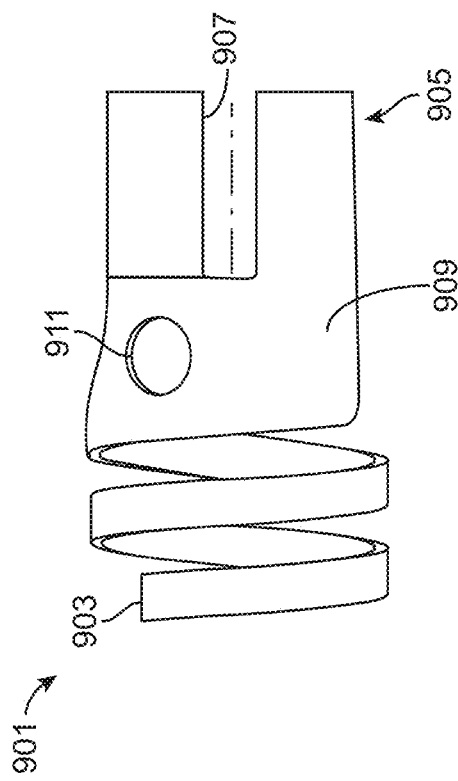
FIG. 9A-9C are various views of a proximal extension connector.
Figure 9C:
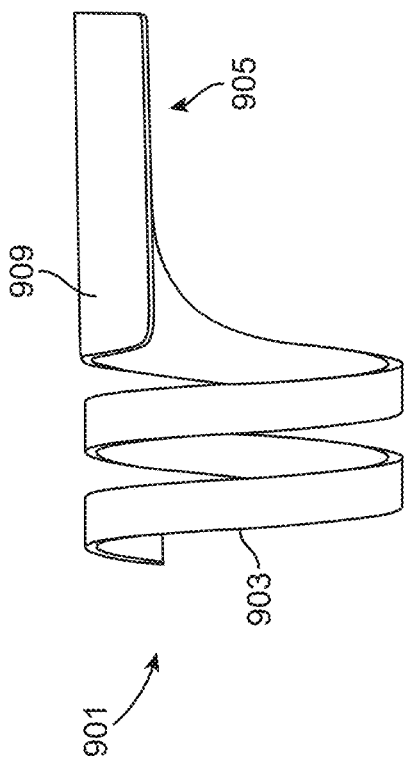
Figure 9A:
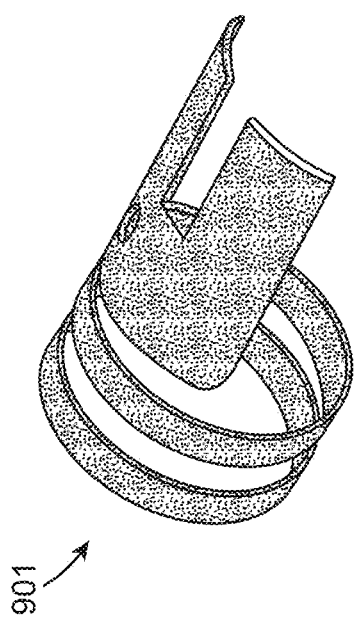

The distal luminal portion 222 of the catheter 200 can have a proximal extension 230 coupled near a proximal opening into the single lumen of the distal luminal portion 222. The distal luminal portion 222 and the proximal extension 230 can be attached to one another by a coupling band 901 (see FIGS. 9A-9C). A proximal end 905 of the coupling band 901 can attach to a distal end of the proximal extension 230 and a distal end of the coupling band 901 can attach to the distal luminal portion 222. The proximal end 905 of the coupling band 901 may include a slot 907 configured to be welded with the proximal extension 230 of the catheter 200. The catheter 200 may include a strain relief along a skive length such as a tungsten loaded PEBAX. The distal end of the coupling band 901 can be cut to form a plurality of spirals 903. These spirals 903 are configured to intersperse with the coils of the reinforcement layer 803 at the proximal end region of the distal luminal portion 222. The size of the gap between the spirals 903 of the coupling band 901 can be substantially similar to the size of the gap between the coils of the reinforcement layer 803 such that they can neatly intersperse with one another without creating any localized areas of increased wall thickness due to overlap. The thickness of the spirals 903 can, but need not, be similar to the thickness of the ribbon forming the reinforcement layer 803. For example, the coiled reinforcement layer 803 can be formed of a Nitinol ribbon having a thickness of about 0.003". The coupling band 901 can have a wall thickness that is about 0.003" such that the spirals 903 and the coils of the reinforcement layer 803 can be similar in material thickness. This similarity in material thickness between the coils and the spirals 903 contribute to a generally uniform outer profile that can be kept to a minimum and avoid creating a substantially increased wall thickness in this coupling region. A low profile proximal end of the distal luminal portion 222 aids in maximizing the inner diameter while keeping the outer diameter as small as possible, for example, such that the inner diameter of the guide sheath to a minimum (e.g. less than about 0.113" or about 0.107"). The coupling band 901 can include an aperture 911 through middle region 909 that is configured to receive a proximal end of the reinforcement fiber 801 extending longitudinally through the distal luminal portion 222. The region of overlap between the distal end of the proximal control element and the distal luminal portion 222 can vary, but can be at least about 5 mm, at least about 7 mm, at least about 10 mm to provide a smooth and even transition. The overlap between the proximal control element and the distal luminal portion 222 may be about 5 mm up to about 15 mm.

As mentioned above the distal end of the proximal extension 230 can be welded to the proximal end 905 of the coupling band 901. In some implementations, the distal end region of the proximal extension 230 is skived in places and is flat in other places. The proximal extension 230 can be a stainless steel ribbon (e.g. 0.012"×0.020" or 0.014"×0.020" along a majority of its length). A distal end region of the proximal extension 230 can have a discontinuous taper that allows for the thickness of the ribbon to transition from the thickness of 0.012" or 0.014" down to a thickness that matches or is not significantly different from a thickness of the spirals 903 on the coupling band 901 that is attached to a proximal end region of the distal luminal portion 222. The discontinuous taper can include a flat length bound on proximal and distal ends by a tapered length. The flat length allows for a more uniform, minimum material thickness between the distal luminal portion 222 and the proximal extension 230 that avoids introducing weak points that are more prone to kinking. For example, the distal end region of the proximal extension 230 can have a first tapered length that transitions in thickness from 0.012" to a thickness of 0.008" and a second tapered length that transitions from the flat length thickness down to about 0.003". In other implementations, the distal end region of the proximal extension 230 can have a first tapered length that transitions in thickness from 0.014" to a thickness of 0.010" and a second tapered length that transitions from the flat length thickness down to about 0.003". The spirals 903 of the coupling band 901 can have a thickness matches this terminal thickness of the proximal extension 230. The lengths of the tapered and flat portions can vary. In some implementations, the first tapered length can be approximately 0.12 cm, the flat length can be approximately 0.2 cm, and the second tapered length can be approximately 0.15 cm. The uniform thickness along this flat length provides for a useful target in terms of manufacturing the catheter. The catheter need not incorporate a ribbon proximal extension 230 and can have any of a variety of configuration as described elsewhere herein.

As mentioned previously, the proximal extension 230 is configured to allow distal advancement and proximal retraction of the catheter 200 through the working lumen of the guide sheath 400 including passage out the distal lumen 408. In an implementation, the length of the proximal extension 230 is longer than the entire length of the guide sheath 400 (from distal tip to proximal valve), such as by about 5 cm to 15 cm. The length of the body 402 can be in the range of 80 to 90 cm or up to about 100 cm or up to about 105 cm and the length of the proximal extension 230 can be between 90-100 cm.

Again with respect to FIG. 3, the proximal extension 230 can include one or more markers 232 to indicate the overlap between the distal luminal portion 222 of the catheter 200 and the sheath body 402 as well as the overlap between the distal luminal portion 222 of the catheter 200 and other interventional devices that may extend through the distal luminal portion 222. At least a first mark 232a can be an RHV proximity marker positioned so that when the mark 232a is aligned with the sheath proximal hemostasis valve 434 during insertion of the catheter 200 through the guide sheath 400, the catheter 200 is positioned at the distal-most position with the minimal overlap length needed to create the seal between the catheter 200 and the working lumen. At least a second mark 232b can be a Fluoro-saver marker that can be positioned on the proximal extension 230 and located a distance away from the distal tip of the distal luminal portion 222. In some implementations, a mark 232 can be positioned about 100 cm away from the distal tip of the distal luminal portion 222.

The proximal extension 230 can include a gripping feature such as a tab 234 on the proximal end to make the proximal extension 230 easy to grasp and advance or retract. The tab 234 can couple with one or more other components of the system as will be described in more detail below. The proximal tab 234 can be designed to be easily identifiable amongst any other devices that may be inserted in the sheath proximal valve 434, such as guidewires or retrievable stent device wires. A portion of the proximal extension 230 and/or tab 234 can be colored a bright color, or marked with a bright color, to make it easily distinguishable from guidewire, retrievable stent tethers, or the like. Where multiple catheters 200 are used together in a nesting fashion to reach more distal locations within the brain, each proximal extension 230 and/or tab 234 can be color-coded or otherwise labeled to clearly show to an operator which proximal extension 230 of which catheter 200 it is coupled to. The proximal portion 366 of the catheter advancement element 300 can also include a color to distinguish it from the proximal extension 230 of the catheter 200.

The tab 234 can be integrated with or in addition to a proximal hub coupled to a proximal end of the proximal extension 230. For example, as will be described in more detail below, the proximal extension 230 can be a hypotube having a lumen. The lumen of the hypotube can be in fluid communication with the proximal hub at a proximal end of the proximal extension 230 such that aspiration forces and/or fluids can be delivered through the hypotube via the proximal hub. The proximal control element 230 can also be a solid element and need not include a lumen to direct aspiration forces to the distal end of the catheter 200.

The proximal extension 230 can be configured with sufficient stiffness to allow advancement and retraction of the distal luminal portion 222 of the catheter 200, yet also be flexible enough to navigate through the cerebral anatomy as needed without kinking. The configuration of the proximal extension 230 can vary. In some implementations, the proximal extension 230 can be a tubular element having an outer diameter that is substantially identical to the outer diameter of the distal luminal portion 222 similar to a typical catheter device. In other implementations, the outer diameter of the proximal extension 230 is sized to avoid taking up too much luminal area in the lumen of the guide sheath 400 as described above.

Figure 4G:
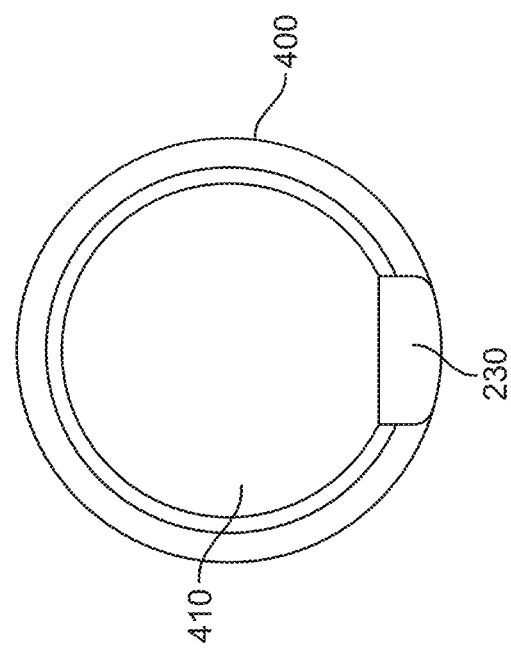
FIGS. 4F-4G are cross-sectional, schematic views comparing trapezoid- and D-shaped proximal extensions, respectively, relative to a working lumen of an access sheath.
Figure 4F:
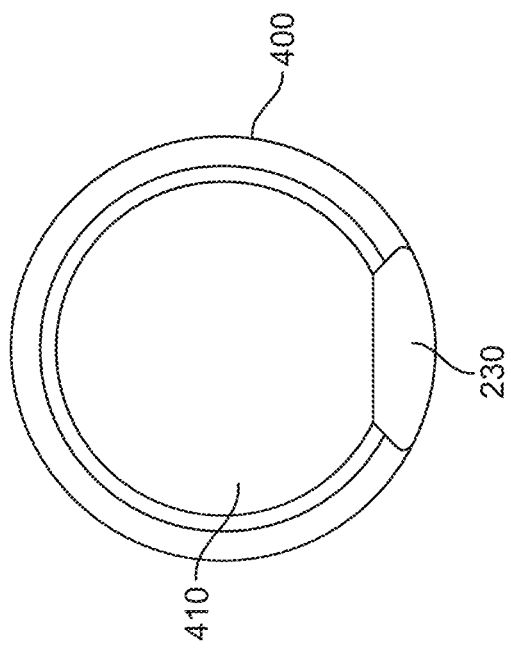

The proximal extension 230 can be a solid metal wire that is round, rectangular, trapezoid, D-shape, or oval cross-sectional shape (see FIGS. 4A-4G). The proximal extension 230 can be a flattened ribbon of wire having a rectangular cross-sectional shape as shown in FIG. 4A. The flattened ribbon of wire can also have square, rectangular, or other cross-sectional shape. The ribbon of wire can be curved into a circular, oval, c-shape, or quarter circle or other cross-sectional area along an arc. As such, an inner-facing surface of the ribbon can be substantially flat and an outer-facing surface of the ribbon (i.e. the surface configured to abut against an inner diameter of the access sheath through which it extends) can be substantially curved (see FIGS. 4F-4G). The curvature of the surface can substantially match the curvature of the inner surface of the access sheath. The resulting cross-sectional shape of such a ribbon can be generally trapezoidal. The overall dimensions of the ribbon can vary depending on its cross-sectional shape and the size of the distal luminal portion. The 0.054" sized catheter 200 can have a proximal extension 230 that is trapezoidal or D-shaped in cross-section. The inner-facing, flat surface can have a width that is approximately 0.020" wide and in the case of the trapezoidal-shaped implementation, the outer-facing, curved surface can extend along an arc that is approximately 0.030" long. The 0.070" sized catheter 200 can have a proximal extension that is trapezoidal or D-shaped in cross-section, and the width of the inner-facing, flat surface is slightly greater, for example, approximately 0.025" and in the case of the trapezoidal-shaped implementation, the outer-facing, curved surface can extend along an arc that is approximately 0.040" long. The 0.088" sized catheter 200 can have a proximal extension that is trapezoidal or D-shaped in cross-section, and the width of the inner-facing, flat surface is approximately 0.035" and the outer-facing, curved surface of the trapezoidal-shaped implementation can extend along an arc that is approximately 0.050" long.

The proximal extension 230 can be a hollow wire having a lumen 235 extending through it, such as a hypotube as shown in FIG. 4B. The hypotube can have an oval or circular shape. In an implementation, the proximal extension 230 is a ribbon of stainless steel having dimensions of about 0.012"×0.020". In an implementation, the proximal extension 230 is a ribbon of stainless steel having dimensions of about 0.014"×0.020". In an implementation, the proximal extension 230 is a round wire, with dimensions from 0.014" to 0.018". In another implementation, the proximal extension 230 is a ribbon with dimensions ranging from 0.010" to 0.015" thick, and 0.015" thick to 0.025" thick. In an implementation, the proximal extension 230 is a hypotube formed from a flattened ribbon of stiff material rolled into a tubular shape to have a lumen 235 with or without a polymer jacket and/or liner. In some implementations, the proximal extension 230 can be formed of a flattened ribbon of stainless steel and rolled into a hypotube such that the proximal extension 230 has a wall thickness of about 0.007", an inner diameter of about 0.004" and an outer diameter of about 0.018" before the hypotube is modified into an oval cross-sectional shape. The ovalized hypotube can maintain an inner diameter that is at least 0.001" along at least a first dimension and an outer diameter that is at least 0.015" along at least a first dimension. In an implementation, the proximal extension 230 material is a metal such as a stainless steel or Nitinol as well as a plastic such as any of a variety of polymers. In an implementation, the proximal extension 230 is a stainless steel hypotube having an oval cross-sectional shape (see FIG. 4B). The oval tubular shape can increase the column strength, pushability and kink resistance of the proximal extension 230 for improved advancement through tortuous anatomy. The cross-sectional area of an oval hypotube minimizes the impact of the catheter 200 on movement of other tools through the working lumen of the sheath 400. FIG. 4C illustrates a cross-sectional view of the working lumen of the sheath 400 having a proximal portion 230 extending therethrough. The proximal portion 230 has a rectangular cross-sectional shape. FIG. 4D illustrates a cross-sectional view of the working lumen having an ovalized hypotube proximal portion 230 and a catheter advancement element 300 extending therethrough. FIG. 4E illustrates the comparison of surface area between the rectangular-shaped ribbon and the oval hypotube. The oval hypotube has less surface area compared to the rectangular-shaped ribbon allowing for a greater flow rate through the working lumen, for example, during application of aspirating forces. The materials, dimensions, and shape of the proximal extension 230 can be selected based on the materials, dimensions, and shape of the distal luminal portion 222. For example, the proximal extension 230 can be a rectangular ribbon of 340 stainless steel that is 0.012"×0.020" and the distal luminal portion 222 can have an inner diameter of about 0.054" to about 0.072". In a further implementation, the proximal extension 230 can be a rectangular ribbon of 340 stainless steel that is 0.014"×0.020" and the distal luminal portion 222 can have an inner diameter of about 0.088". The additional heft of the stainless steel ribbon 230 can be useful in advancing a larger inner diameter catheter without kinking. If the proximal portion 230 is formed by a hypotube, the hypotube can be solid hypotube without interruptions through its sidewall or can incorporate an interruption or perforation through the sidewall such as a cut in one or more locations.

Now with respect to FIGS. 5A-5F, the junction between the distal luminal portion 222 of the catheter 200 and the proximal extension 230 can be configured to allow a smooth transition of flexibility between the two portions so as not to create a kink or weak point. The smooth transition at the joint between the distal luminal portion 222 and the proximal extension 230 also allows for smooth passage of devices through the contiguous inner lumen created by the working lumen of the guide sheath 400 and the lumen 223 of the luminal portion 222 of the catheter 200. In an implementation, the distal luminal portion 222 has a transition section 226 near where the luminal portion 222 couples to the proximal extension 230 (see FIG. 5A). The transition section 226 can have an angled cut such that there is no abrupt step transition from the working lumen of the guide sheath 400 to the inner lumen 223 of the catheter 200. The angled cut can be generally planer. In an alternate implementation, the angled cut is curved or stepped to provide a more gradual transition zone. The proximal end region of the distal luminal portion 222 can be angled in an oblique manner relative to a longitudinal axis of the catheter 200 such that the proximal end and proximal opening into the lumen are at an angle other than 90° to the longitudinal axis of the catheter 200, for example between approximately 0°, 5°, 10°, 15°, 20°, 25°, 30°, 35°, 40°, or 45° up to less than 90°. The proximal end region of the distal luminal portion 222 can also be aligned substantially perpendicular to the longitudinal axis of the catheter 200 such that the proximal end and proximal opening into the lumen are substantially 90° to the longitudinal axis of the catheter 200. Similarly, the distal end region of the distal luminal portion 222 can be angled in an oblique manner relative to a longitudinal axis of the catheter 200 such that the distal end and distal opening from the lumen 223 are at an angle other than 90° to the longitudinal axis of the catheter 200, for example between approximately 0°, 5°, 10°, 15°, 20°, 25°, 30°, 35°, 40°, or 45° up to less than 90°. The distal end region of the distal luminal portion 222 can also be aligned substantially perpendicular to the longitudinal axis of the catheter 200 such that the distal end and distal opening into the lumen are substantially 90° to the longitudinal axis of the catheter 200.

The proximal extension 230 can be coupled to a proximal end region of the catheter 200 and/or may extend along at least a portion of the distal luminal portion 222 such that the proximal extension 230 couples to the distal luminal portion 222 a distance away from the proximal end. The proximal extension 230 can be coupled to the distal luminal portion 222 by a variety of mechanisms including bonding, welding, gluing, sandwiching, stringing, tethering, or tying one or more components making up the proximal extension 230 and/or portion 222. The distal luminal portion 222 and the proximal extension 230 may be joined by a weld bond, a mechanical bond, an adhesive bond, or some combination thereof. In some implementations, the proximal extension 230 and luminal portion 222 are coupled together by sandwiching the proximal extension 230 between layers of the distal luminal portion 222. For example, the proximal extension 230 can be a hypotube or rod having a distal end that is skived, ground or cut such that the distal end can be laminated or otherwise attached to the layers of the catheter portion 222 near a proximal end region. The skive length of the proximal control element 230 can be about 7 mm and can incorporate a tungsten loaded Pebax strain relief along the length. The region of overlap between the distal end of the proximal extension 230 and the portion 222 can be at least about 1 cm. This type of coupling allows for a smooth and even transition from the proximal extension 230 to the luminal portion 222.

Still with respect to FIGS. 5A-5F, the transition section 226 of the distal luminal portion 222 can open up into a trough 238 extending a length proximal to the transition section 226. In some implementations, the trough 238 has a cross-sectional geometry that is substantially curved. For example, the trough 238 can extend along an arc of the longitudinal axis of the catheter 200 between about 20 to about 90 degrees. In some implementations, the trough 238 is curved to create a funnel-shape and aids in loading and reloading a catheter advancement element 300 into the lumen of the catheter 200. In other implementations, the edges of the trough 238 curve such that the trough 238 is not substantially flat. The curved shape can vary including a tear-drop shape that allows for a smooth transition and better loading/reloading of the catheter advancement element 300 into the lumen and avoids flat edges that can abut and catch the component as it is inserted. In other implementations, the trough 238 is substantially flat. The trough 238 can provide a smooth transition between distal luminal portion 222 and proximal extension 230 when the device is forced to bend. This can reduce the likelihood of kinking and facilitate pushing against resistance.

The dimensions of the proximal tail 238 can vary. The proximal tail 238 shown in FIGS. 5A-5F is relatively wide compared to the width of the proximal control element 230 and, in turn, can have a greater length without negatively impacting the ability of other devices to insert through the proximal opening into the lumen at the transition region 226. In other implementations, the proximal tail 238, defined by a region that is unsupported by the coils of the reinforcement layer 803 and located proximal to the coupling band 901, can have a shorter length. The width of this proximal tail 238 can taper along this shorter length to a width of the proximal control element 230. The tapered shorter proximal tail 238 can mitigate issues with insertion of tools into the proximal opening. Generally speaking, wide proximal tails 238 can be longer than proximal tails 238 that taper down to the width of the proximal control element 230.

A proximal region of the distal luminal portion 222 can incorporate one or more markers to provide visualization under fluoro during loading/reloading of the catheter advancement element 300. For example, the proximal end region can include a region of Pebax (e.g. 35 D) loaded with tungsten (80%) for radiopacity. In some implementations, the proximal tail 228 and/or the transition section 226 defining the proximal opening into the lumen of the luminal portion 222 can be coated or embedded with a radiopaque material such that the opening into the lumen can be fully visualized during use. The radiopaque material embedded in this proximal end region can create a step-up in outer diameter.

The distal end of the proximal extension 230 and/or the distal luminal portion 222 may have features that facilitate a mechanical joint during a weld, such as a textured surface, protruding features, or cut-out features. During a heat weld process, the features would facilitate a mechanical bond between the polymer distal luminal portion 222 and the proximal extension 230. For example, as shown in FIGS. 6A-6F the proximal end of the distal luminal portion 222 can include a short mating sleeve 240 coupled to a proximal edge 221 of the distal luminal portion 222. The sleeve 240 can include an inner lumen extending between a proximal opening 242 and a distal opening 241. The distal end of the proximal extension 230 can insert through the proximal opening 242 and within the inner lumen of the sleeve 240 to couple the proximal extension 230 to the distal luminal portion 222. In some implementations, the proximal extension 230 can couple with the distal luminal portion 222 such that a distal opening 231 of the hypotube forming the proximal extension 230 can communicate with the lumen 223 of the distal luminal portion 222, for example, through the distal opening 241 of the sleeve 240. The sleeve 240 can also provide transition between distal luminal portion 222 and proximal extension 230 similar to the trough 238. The distal luminal portion 222 need not include a mating sleeve 240 to couple with the proximal extension 230. For example, the distal end of the proximal extension 230 can insert through a wall of the trough 238 at the proximal end of the distal luminal portion 222 (see FIG. 5A, 5E-5F). The distal end of the proximal extension 230 can extend along the length of the trough 238 and along at least a length of the wall of the distal luminal portion 222.

The luminal portion 222 of the catheter 200 can have a uniform diameter or wall thickness from a proximal end to a distal end or the luminal portion 222 can have different outer diameters or wall thicknesses along its length. For example, the distal-most end of the distal luminal portion 222 can have a smaller outer diameter compared to a more proximal region of the distal luminal portion 222. FIGS. 5A-5B, 5E-5F as well as FIGS. 6A-6B, 6E-6F, and FIG. 8A show a distal luminal portion 222 having a distal tubular region or distal tube 245 having a smaller outer diameter and a proximal tubular region or proximal tube 246 have a larger outer diameter. The distal tube 245 transitions via a step-up 247 to the proximal tube 246. As best shown in FIGS. 5A and 6A, the inner diameters of distal tube 245 and the proximal tube 246 are substantially the same providing a smooth inner wall surface for the lumen 223. The outer diameter of the distal tube 245 may be smaller than the outer diameter of the proximal tube 246. The step-up 247 is formed by a transition in wall thickness between the distal tube 245 and the proximal tube 246. In some implementations, the outer diameter of the distal tube 245 can be about 0.080" to about 0.084" and the outer diameter of the proximal tube 246 can be about 0.087" to about 0.088". In other implementations, the outer diameter of the proximal tube 246 can be 0.106" to about 0.107". The relative lengths of the proximal and distal tubes 245, 246 may vary as described elsewhere herein. For example, the proximal tube 246 can create a proximal sealing zone that is a cylindrical segment having a length that is about 1 mm, 2 mm, 3 mm, 4 mm, 5 mm, up to about 10 mm, or 15 mm. The proximal sealing zone of the proximal tube 246 may have a larger OD compared to the OD of the distal tube. In some implementations, the distal tube may have an OD that is about 0.082", the proximal tube 246 at the proximal sealing zone may have an OD that is about 0.087". In other implementations, where the distal tube may have an OD that is about 0.102", and the proximal tube 246 at the proximal sealing zone may have an OD that is about 0.105".

At least a portion of the wall of the larger outer diameter proximal tube 246 can be discontinuous such that it includes a slit 236 (see FIGS. 5A-5C, 5E-5F, 6A-6C, and 6E-6F). The slit 236 can extend a distance along the length of the proximal tube 246. The slit 236 can extend from an edge 221 of the proximal tube 246 at least about 2 cm of a length of the proximal tube 246. The slit 236 can, but need not, extend along the entire length of the proximal tube 246 to the location of the step-up 247. Additionally, the proximal tube 246 can include more than one slit 236. The slit 236 can be positioned in the larger diameter proximal tube 246 at a location opposite from where the distal end of the proximal extension 230 couples with the wall of the distal luminal portion 222. As such that distal end of the proximal extension 230 embedded within the wall of the proximal tube 246 lies opposite the slit 236 (see FIGS. 5C and 6C). The slit 236 can be positioned around the proximal tube 246 at another location.

The slit 236 can allow for the proximal tube 246 to expand slightly such that the ends of the wall forming the slit 236 separate forming a gap therebetween. For example, upon insertion of the catheter 200 through the working lumen of the sheath 400, the outer diameter can be received in a sliding fit such that at least an overlap region 348 remains. Upon application of an aspirational force through the working lumen, for example, by applying suction from an aspiration source coupled to the proximal end 403 of the guide sheath 400, the sealing provided at the overlap region 348 can be enhanced by a slight widening of the gap formed by the slit 236. This slight expansion provides for better sealing between the outer diameter of the proximal tube 246 and the inner diameter of the working lumen of the sheath 400 because the outer surface of the walls of the catheter 200 can press against the inner surface of the working lumen creating a tight fit between the catheter 200 and the sheath 400. This improved sealing between the outer surface of the catheter 200 and the inner surface of the working lumen minimizes the seepage of blood from the vessel into the working lumen directly through the distal opening 408. Thus, the larger outer diameter of the proximal tube 246 in combination with the slit 236 can enhance sealing between the catheter 200 and the sheath 400 by accommodating for variations of sheath inner diameters. The slit 236 can effectively increase the outer diameter of the proximal tube 246 depending on whether the walls forming the slit 236 are separated a distance. The walls forming the slit 236 can separate away from one another and increase a width of slit. The outer diameter of the proximal tube 246 including the increased width upon separation of the walls forming the slit 236 can be the same size or larger than the inner diameter of the sheath through which the proximal tube 246 is inserted. This allows for a single catheter to be compatible with a larger range of inner diameters. In some implementations, the outer diameter of the proximal tube 246 can be 0.081" or about 0.100" when the walls forming the slit 236 abut one another and no gap is present. The outer diameter of the proximal tube 246 can increase up to about 0.087" or up to about 0.106" when the walls forming the slit 236 are separated a maximum distance away from one another. Additionally, the increased wall thickness of the proximal tube 246 allows for creating a more robust joint between the distal luminal portion 222 and the proximal extension 230 of the catheter.

Additionally or alternatively, the distal tip 406 of the sheath 400 can include one or more features that improve sealing between the inner diameter of the working lumen of the sheath 400 and the outer diameter of the proximal end region of the catheter 200, as described elsewhere herein.

Catheter Advancement Element

As mentioned above, the distal access system 100 can, but need not, include a catheter advancement element 300 for delivery of the catheter 200 to the distal anatomy. Where the catheter 200 is described herein as being used together or advanced with the catheter advancement element 300 that the catheter advancement element 300 need not be used to deliver the catheter 200 to a target location. For example, other advancement tools are to be considered herein, such as a microcatheter and/or guidewire as is known in the art. Similarly, the catheter advancement element 300 can be used together to advance other catheters besides the catheter 200 described herein. For example, the catheter advancement element 300 can be used to deliver a 5MAX Reperfusion Catheter (Penumbra, Inc. Alameda, Calif.) for clot removal in patients with acute ischemic stroke or other reperfusion catheters known in the art. Although the catheter advancement element 300 is described herein in reference to catheter 200 it can be used to advance other catheters and it is not intended to be limiting to its use.

As described above, the distal access system 100 is capable of providing quick and simple access to distal target anatomy, particularly the tortuous anatomy of the cerebral vasculature. The flexibility and deliverability of the distal access catheter 200 allow the catheter 200 to take the shape of the tortuous anatomy and avoids exerting straightening forces creating new anatomy. The distal access catheter 200 is capable of this even in the presence of the catheter advancement element 300 extending through its lumen. Thus, the flexibility and deliverability of the catheter advancement element 300 is on par or better than the flexibility and deliverability of the distal luminal portion 222 of the distal access catheter 200 in that both are configured to reach the middle cerebral artery (MCA) circulation without straightening out the curves of the anatomy along the way.

The catheter advancement element 300 can include a non-expandable, flexible elongate body 360 coupled to a proximal portion 366. The catheter advancement element 300 and the catheter 200 described herein may be configured for rapid exchange or over-the-wire methods. For example, the flexible elongate body 360 can be a tubular portion extending the entire length of the catheter advancement element 300 and can have a proximal opening from the lumen of the flexible elongate body 360 that is configured to extend outside the patient's body during use. Alternatively, the tubular portion can have a proximal opening positioned such that the proximal opening remains inside the patient's body during use. The proximal portion 366 can be a proximal element coupled to a distal tubular portion and extending proximally therefrom. A proximal opening from the tubular portion can be positioned near where the proximal element couples to the tubular portion. Alternatively, the proximal portion 366 can be a proximal extension of the tubular portion having a length that extends to a proximal opening near a proximal terminus of the catheter advancement element 300 (i.e. outside a patient's body).

The configuration of the proximal portion 366 can vary. In some implementations, the proximal portion 366 is simply a proximal extension of the flexible elongate body 360 that does not change significantly in structure but in flexibility. For example, the proximal portion 366 transitions from the very flexible distal regions of the catheter advancement element 300 towards less flexible proximal regions of the catheter advancement element 300. The proximal portion 366 provides a relatively stiff proximal end suitable for manipulating and torqueing the more distal regions of the catheter advancement element 300. In other implementations, the proximal portion 366 is a hypotube. The hypotube may be exposed or may be coated by a polymer. In still further implementations, the proximal portion 366 may be a polymer portion reinforced by a coiled ribbon. The proximal portion 366 can have the same outer diameter as the flexible elongate body or can have a smaller outer diameter as the flexible elongate body.

The proximal portion 366 need not include a lumen. For example, the proximal portion 366 can be a solid rod, ribbon, or wire have no lumen extending through it that couples to the tubular elongate body 360. Where the proximal portion 366 is described herein as having a lumen, it should be appreciated that the proximal portion 366 can also be solid and have no lumen. The proximal portion 366 is generally less flexible than the elongate body 360 and can transition to be even more stiff towards the proximal-most end of the proximal portion 366. Thus, the catheter advancement element 300 can have an extremely soft and flexible distal-most tip that transitions proximally to a stiff proximal portion 366 well suited for torqueing and pushing the distal elongate body 360. The transition in flexibility of the catheter advancement element 300 and the system as a whole is described in more detail below.

The elongate body 360 can be received within and extended through the internal lumen 223 of the distal luminal portion 222 of the catheter 200 (see FIG. 2B). The elongate body 360 or tubular portion can have an outer diameter. The outer diameter of the tubular portion can have at least one snug point, a difference between the inner diameter of the catheter 200 and the outer diameter of the tubular portion at the snug point can be no more than about 0.010", for example, from 0.003" up to about 0.010", preferably about 0.006" to about 0.008". As will be described in more detail below, the catheter advancement element 300 can also include a tip portion or distal tip 346 located distal to the at least one snug point of the tubular portion. The tip portion can have a length and taper along at least a portion of the length. The distal tip 346 of the catheter advancement element 300 can be extended beyond the distal end of the catheter 200 as shown in FIG. 2B. The proximal portion 366 of the catheter advancement element 300 is coupled to a proximal end region of the elongate body 360 and extends proximally therefrom. The proximal portion 366 can be less flexible than the elongate body 360 and configured for bi-directional movement of the elongate body 360 of the catheter advancement element 300 within the luminal portion 222 of the catheter 200, as well as for movement of the catheter system 100 as a whole. The elongate body 360 can be inserted in a coaxial fashion through the internal lumen 223 of the luminal portion 222. The outer diameter of at least a region of the elongate body 360 can be sized to substantially fill at least a portion of the internal lumen 223 of the luminal portion 222.

The overall length of the catheter advancement element 300 (e.g. between the proximal end through to the distal-most tip) can vary, but generally is long enough to extend through the support catheter 200 plus at least a distance beyond the distal end of the support catheter 200 while at least a length of the proximal portion 366 remains outside the proximal end of the guide sheath 400. In some implementations, the overall length of the catheter advancement element 300 is about 145 to about 150 cm and has a working length of 140 cm to about 145 cm from a proximal tab or hub to the distal-most tip. The elongate body 360 can have a length that is at least as long as the luminal portion 222 of the catheter 200 although the elongate body 360 can be shorter than the luminal portion 222 so long as at least a length remains inside the luminal portion 222 when a distal portion of the elongate body 360 is extended distal to the distal end of the luminal portion 222. In some implementations, this minimum length of the elongate body 360 that remains inside the luminal portion 222 when the distal tip 346 is positioned at its optimal advancement configuration is at least about 5 cm, at least about 6 cm, at least about 7 cm, at least about 8 cm, at least about 9 cm, at least about 10 cm, at least about 11 cm, or at least about 12 cm up to about 50 cm. In some implementations, the shaft length of the distal luminal portion 222 can be about 35 cm up to about 75 cm and shorter than a working length of the guide sheath and the insert length of the elongate body 360 can be at least about 45 cm, 46 cm, 47 cm, 48 cm, 48.5 cm, 49 cm, 49.5 cm, up to about 85 cm.

The length of the elongate body 360 can allow for the distal end of the elongate body 360 to reach cerebrovascular targets within, for example, the M1 or M2 regions while the proximal end region of the elongate body 360 remains proximal to or below the level of severe turns along the path of insertion. For example, the entry location of the catheter system can be in the femoral artery and the target embolus can be distal to the right common carotid RCC artery, such as within the M1 segment of the middle cerebral artery on the right side. The proximal end region of the elongate body 360 where it transitions to the proximal portion 366 can remain within a vessel that is proximal to severely tortuous anatomy such as the carotid siphon, the right common carotid RCC artery, the brachiocephalic trunk BT, the take-off into the brachiocephalic artery from the aortic arch, the aortic arch AA as it transitions from the descending aorta DA. This avoids inserting the stiffer proximal portion 366, or the material transition between the stiffer proximal portion 366 and the elongate body 360, from taking the turn of the aortic arch or the turn of the brachiocephalic take-off from the aortic arch, which both can be very severe. The lengths described herein for the distal luminal portion 222 also can apply to the elongate body 360 of the catheter advancement element.

The proximal portion 366 can have a length that varies as well. In some implementations, the proximal portion 366 is about 90 cm up to about 95 cm. The distal portion extending distal to the distal end of the luminal portion 222 can include distal tip 346 that protrudes a length beyond the distal end of the luminal portion 222 during use of the catheter advancement element 300. The distal tip 346 of the elongate body 360 that is configured to protrude distally from the distal end of the luminal portion 222 aids in the navigation of the catheter system through the tortuous anatomy of the cerebral vessels, as will be described in more detail below. The proximal portion 366 coupled to and extending proximally from the elongate body 360 can align generally side-by-side with the proximal extension 230 of the catheter 200. The arrangement between the elongate body 360 and the luminal portion 222 can be maintained during advancement of the catheter 200 through the tortuous anatomy to reach the target location for treatment in the distal vessels and aids in preventing the distal end of the catheter 200 from catching on tortuous branching vessels, as will be described in more detail below.

In some implementations, the elongate body 360 can have a region of relatively uniform outer diameter extending along at least a portion of its length and the distal tip 346 tapers down from the uniform outer diameter. The outer diameter of the elongate body 360 can include a step-down at a location along its length, for example, a step-down in outer diameter at a proximal end region where the elongate body 360 couples to the proximal portion 366. Depending upon the inner diameter of the catheter 200, the clearance between the catheter 200 and the outer diameter of the elongate body 360 along at least a portion of its length can be no more than about 0.010", such as within a range of about 0.003"-0.010" or between 0.006"-0.008".

The elongate body 360 can have an overall shape profile from proximal end to distal end that transitions from a first outer diameter having a first length to a tapering outer diameter having a second length. The first length of this first outer diameter region (i.e. the snug-fitting region between the distal luminal portion 222 and the elongate body 360) can be at least about 5 cm, or 10 cm, up to about 50 cm. The length of the tapering outer diameter can be between 1 cm and 4 cm. When the catheter advancement element 300 is inserted through the catheter 200, this tapered distal tip 346 is configured to extend beyond and protrude out through the distal end of the luminal portion 222 whereas the more proximal region of the body 360 having a uniform diameter remains within the luminal portion 222. As mentioned, the distal end of the luminal portion 222 can be blunt and have no change in the dimension of the outer diameter whereas the distal tip 346 can be tapered providing an overall elongated tapered geometry of the catheter system. The outer diameter of the elongate body 360 also approaches the inner diameter of the luminal portion 222 such that the step up from the elongate body 360 to the outer diameter of the luminal portion 222 is minimized. Minimizing this step up prevents issues with the lip formed by the distal end of the luminal portion 222 catching on the tortuous neurovasculature, such as around the carotid siphon near the ophthalmic artery branch, when the distal tip 346 bends and curves along within the vascular anatomy. In some implementations, the inner diameter of the luminal portion 222 can be at least about 0.052", about 0.054" and the maximum outer diameter of the elongate body 360 can be about 0.048" such that the difference between them is about 0.006". In some implementations, the inner diameter of the luminal portion 222 can be 0.070" and the outer diameter of the elongate body 360 can be 0.062" such that the difference between them is about 0.008". In some implementations, the inner diameter of the luminal portion 222 can be 0.088" and the outer diameter of the elongate body 360 can be 0.080" such that the difference between them is about 0.008". In some implementations, the inner diameter of the luminal portion 222 can be 0.072" and the outer diameter of the elongate body 360 is 0.070" such that the difference between them is about 0.002". In other implementations, the outer diameter of the elongate body 360 is 0.062" such that the difference between them is about 0.010". Despite the outer diameter of the elongate body 360 extending through the lumen of the luminal portion 222, the luminal portion 222 and the elongate body 360 extending through it in co-axial fashion are flexible enough to navigate the tortuous anatomy leading to the level of M1 or M2 arteries without kinking and without damaging the vessel.

As mentioned above, each of the distal luminal portion 222 of the catheter 200 and the elongate body 360 of the catheter advancement element 300 are capable of bending up to about 180 degrees without kinking or ovalizing such that they can be folded over onto themselves forming an inner and an outer radius of curvature. Additionally, the combined system of the elongate body 360 extending through the lumen of the distal luminal portion 222 maintains this high degree of flexibility when the components are assembled into a coaxial system. The two components as a system can be folded and maintain similar flexibility as each component individually. The radius of curvature of the folded system is comparable to the radius of curvature of the components individually. The flexibility of the two components when assembled together as a system allows for the system to be folded over on top of itself such that a width across the catheter bodies is less than a minimum width without kinking or ovalizing. As an example, the distal luminal portion 222 can have an outer diameter of about 0.082" and an inner diameter of about 0.071". A catheter advancement element 300 inserted through the distal luminal portion 222 can have an outer diameter of about 0.062" substantially filling the inner diameter of the distal luminal portion 222. The catheter advancement element 300 can have an inner diameter of about 0.019" such that the wall thickness in this region can be about 0.043". When the catheter advancement element 300 is assembled with the distal luminal portion 222 of the catheter and the system folded over on itself (i.e., urged into an 180 degree bend), the maximum width across the system can be less than about 0.20" or less than about 5 mm without ovalizing of either component forming the assembled system. The outer radius of curvature of the assembled system along the bend can be about 0.10".

As another example, the distal luminal portion 222 can have an outer diameter of about 0.102" and an inner diameter of about 0.089". A catheter advancement element 300 inserted through the distal luminal portion 222 can have an outer diameter of about 0.080" substantially filling the inner diameter of the distal luminal portion 222. The catheter advancement element 300 can have an inner diameter of about 0.019" such that the wall thickness in this region can be about 0.061". When the catheter advancement element 300 is assembled with the distal luminal portion 222 of the catheter and the system folded over on itself (i.e., urged into an 180 degree bend), the maximum width across the system can be less than about 0.25" or less than about 6.4 mm without ovalizing of either component forming the assembled system. The outer radius of curvature of the assembled system along the bend can be about 0.13".

The dimensions provided herein are approximate and each dimensions may have an engineering tolerance or a permissible limit of variation. Use of the term "about" or "approximately" are intended to provide such permissible tolerance to the dimension being referred to. Where "about" or "approximately" is not used with a particular dimension herein that that dimension need not be exact.

The catheter advancement element 300 can include a distal tip 346 that tapers over a length. The elongate body 360 of the catheter advancement element 300 can have an inner diameter that does not change over its length even in the presence of the tapering of the distal tip 346. Thus, the inner diameter of the lumen extending through the tubular portion of the catheter advancement element 300 can remain uniform and the wall thickness of the distal tip 346 can decrease to provide the taper. The wall thickness can thin distally along the length of the taper. Thus, the material properties in combination with wall thickness, angle, length of the taper can all contribute to the overall maximum flexibility of the distal-most end of the distal tip 346. The catheter advancement element 300 undergoes a transition in flexibility from the distal-most end towards the snug point where it achieves an outer diameter that is no more than about 0.010" different from the inner diameter of the catheter 200.

The length of the distal tip 346 (e.g. the region of the catheter advancement element 300 configured to extend distal to the distal end of the catheter 200 during use) can vary. In some implementations, the length of the distal tip 346 can be in a range of between about 0.50 cm and about 4.0 cm from the distal-most terminus of the elongate body 360. In other implementations, the length of the distal tip 346 is at least about 0.8 cm. In other implementations, the length of the distal tip 346 is between 2.0 cm to about 2.5 cm. In some implementations, the length of the distal tip 236 varies depending on the inner diameter of the elongate body 360. For example, the length of the distal tip 236 can be as short as 0.5 cm and the inner diameter of the catheter 200 can be 0.054". The distal tip 346 can be a constant taper from the outer diameter of the elongate body 360 down to a second smaller outer diameter at the distal-most tip. In some implementations, the constant taper of the distal tip 346 can be from about 0.048" outer diameter down to about 0.031" outer diameter that tapers to about 65% of the largest diameter. In some implementations, the constant taper of the distal tip 346 can be from 0.062" outer diameter to about 0.031" outer diameter that tapers to about half of the largest diameter. In still further implementations, the constant taper of the distal tip 346 can be from 0.080" outer diameter to about 0.031" outer diameter that tapers to about 40% of the largest diameter. The length of the constant taper of the distal tip 346 can vary, for example, about 0.5 cm to about 4.0 cm, or about 0.8 cm to about 3.5 cm, or about 1 cm to about 3 cm, or about 2.0 cm to about 2.5 cm. The angle of the taper can vary depending on the outer diameter of the elongate body 360. For example, the taper angle of the wall of the tapered portion of the flexible elongate body can be between 0.9 to 1.6 degree angle relative to horizontal. The taper angle of the wall of the tapered portion of the flexible elongate body can be between 2-10 degrees or 2-3 degree angle from a center line of the elongate body 360.

The distal tip 346 need not taper and can achieve its soft, atraumatic and flexible characteristic due to a material property other than due to a change in outer dimension to facilitate endovascular navigation to an embolus in tortuous anatomy. Additionally or alternatively, the distal tip 346 of the elongate body 360 can have a transition in flexibility along its length. The most flexible region of the distal tip 346 can be its distal terminus. Moving along the length of the distal tip 346 from the distal terminus towards a region proximal to the distal terminus, the flexibility can gradually approach the flexibility of the distal end of the luminal portion 222. For example, the distal tip 346 can be formed of a material having a hardness of no more than 35 D or about 62 A and transitions proximally towards increasingly harder materials having a hardness of no more than 55 D and 72 D up to the proximal portion 366, which can be a stainless steel hypotube, or a combination of a material property and tapered shape. The hypotube can be coated with one or more polymers. The hypotube of the proximal portion 366 can be fully enclosed stainless steel tube having an inner lumen or can be tubular with one or more interruptions or perforations or cuts through a sidewall (e.g., by laser cutting, micromachining and the like). The hypotube of the proximal portion 366 can define a lumen along at least a portion of its length and/or can be at least partially solid having no lumen along at least a portion of its length. In still further implementations, the proximal portion 366 can be at least partly solid and at least partly a hypotube, optionally wherein the hypotube incorporates one or more interruptions or cuts. The proximal portion 366 need not include a hypotube. The proximal portion 366 hypotube can include a material such as Nitinol in lieu of or in addition to stainless steel. In still further implementations, the catheter advancement element 300 need not include any metallic structure within its proximal portion 366 or within its elongate body 360. The catheter advancement element 300 can be formed completely of polymeric materials where the elongate body 360 is unreinforced polymeric material and the proximal portion 366 is a reinforced polymeric material. The reinforcement of the reinforced polymer can also be polymeric providing additional rigidity to the proximal portion 366 compared to the unreinforced polymer of the elongate body 360. The reinforced polymer of the proximal portion 366 can also include reinforcement structures such as a braid, coil, or other reinforcement structure or combination of structures. The reinforcement structures can be metallic or nonmetallic reinforcement.

The materials used to form the regions of the elongate body 360 can include PEBAX elastomers in the Shore D to Shore A hardness ranges (such as PEBAX 25 D, 35 D, 40 D, 45 D, 55 D, 63 D, 70 D, 72 D) with or without a lubricious additive compound, such as Mobilize (Compounding Solutions, Lewiston, Me.). In some implementations, the material used to form a region of the elongate body 360 can be an aromatic polyether-based thermoplastic polyurethane (e.g., Tecothane, Lurbizol) in a Shore A hardness range of 90 A, 85 A, 75 A, 62 A, 50 A. Incorporation of a lubricious additive directly into the polymer elongate body means incorporation of a separate lubricious liner, such as a Teflon liner, is unnecessary. Thus, the flexible elongate body 360 can be formed without a tubular inner liner. The flexible elongate body 360 can be formed without an inner liner at the inner diameter that is sized to accommodate a guidewire. This allows for a more flexible element that can navigate the distal cerebral anatomy and is less likely to kink. Similar materials can be used for forming the distal luminal portion 222 of the catheter 200 providing similar advantages. It should also be appreciated that the flexibility of the distal tip 346 can be achieved by a combination of flexible lubricious materials and tapered shapes. For example, the length of the tip 346 can be kept shorter than 2 cm-3 cm, but maintain optimum deliverability due to a change in flexible material from distal-most tip towards a more proximal region a distance away from the distal-most tip. In an implementation, the elongate body 360 is formed of PEBAX (polyether block amide) embedded silicone designed to maintain the highest degree of flexibility. The wall thickness of the distal end of the luminal portion 222 can also be made thin enough such that the lip formed by the distal end of the luminal portion 222 relative to the elongate body 360 is minimized.

The flexible elongate body 360 of the catheter advancement element 300 (sometimes referred to herein as a device 300) can include a proximal end, a distal end, and a single lumen extending therebetween. The flexible elongate body 360 can include a proximal segment or proximal portion 366 that include a hypotube coated with a polymer. The flexible elongate body 360 can also include an intermediate segment that is an unreinforced polymer having a durometer of no more than 72 D, for example, 55 D or a blend of 55 D and 35 D. The flexible elongate body 360 can include a tip segment that is also formed of a polymer, but that is different from the polymer of the intermediate segment and that has a durometer of no more than about 35 D. The tip segment can have a length of at least 5 cm, for example, 5 cm up to about 20 cm. The tip segment can include a tapered portion 346 that tapers distally from a first outer diameter to a second outer diameter over a length of about 0.5 cm to about 4 cm, or about 1 cm to about 3 cm, or about 2 cm to about 2.5 cm. The catheter advancement element 300 can have a length configured to extend from outside the patient's body at the access site, through the femoral artery and to a petrous portion of the internal carotid artery as described elsewhere herein. The inner diameter of the catheter advancement element 300 can accommodate a guidewire. The ID can be less than 0.024" or between about 0.019" to about 0.021". The intermediate segment can include a first segment having a material hardness of no more than about 55 D and a second segment located proximal to the first segment having a material hardness of no more than 72 D. The proximal region hypotube can form a single continuous lumen from the intermediate segment to a proximal-most end, such as a proximal hub. The hypotube can be an uncut hypotube or can be cut as described elsewhere herein. The hypotube can be a stainless steel hypotube. The flexible elongate body can be formed without a tubular inner liner and the unreinforced polymer of the flexible elongate body can incorporate a lubricious additive.

As mentioned above, the elongate body 360 can be constructed to have variable stiffness between the distal and proximal ends of the elongate body 360. The flexibility of the elongate body 360 is highest at the distal-most terminus of the distal tip 346 and can gradually transition in flexibility to approach the flexibility of the distal end of the luminal portion 222, which is typically less flexible than the distal-most terminus of the distal tip 346. Upon inserting the catheter advancement element 300 through the catheter 200, the region of the elongate body 360 extending beyond the distal end of the luminal portion 222 can be the most flexible and the region of the elongate body 360 configured to be aligned with the distal end of the luminal portion 222 during advancement in the vessel can have a substantially identical flexibility as the distal end of the luminal portion 222 itself. As such, the flexibility of the distal end of the luminal portion 222 and the flexibility of the body 360 just proximal to the extended portion (whether tapered or having no taper) can be substantially the same. This provides a smooth transition in material properties to improve tracking of the catheter system through tortuous anatomy. Further, the more proximal sections of the elongate body 360 can be even less flexible and increasingly stiffer. The change in flexibility of the elongate body 360 can be a function of a material difference, a dimensional change such as through tapering, or a combination of the two. The elongate body 360 has a benefit over a microcatheter in that it can have a relatively large outer diameter that is just 0.003"-0.010" smaller than the inner diameter of the distal luminal portion 222 of the catheter 200 and still maintain a high degree of flexibility for navigating tortuous anatomy. When the gap between the two components is too tight (e.g. less than about 0.003"), the force needed to slide the catheter advancement element 300 relative to the catheter 200 can result in damage to one or both of the components and increases risk to the patient during the procedure. The gap results in too tight of a fit to provide optimum relative sliding. When the gap between the two components is too loose (e.g. greater than about 0.010"), the distal end of the catheter 200 forms a lip that is prone to catch on branching vessels during advancement through tortuous neurovasculature, such as around the carotid siphon where the ophthalmic artery branches off.

The gap in ID/OD between the elongate body 360 and the distal luminal portion 222 can be in this size range (e.g. 0.003"-0.010") along a majority of their lengths. For example, the elongate body 360 can have a relatively uniform outer diameter that is between about 0.048" to about 0.080" from a proximal end region to a distal end region up to a point where the taper of the distal tip 346 begins. Similarly, the distal luminal portion 222 of the catheter 200 can have a relatively uniform inner diameter that is between about 0.054" to about 0.088" from a proximal end region to a distal end region. As such, the difference between their respective inner and outer diameters along a majority of their lengths can be within this gap size range of 0.003" to 0.010". The distal tip 346 of the elongate body 360 that is tapered will have a larger gap size relative to the inner diameter of the distal luminal portion 222. During use, however, this tapered distal tip 346 is configured to extend distal to the distal end of the catheter 200 such that the region of the elongate body 360 having an outer diameter sized to match the inner diameter of the distal luminal portion 222 is positioned within the lumen of the catheter 200 such that it can minimize the lip at the distal end of the catheter 200.

The elongate body 360 can be formed of various materials that provide a suitable flexibility and lubricity. Example materials include high density polyethylene, 72 D PEBAX, 90 D PEBAX, or equivalent stiffness and lubricity material. At least a portion of the elongate body 360 can be reinforced to improve navigation and torqueing (e.g. braided reinforcement layer). The flexibility of the elongate body 360 can increase towards the distal tip 346 such that the distal region of the elongate body 360 is softer, more flexible, and articulates and bends more easily than a more proximal region. For example, a more proximal region of the elongate body can have a bending stiffness that is flexible enough to navigate tortuous anatomy such as the carotid siphon without kinking. In some implementations, the elongate body 360 is a fully polymeric structure (except perhaps the presence of one or more radiomarkers) without any reinforcement, particularly in distal regions of the elongate body 360. The fully polymeric, unreinforced distal region of the elongate body 360 provides a particularly low bending stiffness range described elsewhere herein that results in the catheter advancement element 300 being particularly suitable for navigation through tortuous anatomy (e.g., 180 degrees around a radius as small as 2 mm without kinking). In other implementations, the elongate body 360 incorporates a reinforcement layer that can extend up to the distal tip 346 or can extend a distance short of the distal tip 346. If the elongate body 360 has a braid reinforcement layer along at least a portion of its length, the braid reinforcement layer can terminate a distance proximal to the distal tip 346. For example, the distance from the end of the braid to the distal tip can be about 10 cm to about 15 cm or from about 4 cm to about 10 cm or from about 4 cm up to about 15 cm. The reinforcement layer can be metallic or nonmetallic material. In still other implementations, the reinforcement can extend all the way to the distal tip 346. The shore hardness of the polymer segments within the distal tip 346 can be reduced to offset or compensate for the additional stiffness due to the presence of the reinforcement. This allows for the reinforced distal tip 346 to maintain a flexibility and low bending force range that is still suitable for navigation through tortuous anatomy. The reinforcement (e.g., braid, coil, or combination) can extending along the length of the catheter advancement element 300 (up to or excluding the distal tip 346). The catheter advancement element 300 can also include one or more distinct regions of reinforcement along one or more points of its length. For example, one or more distinct coils or bands of reinforcement can be incorporated that encircle the catheter advancement element 300. The band can cover only a short length of the element 300 that is as wide as the band itself as opposed to windings of a ribbon forming a plurality of coils over a greater length. The distinct bands can be located within one or more regions of the proximal portion 366 and/or within one or more regions of the elongate body 360.

Where the catheter advancement element is described herein as being fully polymeric and having no metallic structure for reinforcement or otherwise, the catheter advancement element may still incorporate one or more radiopaque markers to identify particular locations along its length. A fully polymeric catheter advancement element 300 or a fully polymeric elongate body 360 of the catheter advancement element 300 may additionally include radiopaque contrast material embedded in or coating the polymer including barium sulfate, bismuth compounds, tungsten, platinum/iridium, tantalum, platinum, and other metallic materials that absorb x-rays.

Figure 7A:
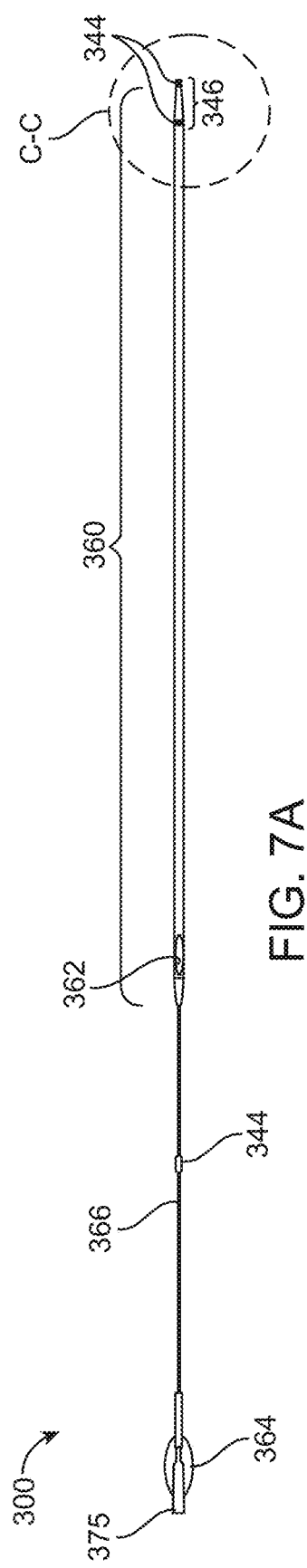
FIG. 7A is a side view of an implementation of a catheter advancement element.
Figure 7B:
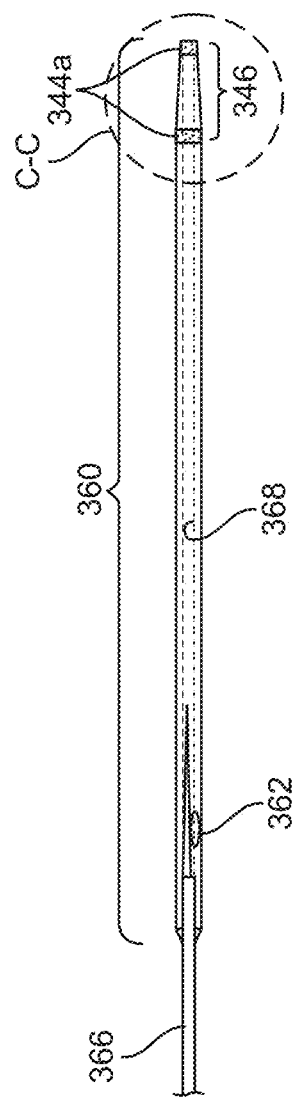
FIG. 7B is a cross-sectional view of the catheter advancement element of FIG. 7A.
Figure 7C:
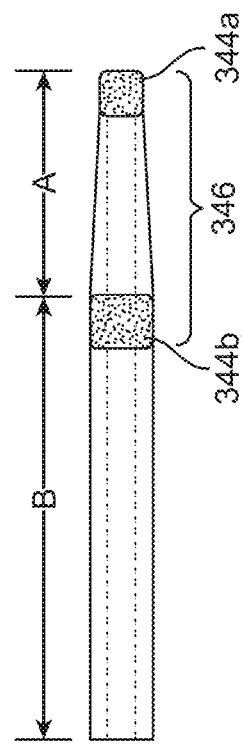
FIG. 7C is a detail view of FIG. 7B taken along circle C-C.

In some implementations, the elongate body 360 can be generally tubular along at least a portion of its length such that it has a single lumen 368 extending parallel to a longitudinal axis of the catheter advancement element 300 (see FIG. 7A-7C and also FIG. 10A-10C). In an implementation, the single lumen 368 of the elongate body 360 is sized to accommodate a guidewire, however use of the catheter advancement element 300 generally eliminates the need for a guidewire lead. The guidewire can extend through the single lumen 368 generally concentrically from a proximal opening to a distal opening through which the guidewire can extend. In some implementations, the proximal opening is at the proximal end of the catheter advancement element 300 such that the catheter advancement element 300 is configured for over-the-wire (OTW) methodologies. In other implementations, the proximal opening is a rapid exchange opening 362 through a wall of the catheter advancement element 300 such that the catheter advancement element 300 is configured for rapid exchange rather than or in addition to OTW. In this implementation, the proximal opening 362 extends through the sidewall of the elongate body and is located a distance away from a proximal tab 364 and distal to the proximal portion 366 (see FIGS. 7A-7B and 7D). The proximal opening 362 can be located a distance of about 10 cm from the distal tip 346 up to about 20 cm from the distal tip 346. In some implementations, the proximal opening 362 can be located near a region where the elongate body 360 is joined to the proximal portion 366, for example, just distal to an end of the hypotube (see FIG. 7B). In other implementations, the proximal opening 362 is located more distally such as about 10 cm to about 18 cm from the distal-most end of the elongate body 360 (see FIG. 7D). A proximal opening 362 that is located closer to the distal tip 346 allows for easier removal of the catheter advancement element 300 from the catheter 200 leaving the guidewire in place for a "rapid exchange" type of procedure. Rapid exchanges can rely on only a single person to perform the exchange. The catheter advancement element 300 can be readily substituted for another device using the same guidewire that remains in position. The single lumen 368 of the elongate body 360 can be configured to receive a guidewire having an outer diameter from about 0.010" up to about 0.024", or in the range of 0.012" and 0.022" outer diameter, or in the range of between 0.014" and 0.020" outer diameter. The single lumen 368 of the elongate body 360 can have an inner diameter at the distal tip (i.e., the size of the distal opening from the single lumen 368) that is at least about 0.010" up to about 0.030", about 0.012" up to about 0.026" inner diameter, or about 0.016" up to about 0.024" inner diameter, or about 0.020" up to about 0.022" inner diameter, or about 0.019" and about 0.021". The elongate body 360 can be about 0.002" greater, or about 0.003" greater, or about 0.004" greater in inner diameter than the outer diameter of the guidewire. In an implementation, the guidewire outer diameter is between 0.014" and about 0.022" and the inner luminal diameter of the elongate body 360 is between 0.020" and 0.024". The difference in size between the distal opening inner diameter of the elongate body 360 and the outer diameter of the guidewire can be between about 0.002" up to about 0.010".

The inner diameter of the elongate body 360 can be constant along its length even where the single lumen passes through the tapering distal tip 346. Alternatively, the inner diameter of the elongate body 360 can have a first size through the tapering distal tip 346 and a second, larger size through the cylindrical section of the elongate body 360. The cylindrical section of the elongate body 360 can have a constant wall thickness or a wall thickness that varies to a change in inner diameter of the cylindrical section. As an example, the outer diameter of the cylindrical section of the elongate body 360 can be about 0.080". The inner diameter of the elongate body 360 within the cylindrical section can be uniform along the length of the cylindrical section and can be about 0.019". The wall thickness in this section, in turn, can be about 0.061". As another example, the outer diameter of the cylindrical section of the elongate body 360 can again be between about 0.080". The inner diameter of the elongate body 360 within the cylindrical section can be non-uniform along the length of the cylindrical section and can step-up from a first inner diameter of about 0.019" to a larger second inner diameter of about 0.021". The wall thickness, in turn, can be about 0.061" at the first inner diameter region and about 0.059" at the second inner diameter region. The wall thickness of the cylindrical portion of the elongate body 360 can be between about 0.050" to about 0.065". The wall thickness of the tapered distal tip 346 near the location of the proximal marker band can be the same as the cylindrical portion (between about 0.050" and about 0.065") and become thinner towards the location of the distal marker band. As an example, the inner diameter at the distal opening from the single lumen can be about 0.020" and the outer diameter at the distal opening (i.e. the outer diameter of the distal marker band) and be about 0.030" resulting in a wall thickness of about 0.010" compared to the wall thickness of the cylindrical portion that can be up to about 0.065". Thus, the outer diameter of the distal tip 346 can taper as can the wall thickness.

A tip segment of the flexible elongate body can have a tapered portion that tapers distally from a first outer diameter to a second outer diameter. The second outer diameter can be about ½ of the first outer diameter. The second outer diameter can be about 40% of the first outer diameter. The second outer diameter can be about 65% of the first outer diameter. The first outer diameter can be about 0.062" up to about 0.080". The second outer diameter can be about 0.031".

The guidewire, the catheter advancement element 300, and the catheter 200 can all be assembled co-axially for insertion through the working lumen of the guide sheath 400.

Figure 7D:
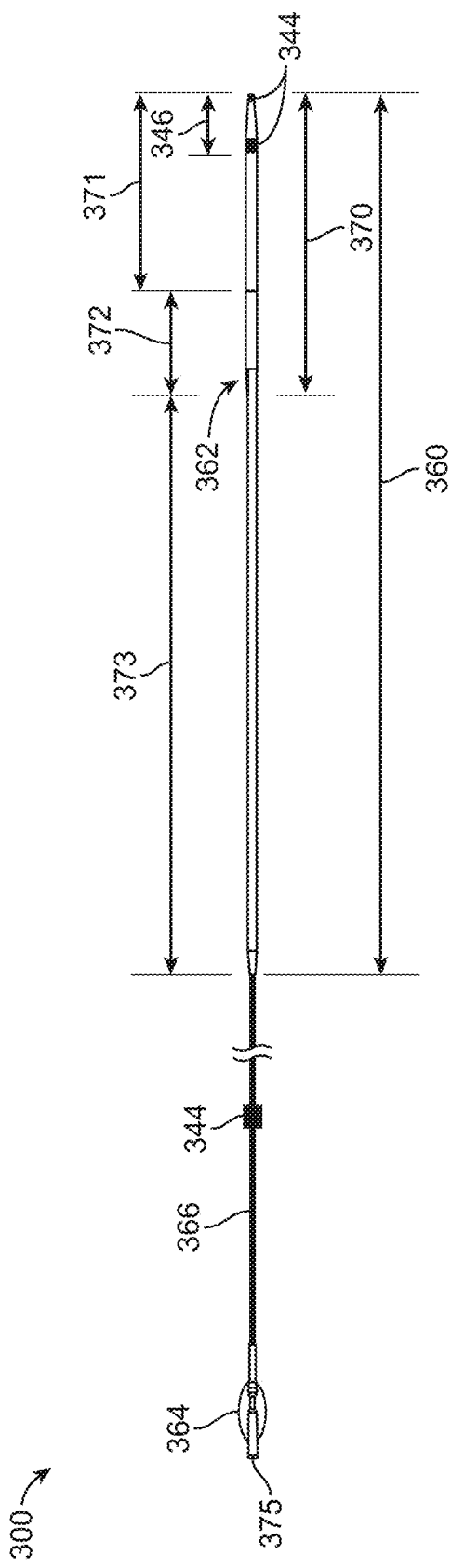
FIG. 7D is a side view of another implementation of a catheter advancement element.

FIG. 7D shows another implementation of the catheter advancement element 300 configured for rapid exchange. Rapid exchange configurations can dramatically shorten device length, decreases staffing requirements, and reduces fluoroscopy. As with other implementations described herein, the catheter advancement element 300 can include a non-expandable, flexible elongate body 360 coupled to a proximal portion 366 coupled to a proximal tab 364 or hub 375. As described elsewhere herein, the region near the distal tip 346 can be tapered such that the outer diameter tapers over a length of about 1 cm to about 3 cm. In some implementations, the distal taper length is 2.5 cm. In some implementations, the distal tip 346 tapers from about 0.080" to about 0.031". Also as described elsewhere herein, the distal tip 346 can be formed of a material having a hardness (e.g. 62 A and 35 D) that transitions proximally towards increasingly harder materials having (e.g. 55 D and 72 D) up to the proximal portion 366. For example, FIG. 7D illustrates segment 371 of the elongate body 360 including the distal tip 346 can have a hardness of 35 D and a length of about 10 cm to about 12.5 cm. Segment 371 of the elongate body 360 including the distal tip 346 can have a hardness of 62 A and a length of about 10 cm to about 12.5 cm. Segment 372 of the elongate body 360 can have a hardness of 55 D and have a length of about 5 cm to about 8 cm. Segment 373 of the elongate body 360 can have a hardness of 72 D can be about 25 cm to about 35 cm in length. Together segments 371 and 372 can form a tip segment that includes the tapered tip and segment 373 can form an intermediate segment. The three segments 371, 372, 373 combined can form an insert length of the elongate body 360 from where the proximal portion 366 couples to the elongate body 360 to the terminus of the distal tip 346 that can be about 49 cm in length. A location of a material transition between the unreinforced polymer of an intermediate segment of the flexible elongate body 360 and the hypotube of the proximal segment can be at least about 49 cm from the distal end of the flexible elongate body, ab least about 59 cm, at least about 69 cm, up to about 80 cm. The location of the material transition allows for positioning the material transition proximal to the brachiocephalic take-off in the aortic arch when the distal end of the flexible elongate body is positioned within the petrous portion of the internal carotid artery.

FIGS. 10A-10C illustrate an implementation of a catheter advancement element 300 incorporating a reinforcement layer 380. As mentioned above, the reinforcement layer 380 can be a braid or other type of reinforcement to improve the torqueability of the catheter advancement element 300 and help to bridge the components of the catheter advancement element 300 having such differences in flexibility. The reinforcement layer 380 can bridge the transition from the rigid, proximal portion 366 to the flexible elongate body 360. In some implementations, the reinforcement layer 380 can be a braid positioned between inner and outer layers of Pebax 382, 384 (see FIG. 10C). The reinforcement layer 380 can terminate a distance proximal to the distal tip region 346. For example, FIG. 10A illustrates the elongate body 360 having segment 371 and segment 373 located proximal to segment 371. Segment 371 can include the distal tip 346 having a hardness of at most about 35 D. Segment 371 is unreinforced polymer having a length of about 4 cm up to about 12.5 cm. Segment 373 of the elongate body 360 located proximal to segment 371 can include the reinforcement layer 380 and can extend a total of about 37 cm up to the unreinforced distal segment 371. A proximal end region of the reinforcement layer 380 can overlap with a distal end region of the proximal portion 366 such that a small overlap of hypotube and reinforcement exists near the transition between the proximal portion 366 and the elongate body 360.

Again with respect to FIG. 7D, an entry port 362 for a procedural guidewire 805 can be positioned a distance away from the distal-most end of the elongate body 360. In some implementations, the entry/exit port 362 can be about 18 cm from the distal-most end creating a rapid exchange wire entry/exit segment 370. The outer diameter of the elongate body 360 within segment 370 (segments 371 and 372) can be about 0.080"-0.082" whereas segment 373 proximal to this rapid exchange wire entry/exit segment 370 can have a step-down in outer diameter such as about 0.062"-0.064".

Figure 7E:
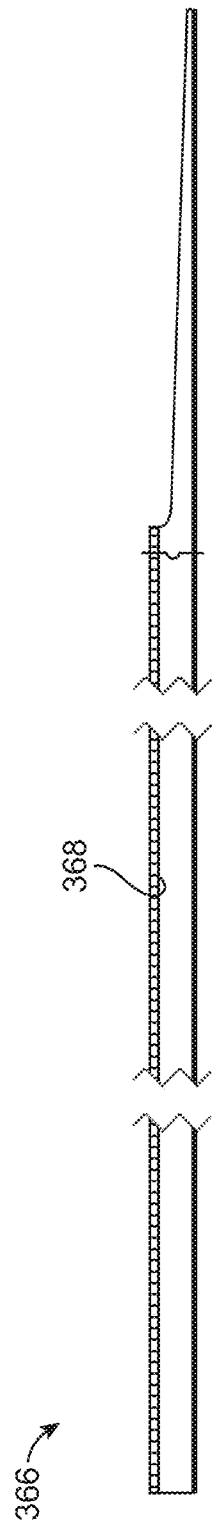
FIG. 7E is cross-sectional view of an implementation of a proximal portion the catheter advancement element of FIG. 7D.

In other implementations, the entire catheter advancement element 300 can be a tubular element configured to receive a guidewire through both the proximal portion 366 as well as the elongate body 360. For example, the proximal portion 366 can be a hypotube or tubular element having a lumen that communicates with the lumen 368 extending through the elongate body 360 (shown in FIG. 3). In some implementations, the proximal portion 366 can be a skived hypotube of stainless steel coated with PTFE having an outer diameter of 0.026". In other implementations, the outer diameter can be between 0.024" and 0.030". In some implementations, such as an over-the-wire version, the proximal portion 366 can be a skived hypotube coupled to a proximal hub 375. The proximal portion 366 can extend eccentric or concentric to the distal luminal portion 222. As best shown in FIG. 7E, the proximal portion 366 can be a stainless steel hypotube as described elsewhere herein that is bare metal or at least partially coated with a polymer or polymers. The hypotube can be a fully enclosed stainless steel tube defining an inner lumen or can be a tubular element with one or more interruptions, perforations, and or cuts through its side wall as discussed above. The proximal portion 366 can have a lumen along at least a portion of its length and can be at least partly solid along its length. The proximal portion 366 need not be or include a hypotube. The proximal portion 366 can be a solid metal wire that is round or oval cross-sectional shape. The proximal portion 366 can be a flattened ribbon of wire having a rectangular cross-sectional shape as described elsewhere herein. The ribbon of wire can be curved into a circular, oval, c-shape, or quarter circle, or other cross-sectional shape along an arc. The proximal portion 366 can have any of variety of cross-sectional shapes whether or not a lumen extends therethrough, including a circular, oval, C-shaped, D-shape, or other shape. In some implementations, the proximal portion 366 is a hypotube having a D-shape such that an inner-facing side is flat and an outer-facing side is rounded. The rounded side of the proximal portion 366 can be shaped to engage with a correspondingly rounded inner surface of the sheath 400. The hypotube can have a lubricious coating such as PTFE. The hypotube can have an inner diameter of about 0.021", an outer diameter of about 0.0275", and an overall length of about 94 cm providing a working length for the catheter advancement element 300 that is about 143 cm. Including the proximal hub 375, the catheter advancement element 300 can have an overall length of about 149 cm. In some implementations, the hypotube can be a tapered part with a length of about 100 mm, starting proximal with a thickness of 0.3 mm and ending with a thickness of 0.10 mm to 0.15 mm. In still further implementations, the elongate body 360 can be a solid element coupled to the proximal portion 366 having no guidewire lumen.

As best shown in FIGS. 7F-7J, the proximal end of the hypotube can be coupled to a proximal hub 375. The proximal hub 375 can be an over-molded component having a luer thread 377 and a luer taper 378 formed on an inside of the proximal hub 375. The proximal hub 375 can incorporate a tab 364 providing for easier gripping by a user. The proximal hub 375 prevents advancement of the catheter advancement element 300 and the catheter 200 beyond the distal tip of the base sheath 400 or guide catheter by limiting insertion into the proximal RHV 434 providing critical functional and safety features for proper operation of the system 10.

At least a portion of the solid elongate body 360, such as the elongate distal tip 346, can be formed of or embedded with or attached to a malleable material that skives down to a smaller dimension at a distal end. The distal tip 346 can be shaped to a desired angle or shape similar to how a guidewire may be used. The malleable length of the elongate body 360 can be at least about 1 cm, 3 cm, 5 cm, and up to about 10 cm, 15 cm, or longer. In some implementations, the malleable length can be about 1%, 2%, 5%, 10%, 20%, 25%, 50% or more of the total length of the elongate body 360. In some implementations, the catheter advancement element 300 can have a working length of about 140 cm to about 143 cm and the elongate body 360 can have an insert length of about 49 cm. The insert length can be the PEBAX portion of the elongate body 360 that is about 49.5 cm. As such, the malleable length of the elongate body 360 can be between about 0.5 cm to about 25 cm or more. The shape change can be a function of a user manually shaping the malleable length prior to insertion or the tip can be pre-shaped at the time of manufacturing into a particular angle or curve. Alternatively, the shape change can be a reversible and actuatable shape change such that the tip forms the shape upon activation by a user such that the tip can be used in a straight format until a shape change is desired by the user. The catheter advancement element 300 can also include a forming mandrel extending through the lumen of the elongate body 360 such that a physician at the time of use can mold the distal tip 346 into a desired shape. As such, the moldable distal tip 346 can be incorporated onto an elongate body 360 that has a guidewire lumen.

The elongate body 360 can extend along the entire length of the catheter 200, including the distal luminal portion 222 and the proximal extension 230 or the elongate body 360 can incorporate the proximal portion 366 that aligns generally side-by-side with the proximal extension 230 of the catheter 200, as described above. The proximal portion 366 of the elongate body 360 can be positioned co-axial with or eccentric to the elongate body 360. The proximal portion 366 of the elongate body 360 can have a lumen extending through it. Alternatively, the portion 366 can be a solid rod or ribbon having no lumen.

Again with respect to FIGS. 7A-7D, like the distal luminal portion 222 of the catheter 200, the elongate body 360 can have one or more radiopaque markers 344 along its length. The one or more markers 344 can vary in size, shape, and location. One or more markers 344 can be incorporated along one or more parts of the catheter advancement element 300, such as a tip-to-tip marker, a tip-to-taper marker, an RHV proximity marker, a Fluoro-saver marker, or other markers providing various information regarding the relative position of the catheter advancement element 300 and its components. In some implementations and as best shown in FIG. 7C, a distal end region can have a first radiopaque marker 344*a* and a second radiopaque marker 344*b* can be located to indicate the border between the tapering of the distal tip 346 and the more proximal region of the elongate body 360 having a uniform or maximum outer diameter. This provides a user with information regarding an optimal extension of the distal tip 346 relative to the distal end of the luminal portion 222 to minimize the lip at this distal end of the luminal portion 222 for advancement through tortuous anatomy. In other implementations, for example where the distal tip 346 is not necessarily tapered, but instead has a change in overall flexibility along its length, the second radiopaque marker 344*b* can be located to indicate the region where the relative flexibilities of the elongate body 360 (or the distal tip 346 of the elongate body 360) and the distal end of the luminal portion 222 are substantially the same. The marker material may be a barium sulfate, bismuth, platinum/iridium band, a tungsten, platinum, or tantalum-impregnated polymer, or other radiopaque marker that does not impact the flexibility of the distal tip 346 and elongate body 360. In some implementations, the radiopaque markers are extruded PEBAX loaded with tungsten for radiopacity. In some implementations, the proximal marker band can be about 2.0 mm wide and the distal marker band can be about 2.5 mm wide to provide discernable information about the distal tip 346. Some marker materials may impact the flexibility of the polymer within which they are embedded. For example, barium sulfate tends to stiffen polymer. Thus, the polymer where the marker material is incorporated may have a reduced hardness to achieve a final material property for the region that remains suitable for navigation. The distal tip 346 may incorporate a proximal end radiopaque marker that is a band of barium sulfate-loaded PEBAX that has a final durometer of no greater than 35 D, or 25 D, or another soft durometer. The PEBAX prior to the embedding of the radiopaque material may have an initial durometer that is less than the final durometer. The reduction in polymer hardness can offset the stiffening effects of the marker material so that the device maintains flexibility suitable for navigating tortuous anatomy (e.g., tip flexibility measurement that is less than about 0.05 Newtons and/or a catheter system capable of bending 180 degrees while maintaining a maximum folded width across that is less than about 5.0 mm without kinking or ovalizing).

As mentioned above, the proximal extension 230 of the catheter 200 can include a proximal tab 234 on the proximal end of the proximal extension 230. Similarly, the proximal portion 366 coupled to the elongate body 360 can include a tab 364. The tabs 234, 364 can be configured to removably and adjustable connect to one another and/or connect to their corresponding proximal portions. The coupling allows the catheter advancement element 300 to reversibly couple with the catheter 200 to lock (and unlock) the relative extension of the distal luminal portion 222 and the elongate body 360. This allows the catheter 200 and the catheter advancement element 300 to be advanced as a single unit. In the locked configuration, the tab 364 or proximal portion 366 can be engaged with the catheter tab 234. In the unlocked configuration, the tab 364 may be disengaged from the catheter tab 234. The tab 364 or proximal portion 366 may attach, e.g., click or lock into, the catheter tab 234 in a fashion as to maintain the relationships of corresponding section of the elongate body 360 and the catheter 200 in the locked configuration. The tab 364 can be a feature on the proximal hub 375 such as the hub 375 shown in FIGS. 7F-7J.

Such locking may be achieved by, e.g., using a detent on the tab 364 that snaps into place within a recess formed in the catheter tab 234, or vice versa. For example, the tab 234 of the catheter 200 can form a ring having a central opening extending therethrough. The tab 364 of the body 360 can have an annular detent with a central post sized to insert through the central opening of the tab 234 such that such that the ring of the tab 234 is received within the annular detent of tab 364 forming a singular grasping element for a user to advance and/or withdraw the catheter system through the access sheath. The tabs 234, 364 may be affixed or may be slideable to accommodate different relative positions between the elongate body 360 and the luminal portion 222 of the catheter 200. In some implementations, a proximal end of the proximal extension 230 of the catheter 200 can include a coupling feature 334, such as clip, clamp, c-shaped element or other connector configured to receive the proximal portion 366 of the catheter advancement element 300 (see FIG. 2A). The coupling feature 334 can be configured to snap together with the proximal portion 366 through an interference fit such that a first level of force is needed in order to insert the proximal portion 366 into the clip of the tab 234 and a second, greater level of force is needed to remove the proximal portion 366 from the clip of the tab 234. However, upon inserting the proximal portion 366 into the coupling feature 334 the catheter advancement element 300 and the catheter 200 can still be slideably adjusted relative to one another along a longitudinal axis of the system. The amount of force needed to slideably adjust the relative position of the two components can be such that inadvertent adjustment is avoided and the relative position can be maintained during use, but can be adjusted upon conscious modification. The configuration of the coupling between the proximal portion 366 of the catheter advancement element 300 and the proximal extension 360 of the catheter 200 can vary. Generally, however, the coupling is configured to be reversible and adjustable while still providing adequate holding power between the two elements in a manner that is relatively user-friendly (e.g. allows for one-handed use) and organizes the proximal ends of the components (e.g. prevents the proximal extension 360 and proximal portion 366 from becoming twisted and entangled with one another). It should also be appreciated that the coupling feature 334 configured to prevent entanglement and aid in the organization of the proximal portions can be integrated with the tabs or can be a separate feature located along their proximal end region.

The catheter advancement element 300 can be placed in a locked configuration with the catheter 200 configured for improved tracking through a tortuous and often diseased vasculature in acute ischemic stroke. Other configurations are considered herein. For example, the elongate body 360 can include one or more detents on an outer surface. The detents can be located near a proximal end region and/or a distal end region of the elongate body 360. The detents are configured to lock with correspondingly-shaped surface features on the inner surface of the luminal portion 222 through which the elongate body 360 extends. The catheter advancement element 300 and the catheter 200 can have incorporate more than a single point of locking connection between them. For example, a coupling feature 334, such as clip, clamp, c-shaped element or other connector configured to hold together the catheter advancement element 300 and proximal extension 230 or tab 234 of the catheter 200 as described elsewhere herein.

In some implementations, the proximal extension 230 of the catheter 200 can run alongside or within a specialized channel of the proximal portion 366. The channel can be located along a length of the proximal portion 366 and have a cross-sectional shape that matches a cross-sectional shape of the catheter proximal extension 230 such that the proximal extension 230 of the catheter 200 can be received within the channel and slide smoothly along the channel bi-directionally. Once the catheter 200 and elongate body 360 are fixed, the combined system, i.e., the catheter 200-catheter advancement element 300 may be delivered to a target site, for example through the working lumen of the guide sheath 400 described elsewhere herein.

The catheter advancement element 300 (whether incorporating the reinforcement layer or not) loaded within the lumen of the catheter 200 may be used to advance a catheter 200 to distal regions of the brain (e.g. level of the MCA). The traditional approach to the Circle of Willis is to use a triaxial system including a guidewire placed within a conventional microcatheter placed within an intermediate catheter. The entire coaxial system can extend through a base catheter or sheath. The sheath is typically positioned such that the distal tip of the sheath is placed in a high cervical carotid artery. The coaxial systems are often advanced in unison up to about the terminal carotid artery where the conventional coaxial systems must then be advanced in a step-wise fashion in separate throws. This is due to the two sequential 180 degree or greater turns (see FIGS. 1A-1C). The first turn is at the level of the petrous to the cavernous internal carotid artery. The second turn is at the terminal cavernous carotid artery as it passes through the bony elements and reaches the bifurcation into the anterior cerebral artery ACA and middle cerebral artery MCA. This S-shape region is referred to herein as the "siphon" or "carotid siphon". The ophthalmic artery arises from the cerebral ICA, which represents a common point of catheter hang up in accessing the anterior circulation.

Conventional microcatheter systems can be advanced through to the anterior circulation over a guidewire. Because the inner diameter of the conventional microcatheter is significantly larger than the outer diameter of the guidewire over which it is advanced, a lip can be formed on a distal end region of the system that can catch on these side branches during passage through the siphon. Thus, conventional microcatheter systems (i.e. guidewire, microcatheter, and intermediate catheter) are never advanced through both bends of the carotid siphon simultaneously in a single smooth pass to distal target sites. Rather, the bends of the carotid siphon are taken one at a time in a step-wise advancement technique. For example, to pass through the carotid siphon, the conventional microcatheter is held fixed while the guidewire is advanced alone a first distance (i.e. through the first turn of the siphon). Then, the guidewire is held fixed while the conventional microcatheter is advanced alone through the first turn over the guidewire. Then, the conventional microcatheter and guidewire are held fixed while the intermediate catheter is advanced alone through the first turn over the microcatheter and guidewire. The process repeats in order to pass through the second turn of the siphon, which generally is considered the more challenging turn into the cerebral vessel. The microcatheter and intermediate catheter are held fixed while the guidewire is advanced alone a second distance (i.e. through the second turn of the siphon). Then, the guidewire and interventional catheter are held fixed while the microcatheter is advanced alone through that second turn over the guidewire. Then, the guidewire and the microcatheter are held fixed while the interventional catheter is advanced alone through the second turn. This multi-stage, step-wise procedure is a time-consuming process that requires multiple people performing multiple hand changes on the components. For example, two hands to fix and push the components over each other forcing the user to stage the steps as described above. The step-wise procedure is required because the stepped transitions between these components (e.g. the guidewire, microcatheter, and intermediate catheter) makes advancement too challenging.

In contrast, the catheter 200 and catheter advancement element 300 eliminate this multi-stage, step-wise component advancement procedure to access distal sites across the siphon. The catheter 200 and catheter advancement element 300 can be advanced as a single unit through the both turns of the carotid siphon CS. Both turns can be traversed in a single smooth pass or throw to a target in a cerebral vessel without the step-wise adjustment of their relative extensions and without relying on the conventional step-wise advancement technique, as described above with conventional microcatheters. The catheter 200 having the catheter advancement element 300 extending through it allows a user to advance them in unison in the same relative position from the first bend of the siphon through the second bend beyond the terminal cavernous carotid artery into the ACA and MCA. Importantly, the advancement of the two components can be performed in a single smooth movement through both bends without any change of hand position.

The catheter advancement element 300 can be in a juxtapositioned relative to the catheter 200 that provides an optimum relative extension between the two components for single smooth advancement. The catheter advancement element 300 can be positioned through the lumen of the catheter 200 such that its distal tip 346 extends beyond a distal end of the catheter 200. The distal tip 346 of the catheter advancement element 300 eliminates the stepped transition between the inner member and the outer catheter 200 thereby avoiding issues with catching on branching vessels within the region of the vasculature such that the catheter 200 may easily traverse the multiple angulated turns of the carotid siphon CS. The optimum relative extension, for example, can be the distal tip 346 of the elongate body 360 extending distal to a distal end of the catheter 200 as described elsewhere herein. A length of the distal tip 346 extending distal to the distal end can be between 0.5 cm and about 3 cm. This juxtaposition can be a locked engagement with a mechanical element or simply by a user holding the two components together.

The components can be advanced together with a guidewire, over a guidewire pre-positioned, or without any guidewire at all. In some implementations, the guidewire can be pre-assembled with the catheter advancement element 300 and catheter 200 such that the guidewire extends through a lumen of the catheter advancement element 300, which is loaded through a lumen of the catheter 200, all prior to insertion into the patient. The pre-assembled components can be simultaneously inserted into the sheath 400 and advanced together up through and past the turns of the carotid siphon. The guidewire can be positioned within a portion of the lumen of the catheter advancement element 300, but not extend distal to the distal opening from the lumen so that the distal-most end of the guidewire remains housed within the catheter advancement element 300 for optional use in a step of the procedure. For example, the catheter advancement element 300 having a guidewire parked within its lumen proximal to the distal opening can be used to deliver the catheter 200 to a target location or near a target location. The guidewire can be advanced distally while the catheter advancement element 300 and catheter 200 remain in a fixed position until a distal end of the guidewire is advanced beyond the distal opening a distance. The catheter advancement element 300 with or without the catheter 200 can then be advanced over the guidewire that distance. The guidewire can then be withdrawn inside the lumen of the catheter advancement element 300.

Figure 11:
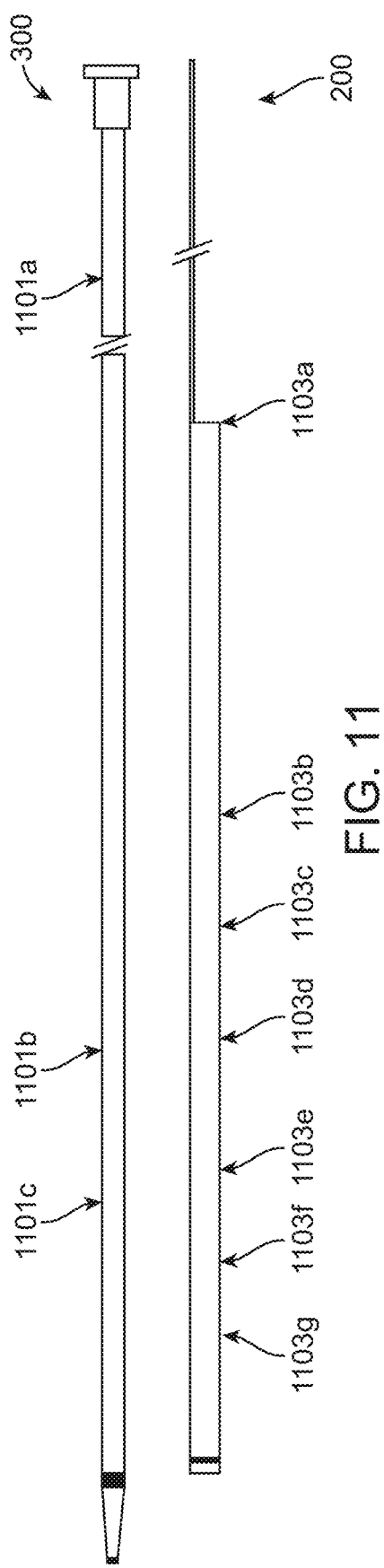
FIG. 11 is a schematic of an implementation of a catheter aligned with an implementation of a catheter advancement element illustrating staggered material transitions.

The optimum relative extension of the catheter 200 and catheter advancement element 300 can be based additionally on the staggering of material transitions. FIG. 11 is a schematic illustrating approximate locations of the material transitions in the catheter advancement element 300 and the approximate locations of the material transitions in the catheter 200. For example, the catheter advancement element 300 can include a proximal portion 366, which can be a hypotube that is bare stainless steel or coated with one or more polymers. The proximal portion 366 transitions at a location 1101a to a region having a material hardness of about 55 D that transitions at a location 1101b to a region having a material hardness of about 35 D that transitions at a location 1101c to a region have a material hardness of 35 D. Similarly, the catheter 200 can include a proximal extension 230 that is a stainless steel ribbon. The proximal extension 230 transitions at a location 1103a to a region having a hardness of 72 D that transitions at a location 1103b to a region having a hardness of 55 D that transitions at a location 1103c to a region having a material hardness of about 40 D that transitions at a location 1103d to a region having a material hardness of about 35 D that transitions at a location 1103e to a region have a material hardness of 25 D that transitions at a location 1103f to a region having a material hardness of about 85 A that transitions at a location 1103g to a region having a material hardness of about 80 A. A distal-most region of the catheter advancement element 300 can be formed of Tecothane having a material hardness of about 62 A. The locations 1101 of the catheter advancement element 300 and the locations 1103 of the catheter 200 can be staggered such that the locations are off-set from one another. More or fewer material transitions may exist within the catheter advancement element and catheter.

The catheter 200 and catheter advancement element 300 can be pre-assembled at the time of manufacturing such that an optimum length of the catheter advancement element 300 extends distal to the distal end of catheter 200 and/or the material transitions are staggered. An optimum length of extension can be such that the entire length of the tapered distal tip of the catheter advancement element 300 extends outside the distal end of the catheter 200 such that the uniform outer diameter of the catheter advancement element 300 aligns substantially with the distal end of the catheter 200. This can result in the greatest outer diameter of the elongate body 360 aligned substantially with the distal end of the catheter 200 such that it remains inside the lumen of the catheter 200 and only the tapered region of the distal tip 346 extends distal to the lumen of the catheter 200. This relative arrangement provide the best arrangement for advancement through tortuous vessels where a lip at the distal end of the system would pose the greatest difficulty. This optimal pre-assembled arrangement can be maintained by a coupler configured to engage with both the proximal extension 230 of the catheter 200 and the proximal portion 366 of the catheter advancement element 300. The coupler can be used during a procedure as described elsewhere herein. Alternatively, the coupler can be removed prior to a procedure.

Figure 12:
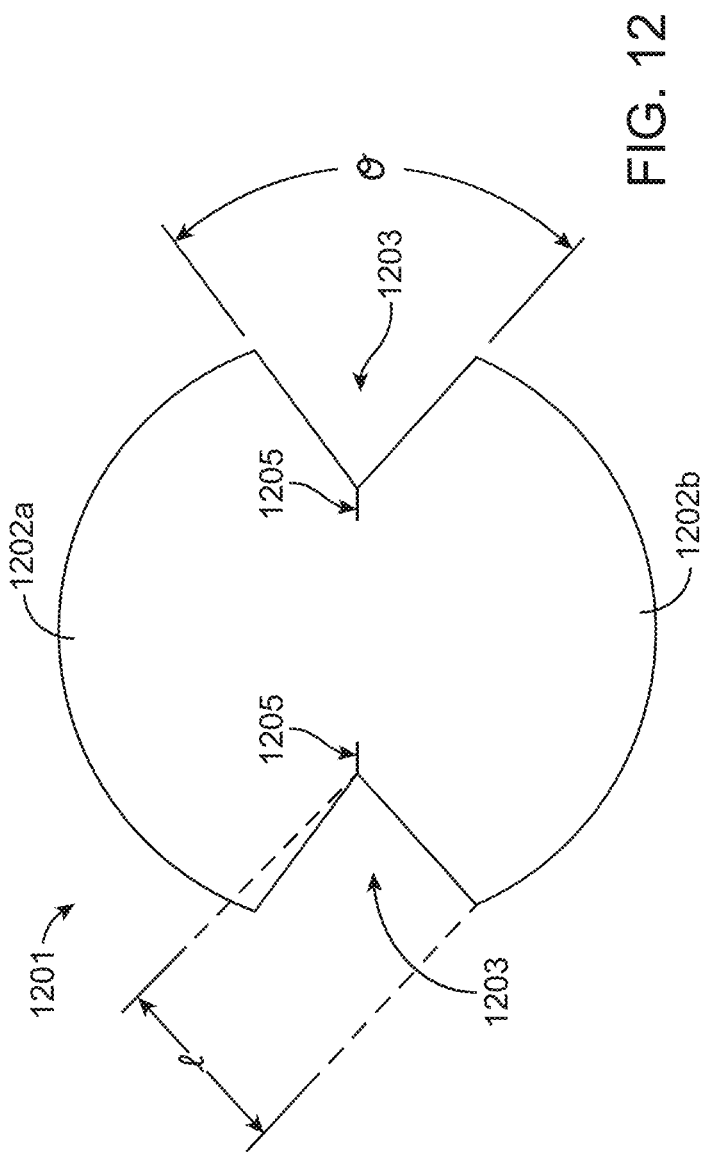
FIG. 12 is a tear-away disc coupler.

FIG. 12 illustrates an implementation of a coupler 1201 configured to be removed prior to a procedure. The coupler 1201 can be a temporary coupler configured to engage the catheter 200 and catheter advancement element 300 only at the time of manufacturing and/or during storage. In some implementations, the coupler 1201 can be a disc having a layer of adhesive material on one side. The coupler 1201 is configured to capture both the proximal extension 230 of the catheter 200 and the proximal portion 366 of the catheter advancement element 300 and maintain the optimal pre-assembled extension arrangement. The coupler 1201 can be torn away from the proximal extension 230 and the proximal portion 366 with ease and without leaving any residue. The coupler 1201 can a disc of plastic material, such as polyimide. The hemispheres of the disk are designed to fold over onto themselves until the adhesive side of each hemisphere engages one another thereby trapping the hypotubes of the proximal extension 230 and proximal portion 366 of the catheter 200 and catheter advancement element 300, respectively, therebetween along an equator of the disc. The disc can include a pair of notches 1203 near the equator such that the overall shape of the disc is bi-lobed. The disc can include a first rounded lobe 1202a on one side of the pair of notches 1203 and a second rounded lobe 1202b on the opposite side of the pair of notches 1203, each of the first and second lobe 1202a, 1202b having matching shapes. The hypotubes can be captured along the equator of the disc between the first and second lobes 1202a, 1202b folding over onto each other such that their adhesive sides can capture the hypotubes. The apex of each notch 1203 aligns with the equator of the disc and each can include a cut or notch extension 1205 extending toward the center of the disc. The apex of each notch 1203 in coordination with the notch extensions 1205 aid in getting the tear started creating a stress concentration tear-away location when the catheter system is ready to be used. The notch extensions 1205 help to direct the tear direction. The coupler 1201 is thereby engaged with both the hypotube proximal extension 230 of the catheter 200 and the hypotube proximal body 330 of the catheter advancement element 300, which is inserted through the lumen of the catheter 200. The coupled engagement allows the two components engaged with one another to be easily inserted into the packaging hoop while maintaining the optimal relative extension of the components. The coupler 1201 avoids catching on the packaging hoop due to the rounded, smooth surfaces and lack of edges to catch. Prior to use of the catheter system 100, a user can remove the catheter 200/catheter advancement element 300 from the packaging hoop. The coupler 1201 can be torn away from the hypotubes by a user pulling on the folded over lobes 1202a, 1202b adhered to one another. The entire coupler 1201 is thereby removed from the hypotubes without leaving any residue on the hypotubes. The system is immediately ready for insertion at an optimal pre-assembled relative extension.

The dimensions of the coupler 1201 are such that they provide ample engagement with the hypotubes thereby locking them together and maintaining the relative extension yet not so large as to negatively impact storage within the packaging hoop. The disc of the coupler 1201 can have a diameter that is about 0.75" to about 1". The disc can be relatively thin such as between about 0.0005" to about 0.0015" thick polyimide. In some implementations, the polyimide disc is about 0.001" thick. One side of the discs can include a layer of adhesive, such as silicone adhesive. The adhesive can be about 0.0015" thick. Each side of the notches 1203 can have a length 1 extending between the outer perimeter of the disc and the apex of the notch 1203. The length can be about 0.200" long. The sides can form an angle θ relative to one another that is between about 50 and 70 degrees, preferably about 60 degrees.

The catheter and the catheter advancement element may be releaseably, pre-packaged in a locked position according to any of a variety of methods (e.g. shrink-wrap, and other known methods).

Materials

One or more components of the catheters described herein may include or be made from a variety of materials including one or more of a metal, metal alloy, polymer, a metal-polymer composite, ceramics, hydrophilic polymers, polyacrylamide, polyethers, polyamides, polyethylenes, polyurethanes, copolymers thereof, polyvinyl chloride (PVC), PEO, PEO-impregnated polyurethanes such as Hydrothane, Tecophilic polyurethane, Tecothane, PEO soft segmented polyurethane blended with Tecoflex, thermoplastic starch, PVP, and combinations thereof, and the like, or other suitable materials.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material and as described elsewhere herein.

Inner liner materials of the catheters described herein can include low friction polymers such as PTFE (polytetrafluoroethylene) or FEP (fluorinated ethylene propylene), PTFE with polyurethane layer (Tecoflex). Reinforcement layer materials of the catheters described herein can be incorporated to provide mechanical integrity for applying torque and/or to prevent flattening or kinking such as metals including stainless steel, Nitinol, Nitinol braid, helical ribbon, helical wire, cut stainless steel, or the like, or stiff polymers such as PEEK. Reinforcement fiber materials of the catheters described herein can include various high tenacity polymers like Kevlar, polyester, meta-para-aramide, PEEK, single fiber, multi-fiber bundles, high tensile strength polymers, metals, or alloys, and the like. Outer jacket materials of the catheters described herein can provide mechanical integrity and can be contracted of a variety of materials such as polyethylene, polyurethane, PEBAX, nylon, Tecothane, and the like. Other coating materials of the catheters described herein include paralene, Teflon, silicone, polyimide-polytetrafluoroetheylene, and the like.

Implementations describe catheters and delivery systems and methods to deliver catheters to target anatomies. However, while some implementations are described with specific regard to delivering catheters to a target vessel of a neurovascular anatomy such as a cerebral vessel, the implementations are not so limited and certain implementations may also be applicable to other uses. For example, the catheters can be adapted for delivery to different neuroanatomies, such as subclavian, vertebral, carotid vessels as well as to the coronary anatomy or peripheral vascular anatomy, to name only a few possible applications. It should also be appreciated that although the systems described herein are described as being useful for treating a particular condition or pathology, that the condition or pathology being treated may vary and are not intended to be limiting. Use of the terms "embolus," "embolic," "emboli," "thrombus," "occlusion," etc. that relate to a target for treatment using the devices described herein are not intended to be limiting. The terms may be used interchangeably and can include, but are not limited to a blood clot, air bubble, small fatty deposit, or other object carried within the bloodstream to a distant site or formed at a location in a vessel. The terms may be used interchangeably herein to refer to something that can cause a partial or full occlusion of blood flow through or within the vessel.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation," "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of the catheters and/or delivery systems to a specific configuration described in the various implementations.

The word "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. An intravascular catheter advancement device for advancing a catheter within the neurovasculature, the catheter advancement device comprising:
   a flexible elongate body having a proximal end, a distal end, and a single lumen extending therebetween, the flexible elongate body comprising:
      a proximal segment, wherein the proximal segment comprises a hypotube coated with a polymer;
      an intermediate segment comprising an unreinforced polymer having a durometer of no more than 72 D; and
      a tip segment, wherein the tip segment is formed of a polymer different from the intermediate segment and has a durometer of no more than about 35 D and a length of at least 5 cm, wherein the tip segment has a tapered portion that tapers distally from a first outer diameter to a second outer diameter over a length of between 1 and 3 cm,
   wherein the catheter advancement device has a length configured to extend from outside a patient's body, through a femoral artery, and to a petrous portion of an internal carotid artery and an inner diameter less than 0.024 inches to accommodate a guidewire.

2. The device of claim 1, wherein flexible elongate body is formed without a tubular inner liner.

3. The device of claim 2, wherein the unreinforced polymer of the flexible elongate body incorporates a lubricious additive.

4. The device of claim 1, wherein a taper angle of the wall of the tapered portion relative to a center line of the tapered portion is between 0.9 to 1.6 degrees or 2 to 3 degrees.

5. The device of claim 1, wherein the second outer diameter is about ½ of the first outer diameter.

6. The device of claim 1, wherein the second outer diameter is about 40% of the first outer diameter.

7. The device of claim 1, wherein the second outer diameter is about 65% of the first outer diameter.

8. The device of claim 1, wherein the intermediate segment includes a first segment having a material hardness of no more than 55 D and a second segment located proximal to the first segment having a material hardness of no more than 72 D.

9. A system including the device of claim 1, further comprising a catheter having a lumen and a distal end, wherein an outer diameter of the flexible elongate body is sized to be positioned coaxially within the catheter lumen such that the tapered portion of the tip segment extends distally beyond the distal end of the catheter to aid in delivery of the catheter to an intracranial vessel.

10. The device of claim 1, wherein the flexible elongate body has an insert length that is at least about 49 cm.

11. The device of claim 10, wherein the location allows for positioning the material transition proximal to the brachiocephalic take-off in the aortic arch when the distal end is positioned within the petrous portion of the internal carotid artery.

12. The device of claim 1, wherein a location of a material transition between the unreinforced polymer and the hypotube is at least about 49 cm from the distal end of the flexible elongate body.

13. The device of claim 1, wherein the hypotube has an inner diameter of about 0.021" and an outer diameter of about 0.027".

14. The device of claim 1, wherein the first outer diameter is about 0.062" up to about 0.080".

15. The device of claim 14, wherein the second outer diameter is about 0.031".

16. The device of claim 1, wherein the tip segment comprises a first radiopaque marker and a second radiopaque marker.

17. The device of claim 16, wherein the first radiopaque marker is positioned on the first outer diameter and identifies a border between the first outer diameter and the tapered portion.

18. The device of claim 17, wherein the second radiopaque marker is positioned on the second outer diameter.

19. The device of claim 16, wherein the first and second radiopaque markers have different widths.

20. The device of claim 16, wherein the first and second radiopaque markers are extruded polymer loaded with a radiopaque material, the radiopaque material comprising platinum/iridium, tungsten, or tantalum.

21. The device of claim 1, wherein the device is configured for insertion over the guidewire such that the guidewire extends through the single lumen from the proximal end to the distal end.

22. The device of claim 1, wherein the proximal end has a proximal opening and the distal end has a distal opening, the proximal and distal openings sized to receive the guidewire.

23. The device of claim 1, further comprising a rapid exchange opening through a wall of the catheter advancement device.

24. The device of claim 1, wherein the hypotube is coated with a lubricious polymer.

25. The device of claim 24, wherein the lubricious polymer is PTFE.

26. The device of claim 1, wherein the hypotube comprises a circular, oval, or trapezoidal D shape in cross-section.

27. The device of claim 1, wherein the hypotube comprises a skived hypotube of stainless steel.

28. The device of claim 27, wherein the skived hypotube is coupled to a proximal hub.

29. The device of claim 28, wherein the proximal hub comprises a luer thread and a luer taper inside of the hub.

30. The device of claim 28, wherein the proximal hub prevents insertion of the proximal hub through a proximal RHV.

* * * * *